(12) United States Patent
Nishide et al.

(10) Patent No.: US 10,947,212 B2
(45) Date of Patent: Mar. 16, 2021

(54) PHOTOELECTRIC CONVERSION ELEMENT, TWO-DIMENSIONAL SENSOR, IMAGE SENSOR, AND IMAGE PICKUP DEVICE

(71) Applicant: CANON KABUSHIKI KAISHA, Tokyo (JP)

(72) Inventors: Yosuke Nishide, Kawasaki (JP); Naoki Yamada, Inagi (JP); Hiroki Ohrui, Kawasaki (JP); Hironobu Iwawaki, Yokohama (JP); Satoru Shiobara, Hiratsuka (JP); Tomona Yamaguchi, Tokyo (JP); Tetsuo Takahashi, Kawasaki (JP); Masumi Itabashi, Yamato (JP); Hirokazu Miyashita, Ebina (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 153 days.

(21) Appl. No.: 16/203,298

(22) Filed: Nov. 28, 2018

(65) Prior Publication Data
US 2019/0092743 A1 Mar. 28, 2019

Related U.S. Application Data

(63) Continuation of application No. PCT/JP2017/019547, filed on May 25, 2017.

(30) Foreign Application Priority Data

May 31, 2016 (JP) .............................. JP2016-109446
Apr. 17, 2017 (JP) .............................. JP2017-081524

(51) Int. Cl.
*H01L 27/30* (2006.01)
*H01L 51/00* (2006.01)
(Continued)

(52) U.S. Cl.
CPC ......... *C07D 333/78* (2013.01); *C07D 307/93* (2013.01); *C07D 405/06* (2013.01);
(Continued)

(58) Field of Classification Search
CPC .. C07D 513/04; C07D 409/12; C07D 333/78; H01L 27/307; H01L 51/006;
(Continued)

(56) References Cited

U.S. PATENT DOCUMENTS

2013/0181202 A1* 7/2013 Yofu ........................ C09B 23/04
257/40
2014/0098272 A1* 4/2014 Nakamura ........... H04N 5/3765
348/308
(Continued)

FOREIGN PATENT DOCUMENTS

FR 3011548 A1 * 4/2015 ......... H01L 51/0061
FR 3011548 A1 4/2015
(Continued)

OTHER PUBLICATIONS

Shu-Hua Chou, Hao-Wei Kang, et al. Cofacial Versus Coplanar Arrangement in Centrosymmetric Packing Dimers of Dipolar Small Molecules: Structural Effect ACS Appl. Mater. Interfaces 2016, 8, 18266-18276 (Year: 2016).*
(Continued)

*Primary Examiner* — Bijan Ahvazi
(74) *Attorney, Agent, or Firm* — Canon U.S.A., Inc., IP Division

(57) ABSTRACT

The present invention provides an organic compound represented by general formula [1] described in claims. In general formula [1], $Ar_1$ and $Ar_2$ are each independently selected from an aryl group and a heteroaryl group. In general formula [1], $R_1$ to $R_3$ are each a hydrogen atom or a substituent. $R_4$ is an electron-withdrawing substituent. $X_1$
(Continued)

is oxygen or sulfur. $Y_1$ to $Y_3$ are each independently selected from a carbon atom and a nitrogen atom.

20 Claims, 4 Drawing Sheets

(51) Int. Cl.
  H01L 51/42       (2006.01)
  H01L 51/44       (2006.01)
  C07D 333/78      (2006.01)
  C07D 513/04      (2006.01)
  C07D 409/14      (2006.01)
  C07D 409/12      (2006.01)
  C07D 405/06      (2006.01)
  C07D 495/10      (2006.01)
  C07D 491/048     (2006.01)
  C07D 417/12      (2006.01)
  C07D 307/93      (2006.01)
  C07D 409/06      (2006.01)
  C07D 495/20      (2006.01)
  C07D 405/14      (2006.01)
  C07D 405/12      (2006.01)

(52) U.S. Cl.
  CPC ......... *C07D 405/12* (2013.01); *C07D 405/14* (2013.01); *C07D 409/06* (2013.01); *C07D 409/12* (2013.01); *C07D 409/14* (2013.01); *C07D 417/12* (2013.01); *C07D 491/048* (2013.01); *C07D 495/10* (2013.01); *C07D 495/20* (2013.01); *C07D 513/04* (2013.01); *H01L 51/006* (2013.01); *H01L 51/0053* (2013.01); *H01L 51/0061* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/442* (2013.01); *H01L 27/307* (2013.01); *H01L 51/4253* (2013.01); *H01L 51/4273* (2013.01); *Y02E 10/549* (2013.01)

(58) Field of Classification Search
  CPC .............. H01L 51/0061; H01L 51/0067; H01L 51/0072; H01L 51/0073; H01L 51/0074; H01L 51/442; H01L 51/4273
  See application file for complete search history.

(56) References Cited

U.S. PATENT DOCUMENTS

2016/0211465 A1    7/2016  Tadao
2019/0267545 A1*   8/2019  Yamaguchi ............... C07F 7/28

FOREIGN PATENT DOCUMENTS

| JP | 2007-91714 A | 4/2007 | |
| JP | 200791714 A * | 4/2007 | ......... H01L 51/0061 |
| JP | 2011-26389 A | 2/2011 | |
| JP | 2011-77198 A | 4/2011 | |
| JP | 2014-80417 A | 5/2014 | |
| KR | 10-2013-0007287 A | 1/2013 | |

OTHER PUBLICATIONS

Jae Kwan Lee, Jooyoung Kim, Hyeju Choi, Kimin Lim, Kihyung Song, Jaejung Ko, Pushepull organic semiconductors with planar indenothiophene bridges for solution-processed small-molecule organic solar cells, Tetrahedron 70 (2014) 6235e6240 (Year: 2014).*

Victorien Jeux, Olivier Segut, Dora Demeter, Olivier Aleveque, Philippe Leriche and Jean Roncali, "Push-Pull Triphenylamine Chromophore Syntheses and Optoelectronic Characterizations" ChemPlusChem, vol. 80, No. 4, pp. 697-703; 2015.

Philippe Leriche, Pierre Frere, Antonio Cravino, Olivier Aleveque and Jean Roncali; "Molecular Engineering of the Internal Charge Transfer in Thiophene-Triphenylamine Hybrid π-Conjugated Systems" Journal of Organic Chemistry; vol. 72, No. 22, pp. 8332-8336; Oct. 3, 2007.

Sophie Roquet, Antonio Cravino, Philippe Leriche, Olivier Aleveque, Pierre Frere and Jean Roncali; "Triphenylamine-Thienylenevinylene Hybrid Systems with Internal Charge Transfer as Donor Materials for Heterojunction Solar Cells" Journal of the American Chemical Society; vol. 128, No. 10, pp. 3459-3466; Feb. 18, 2006.

Salma Mohamed, Dora Demeter, Jean-Alex Laffitte, Philippe Blanchard and Jean Roncali; Structure-properties Relationships in Triarylamine-based Donor-acceptor Molecules Containing Naphtyl Groups as Donor Material for Organic Solar Cells; Scientific Reports, vol. 5: 9031, pp. 1-6, Mar. 12, 2015.

Elisa Campioli, Domna Maria Nikolaidou, Vincent Hugues, Marco Campanini, Lucia Nasl, Mireille Blanchard-Desce and Francesca Terenziani; "Amplified Two-photon Brightness in Organic Multicomponent Nanoparticles"; Journal of Materials Chemistry C, vol. 3, No. 28, pp. 7483-7491; Apr./Jun. 2015.

Xurong Qin, Xiaoyu Li, Quan Huang, Hu Liu, Di Wu, Qiang Guo, Jingbo Lan, Ruilin Wang and Jingsong You; "Rhodium(III)-Catalyzed Ortho C-H Heteroarylation of (Hetero)aromatic Carboxylic Acids: A Rapid and Concise Access to π-Conjugated Poly-Heterocycles"; Angewandte Chemie, International Edition, vol. 54, No. 24, pp. 7167-7170; 2015.

Jae Kwan Lee, Jooyoung Kim, Hyeju Choi, Kimin Lim, Kihyung Song and Jaejung Ko; "Push-pull Organic Semiconductors with Planar Indenothiophene Bridges for Solution-processed Small-molecule Organic Solar Cells"; Tetrahedron, vol. 70, No. 36, pp. 6235-6240; Feb. 18, 2014.

Shu-Hua Chou, Hao-Wei Kang, Shu-Ting Chang, Kuan-Yi Wu, Guillermo C. Azan, Chien-Lung Wang, Hong-Lin Lin, Jung-Hao Chang, Hao-Wu Lin, Yu-Ching Huang, Cheng-Si Tsao and Ken-Tsung Wong; "Cofacial Versus Coplanar Arrangement in Centrosymmetric Packing Dimers of Dipolar Small Molecules: Structural Effects on the Crystallization Behaviors and Optoelectronic Characteristics" ACS Applied Materials & Interfaces, vol. 8, No. 28, pp. 18266-18276, 2016.

Lim Kimin et al, "Organic sensitizers possessing carbazole donor and indeno[1,2-b] thiophene spacer for efficient dye sensitized solar cells", Dyes and Pigments, Elsevier Applied Science Publishers. Barking, GB, vol. 119, Mar. 18, 2015, pp. 41-48, XP029156737.

* cited by examiner

PHOTOELECTRIC CONVERSION ELEMENT, TWO-DIMENSIONAL SENSOR, IMAGE SENSOR, AND IMAGE PICKUP DEVICE

CROSS-REFERENCE TO RELATED APPLICATIONS

This application is a Continuation of International Patent Application No. PCT/JP 2017/019547, filed May 25, 2017, which claims the benefit of Japanese Patent Application No. 2016-109446, filed May 31, 2016 and No. 2017-081524, filed Apr. 17, 2017, both of which are hereby incorporated by reference herein in their entirety.

TECHNICAL FIELD

The present invention relates to a photoelectric conversion element, a two-dimensional sensor, an image sensor, and an image pickup device.

BACKGROUND ART

Photoelectric conversion elements are elements that receive light from the outside and convert the energy into electrical energy. Solid-state image pickup elements, developed by applying their characteristics, with sensors each including two-dimensionally arranged photoelectric conversion elements are widely prevalent. There have recently been advances in the development of a photoelectric conversion element including a photoelectric conversion layer containing an organic compound. However, there remains a need for improvement in, for example, conversion efficiency and durability for practical use.

Patent Literature 1 (Korean Patent No. 2013-007287) discloses organic compound a-1 having an indenothiophene structure and a dye-sensitized solar cell containing it.

Patent Literature 2 (Japanese Patent Laid-Open No. 2014-80417) discloses organic compound b-1 having a fluorene structure as a material for a photoelectric conversion element, and a photoelectric conversion element having good heat resistance and good responsiveness.

[Chem. 1]

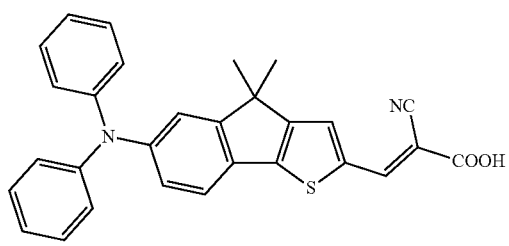

a-1

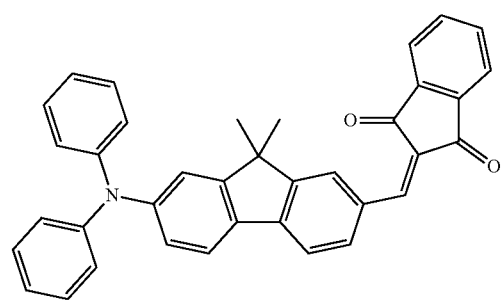

b-1

CITATION LIST

Patent Literature

PTL 1 Korean Patent No. 2013-007287
PTL 2 Japanese Patent Laid-Open No. 2014-80417

Because the organic compound disclosed in Patent Literature 1 is used as a dye for the solar cell, a structure containing a carboxy group is required. This compound has the carboxy group and thus has low thermal stability.

The organic compound disclosed in Patent Literature 2 is a compound with low absorptance of light of longer wavelengths in the visible light region.

The present invention has been made to solve the foregoing problems and aims to provide an organic compound having broad absorption in the visible light region and good thermal stability.

SUMMARY OF INVENTION

The present invention provides an organic compound represented by general formula [1] illustrated below.

[Chem. 2]

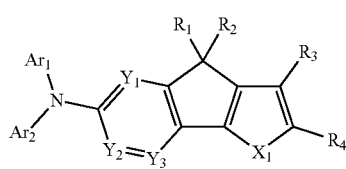

[1]

In general formula [1], $Ar_1$ and $Ar_2$ are each independently selected from the group consisting of an aryl group having 6 or more and 18 or less carbon atoms and a heteroaryl group having 3 or more and 15 or less carbon atoms.

$Ar_1$ and $Ar_2$ may each have a halogen atom, a cyano group, an alkyl group, an alkoxy group, an aryl group, or a heteroaryl group as a substituent. The substituent may further have a halogen atom, a cyano group, an alkyl group, or an alkoxy group as a substituent. $Ar_1$ and $Ar_2$ may be combined with each other to form a ring.

In general formula [1], $R_1$ and $R_2$ are each independently selected from the group consisting of a hydrogen atom, a halogen atom, a cyano group, an alkyl group, an aryl group having 6 or more and 18 or less carbon atoms, and a hetero aryl group having 3 or more and 15 or less carbon atoms.

The alkyl group may have a halogen atom as a substituent. Each of the aryl group and the heteroaryl group each denoted by $R_1$ or $R_2$ may further have a halogen atom, a cyano group, an alkyl group, or an alkoxy group as a substituent. $R_1$ and $R_2$ may be combined with each other to form a ring.

In general formula [1], $R_3$ is independently selected from the group consisting of a hydrogen atom, a halogen atom, a cyano group, and an alkyl group. The alkyl group may have a halogen atom as a substituent.

In general formula [1], $X_1$ is oxygen or sulfur.

In general formula [1], $Y_1$ to $Y_3$ are a carbon atom or a nitrogen atom, and $Y_1$ to $Y_3$ are the same or different.

When Y is a carbon atom, the carbon atom may have a hydrogen atom, a halogen atom, a cyano group, or an alkyl group as a substituent. The alkyl group may have a halogen atom as a substituent.

In general formula [1], $R_4$ is represented by general formula [1-1] or general formula [1-2]. Each * indicates a bonding position.

[Chem. 3]

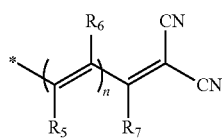

[1-1]

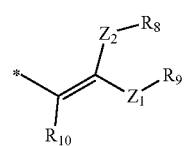

[1-2]

In general formulae [1-1] and [1-2], $R_5$ to $R_{10}$ are each independently selected from the group consisting of a hydrogen atom, a cyano group, an amino group, an amide group, an alkyl group, an alkenyl group, an alkynyl group, an aryl group having 6 or more and 18 or less carbon atoms, and a heteroaryl having 3 or more and 15 or less carbon atoms. $R_5$ and $R_7$ may be combined with each other to form a ring. $R_8$ and $R_9$ may be combined with each other to form a ring. n is an integer of 0 to 2.

In general formula [1], $Z_1$ and $Z_2$ are each independently selected from the group consisting of structures illustrated below. Each * indicates a bonding position.

[Chem. 4]

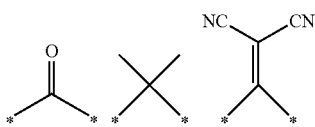

Further features of the present invention will become apparent from the following description of exemplary embodiments with reference to the attached drawings.

BRIEF DESCRIPTION OF DRAWINGS

FIG. 2 is a schematic cross-sectional view illustrating an example of a photoelectric conversion element containing an organic compound according to the present invention.

DESCRIPTION OF EMBODIMENTS

Figures 1, 1A, 2:
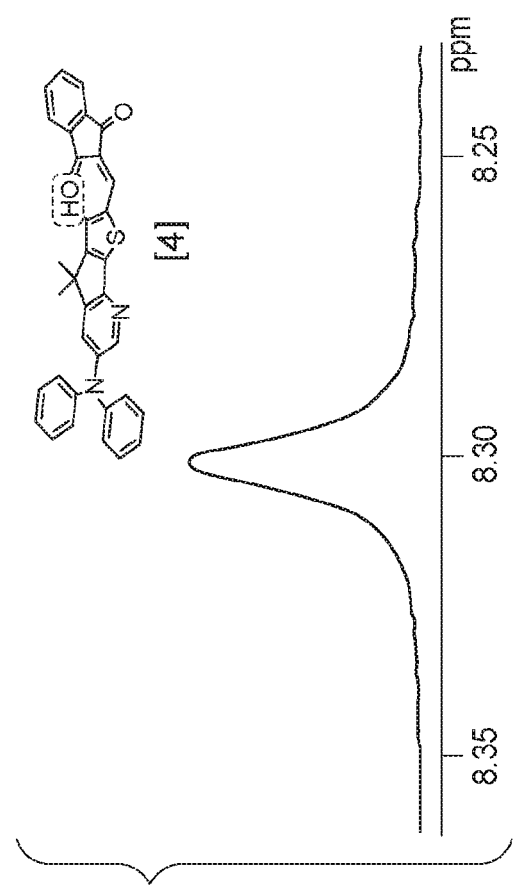
FIGS. 1A-1 and 1A-2 illustrate NMR proton signals of organic compounds according to the present invention.
Figures 1, 1A:
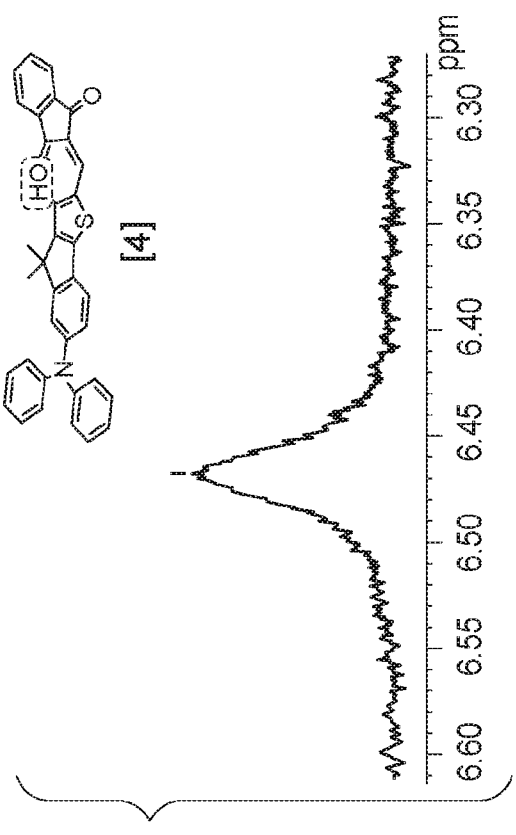
Figure 1B:
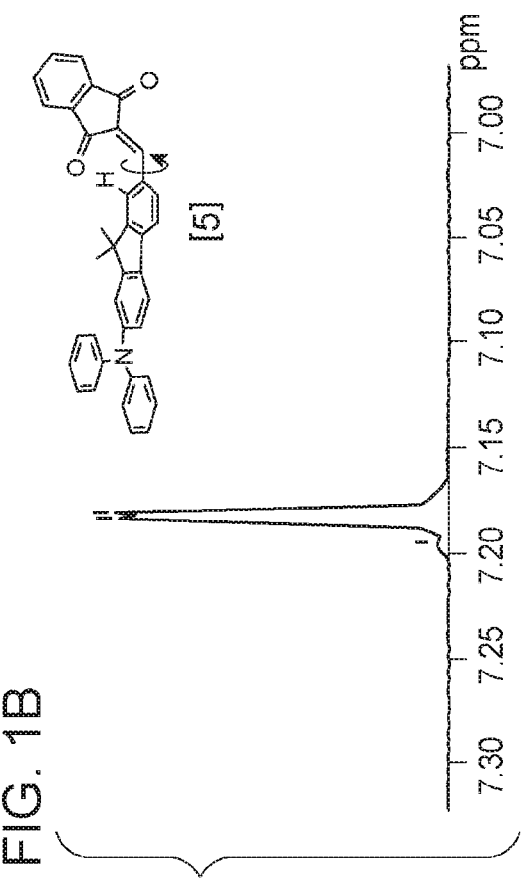
FIG. 1B illustrates an NMR proton signal of a comparative compound.
Figure 2:
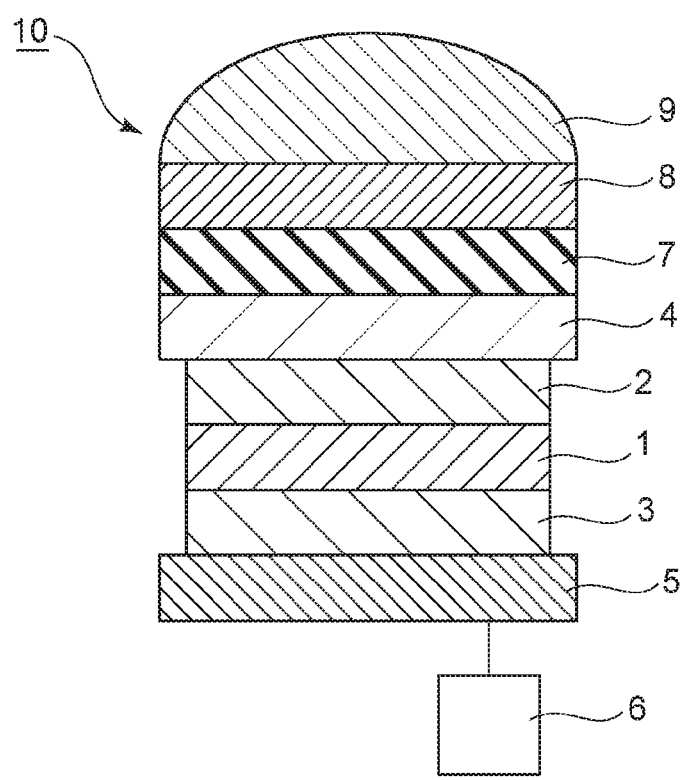

An organic compound according to the present invention has a structure in which an arylamine moiety serving as an electron-donating group (D) and an electron-withdrawing group (A) are bonded with a π-conjugated spacer including a charcogenophene, such as a furan ring or a thiophene ring, fused with an indeno group.

In this specification, a structure in which $R_1$ to $R_4$ in general formula [1] are each a hydrogen atom is also referred to as a "basic backbone of general formula [1]".

The present invention relates to an organic compound represented by general formula [1] illustrated below.

[Chem. 5]

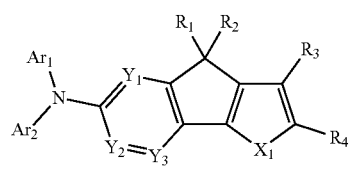

[1]

In general formula [1], $Ar_1$ and $Ar_2$ are each independently selected from an aryl group having 6 or more and 18 or less carbon atoms and a heteroaryl group having 3 or more and 15 or less carbon atoms.

Examples of the aryl group having 6 or more and 18 or less carbon atoms include a phenyl group, a biphenyl group, a terphenyl group, a naphthyl group, a phenanthryl group, and a fluorenyl group. Among these, a phenyl group, a biphenyl group, and a naphthyl group, which have relatively low molecular weights, are preferred.

The heteroaryl group having 3 or more and 15 or less carbon atoms is a heteroaryl group having at least one of oxygen, nitrogen, and sulfur as a hetero atom. Specific examples thereof include a pyridyl group, a pyrazinyl group, a pyrimidinyl group, a triazinyl group, a quinolyl group, an isoquinolyl group, an oxazolyl group, a thiazolyl, an imidazolyl group, a benzoxazolyl group, a benzothiazolyl group, a benzimidazolyl group, a thienyl group, a furanyl group, a pyronyl group, a benzothienyl group, a benzofuranyl group, an indonyl group, a dibenzothiophenyl group, and a dibenzofuranyl group. Among these, a pyridyl group, a quinolyl group, an isoquinolyl group, and a benzothienyl group, which have relatively low molecular weights and high stability, are preferred.

$Ar_1$ and $Ar_2$ each may have a halogen atom, a cyano group, an alkyl group, an alkoxy group, an aryl group, or a heteroaryl group as a substituent. The substituent may further have a halogen atom, a cyano group, an alkyl group, or an alkoxy group as a substituent. $Ar_1$ and $Ar_2$ may be combined with each other to form a ring.

The alkyl group is preferably an alkyl group that has 1 or more and 8 or less carbon atoms and that has a relatively low molecular weight. Specific examples thereof include a methyl group, an ethyl group, a n-propyl group, an iso-propyl group, a n-butyl group, an iso-butyl group, a sec-butyl group, a tert-butyl group, a n-pentyl group, a n-hexyl group, a cyclohexyl group, a n-heptyl group, a n-octyl group, and a 2-ethylhexyl group. The alkyl group may have a halogen atom as a substituent. When the alkyl group has a halogen atom as a substituent, a fluorine atom is particularly preferred.

The alkoxy group is preferably an alkoxy group that has 1 or more and 8 or less carbon atoms and that has a relatively low molecular weight. Specific examples thereof include a methoxy group, an ethoxy group, a n-propoxy group, an iso-propoxy group, a n-butoxy group, an iso-butoxy group, a sec-butoxy group, a tert-butoxy group, a n-hexyloxy group, a cyclohexyloxy group, a n-heptyloxy group, a n-octyloxy group, and a 2-ethylhexyloxy group.

Examples of the aryl group serving as a substituent of each of $Ar_1$ and $Ar_2$ include a methylphenyl group, a dimethylphenyl group, a trimethylphenyl group, a biphenyl group, and terphenyl group.

$Ar_1$ and $Ar_2$ may be combined with each other to form a ring. The ring formed is preferably, but not particularly limited to, a five-membered ring, a six-membered ring, or a seven-membered ring. The ring formed may be an aromatic ring, an aliphatic ring, or a ring having at least one double bond. The ring formed may contain a hetero atom such as nitrogen, oxygen, or sulfur.

Examples of the heteroaryl group serving as substituent of $Ar_1$ and $Ar_2$ include a pyridyl group, a quinolyl group, an isoquinolyl group, a benzothienyl group, and a benzofuranyl group.

In general formula [1], $R_1$ and $R_2$ are each independently selected from a hydrogen atom, a halogen atom, a cyano group, an alkyl group, an aryl group having 6 or more and 18 or less carbon atoms, and a heteroaryl group having 3 or more and 15 or less carbon atoms.

The alkyl group may have a halogen atom as a substituent. The aryl group and the heteroaryl group denoted by $R_1$ or $R_2$ may further have a halogen atom, a cyano group, an alkyl group, or an alkoxy group as a substituent. $R_1$ and $R_2$ may be combined with each other to form a ring.

In general formula [1], $R_3$ is independently selected from a hydrogen atom, a halogen atom, a cyano group, and an alkyl group. The alkyl group may have a halogen atom as a substituent.

In general formula [1], $X_1$ is oxygen or sulfur.

In general formula [1], $Y_1$ to $Y_3$ are a carbon atom or a nitrogen atom. $Y_1$ to $Y_3$ are the same or different.

When Y is a carbon atom, the carbon atom may have a hydrogen atom, a halogen atom, a cyano group, or an alkyl group as a substituent. The alkyl group may have a halogen atom as a substituent.

In general formula [1], $R_4$ is represented by general formula [1-1] or [1-2]. Each * indicates a bonding position. That is, each of the moieties is bonded to the basic backbone of the organic compound represented by general formula [1] at the positions indicated by *.

[Chem. 6]

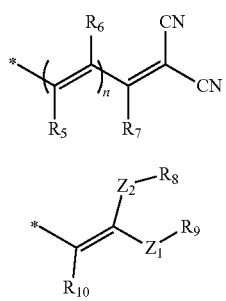

[1-1]

[1-2]

In general formulae [1-1] and [1-2], $R_5$ to $R_{10}$ are each independently selected from a hydrogen atom, a cyano group, an amino group, an amide group, an alkyl group, an alkenyl group, an alkynyl group, an aryl group having 6 or more and 18 or less carbon atoms, and a heteroaryl group having 3 or more and 15 or less carbon atoms. $R_5$ and $R_7$ may be combined with each other to form a ring. $R_8$ and $R_9$ may be combined with each other to form a ring. n is an integer of 0 to 2.

In general formula [1], $Z_1$ and $Z_2$ are each independently selected from structures illustrated below. Each * indicates a bonding position.

[Chem. 7]

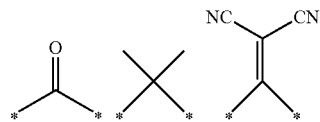

$R_4$ is a substituent containing at least one of the moieties represented by general formulae [1-1] and [1-2].

In the case where $R_4$ has a structure represented by general formula [1-2] and where $R_8$ and $R_9$ are combined with each other to form a ring, the organic compound is preferred because of its longer absorption wavelength and high thermal stability, in particular, its high melting point. Specifically, the organic compound is preferably represented by general formula [2] illustrated below.

[Chem. 8]

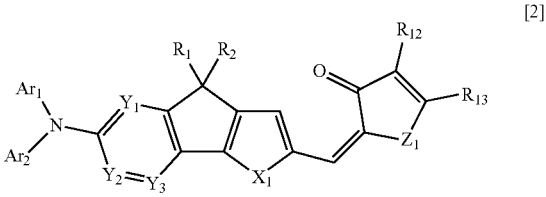

[2]

$Ar_1$, $Ar_2$, $R_1$, $R_2$, $X_1$, and $Y_1$ to $Y_3$ in general formula [2] are the same substituents as in general formula [1].

$Z_1$ in general formula [2] is selected from structures illustrated below. Each * indicates a bonding position.

[Chem. 9]

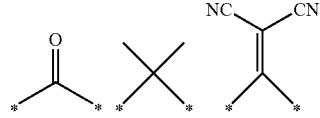

$R_{12}$ and $R_{13}$ are each independently selected from the same substituent choices as those for $R_8$ and $R_9$ in general formula [1-2]. $R_{12}$ and $R_{13}$ may be combined with each other to form a ring. The resulting ring structure may be, but not particularly limited to, an aromatic ring, an aliphatic ring, or a hetero ring. The aliphatic ring may contain at least one double bond. Specifically, the ring may be a benzene ring, a naphthalene ring, a pyridine ring, a pyrimidine ring, a pyrazine ring, a pyridazine ring, a quinoline ring, an isoquinoline ring, a quinoxaline ring, a thiophene ring, a benzothiophene ring, a furan ring, or a benzofuran ring. Examples of the structures of the rings formed are represented by general formulae [2-1] to [2-9].

[Chem. 10]

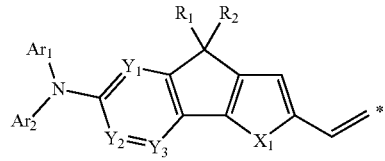

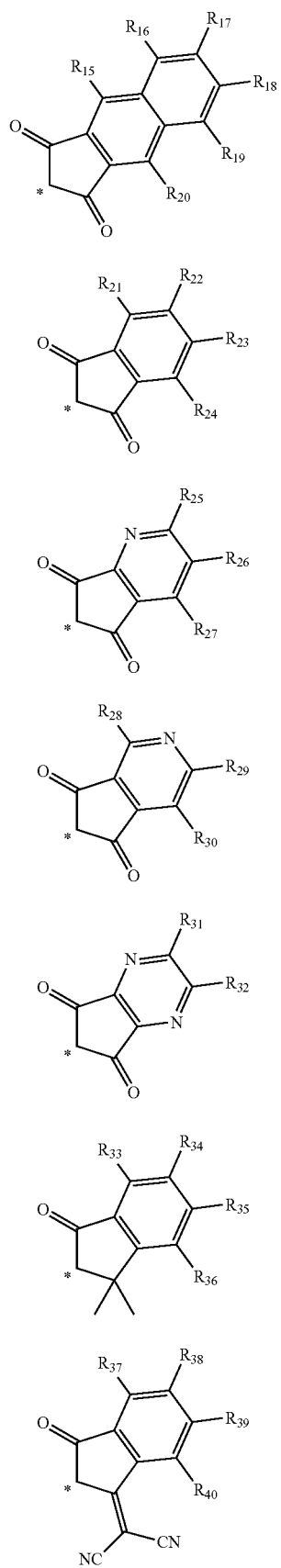

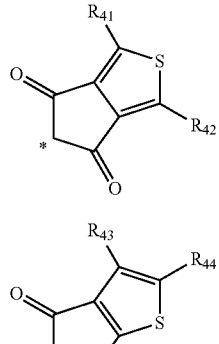

$R_{15}$ to $R_{44}$ are each independently selected from a hydrogen atom, a halogen atom, a cyano group, an alkyl group having 1 or more and 8 or less carbon atoms, an alkoxy group having 1 or more and 8 or less carbon atoms, an aryl group having 6 or more and 12 or less carbon atoms, and a heteroaryl group having 4 or more and 11 or less carbon atoms.

In general formula [2], when $Z_1$ is a carbonyl group, the organic compound is preferred because of its high thermal stability, in particular, its high melting point. Specifically, the organic compound represented by general formula [3] is preferred.

[Chem. 11]

[3]

$Ar_1$, $Ar_2$, $R_1$, $R_2$, $X_1$, and $Y_1$ to $Y_3$ in general formula [3] are the same substituents as in general formula [1]. $R_{12}$ and $R_{13}$ are the same substituents as in general formula [2]. The expression "the same substituents" indicates the same substituent choices. The substituents may be the same or different.

In general formulae [1] to [3], when $X_1$ is sulfur, the organic compound is more preferred because of its high stability.

In general formula [1], in the case where $R_4$ is represented by general formula [1-1] and where n is 0, the organic compound is preferred because of a low molecular weight and a low sublimation temperature. Specifically, the organic compound is represented by general formula [4] illustrated below.

[Chem. 12]

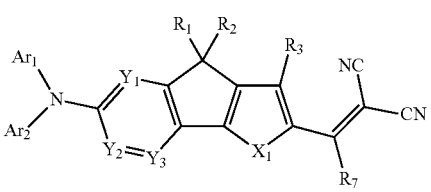

[4]

Comparison of Exemplified Compound A1 According to Present Invention and Comparative Compound a-1

Exemplified compound A1 according to the present invention is represented by a structural formula illustrated below.

[Chem. 13]

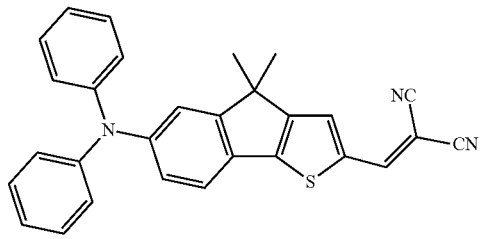

Comparative compound a-1 is represented by a structural formula illustrated below.

[Chem. 14]

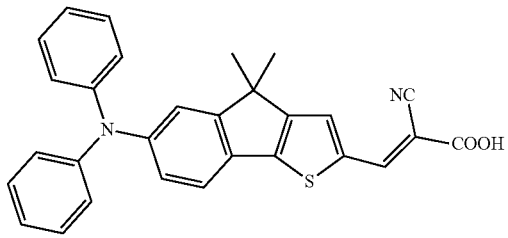

Comparisons are made between exemplified compound A1 according to the present invention and comparative compound a-1 in terms of the range of absorption in the visible light region and thermal stability.

First, the organic compound absorbs light throughout the entire visible light region. The expression "the organic compound absorbs light" indicates that the absorption of light by the organic compound can be identified. The absorption can be determined by its absorption spectrum, provided that measurement noise and so forth are not included. The expression "entire visible light region" indicates, for example, a wavelength region ranging from 380 nm to 750 nm. The organic compound that absorbs light throughout the entire visible light region is preferred because it can be used for a photoelectric conversion element and so forth.

In particular, an organic compound used for a photoelectric conversion element preferably absorbs light in the red region (600 to 750 nm) and is highly sensitive thereto.

The absorption in the red region indicates that when the organic compound is formed into a thin film, an edge of the absorption spectrum (rising edge of the absorption spectrum) of the thin film of the organic compound is present in the red region (600 nm or more).

When the measurement is performed in a dilute chloroform solution (solution having a concentration lower than $5 \times 10^{-5}$ mol/L), the edge of the absorption spectrum is preferably present at 580 nm or more, more preferably 600 nm or more.

The maximum absorption peak wavelength when the measurement is performed in the dilute chloroform solution is preferably in the range of 515 nm to 615 nm, more preferably 535 nm to 605 nm.

Table 1 presents the wavelength at the edge of the absorption spectrum and the maximum absorption peak wavelength of each of exemplified compound A1 according to the present invention and comparative compound a-1 measured in the dilute chloroform solutions.

In exemplified compound A1 according to the present invention, the wavelength at the edge of the absorption spectrum is 590 nm, and the maximum absorption peak wavelength is 535 nm. In other words, exemplified compound A1 absorbs light in the red region and thus is preferred as a compound used for a photoelectric conversion element.

In contrast, in comparative compound a-1, the wavelength at the edge of the absorption spectrum is 568 nm, and the maximum absorption peak wavelength is 481 nm. That is, comparative compound a-1 is less sensitive to the red region.

This difference is attributed to the electron-withdrawing strength of the substituents. The exemplified compound A1 according to the present invention has a strong electron-withdrawing group as a substituent located on the side of the thiophene moiety. This makes the absorption spectrum longer. Specifically, the difference is attributed to the fact that the cyano group of exemplified compound A1 according to the present invention has a higher electron-withdrawing ability than the carboxy group of comparative compound a-1.

TABLE 1

| | Exemplified compound A1 | Comparative compound a-1 |
|---|---|---|
| | 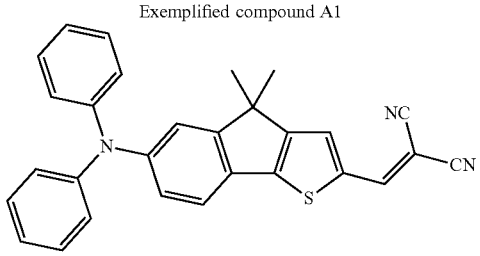 | 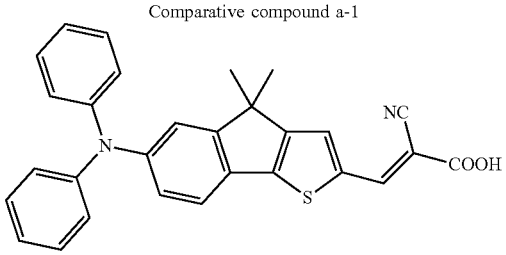 |
| | A1 | a-1 |
| Wavelength at edge of absorption spectrum/nm | 590 | 568 |
| Maximum absorption peak wavelength/nm | 535 | 481 |

In the case where the organic compound according to the present invention is used for a photoelectric conversion element, the use of only the organic compound according to the present invention can be responsible for light absorption in the entire visible light region. In the case of using a single compound responsible for light absorption, the alignment and aggregation states of the molecules are easily controlled, thus inhibiting the formation of a trap level. In addition, in the case where the organic compound is highly sensitive to light absorption, the thickness thereof can be reduced; thus, the driving voltage of an element is low.

In contrast, in the case of using a compound, such as the comparative compound, that is less sensitive to absorption in the red region, it is necessary to use a mixture of several types of compounds and increase the thickness in order to absorb light. In the case of increasing the thickness, an increase in voltage is more likely to form a trap level. In the case where the trap level is formed, the conversion efficiency is decreased to increase the voltage. Accordingly, a lager thickness is not preferred because of a high driving voltage of an element.

In the case where the organic compound according to the present invention is used for a photoelectric conversion element, an n-type semiconductor such as a fullerene analogue is preferably used as an electron acceptor. Specifically, a photoelectric conversion layer preferably contains the organic compound according to the present invention and the fullerene analogue. The use of the organic compound according to the present invention together with the fullerene analogue can enhance light absorption at shorter wavelengths, in particular, 380 nm to 500 nm.

This results in better panchromatic performance. The panchromatic performance refers to the ability to strongly absorb light in the entire visible light region.

The organic compound according to the present invention contains a nitrogen atom as represented by general formula [1] and thus has high electron-withdrawing properties. A nitrogen atom bonded to $Ar_1$ and $Ar_2$ in general formula [1] plays the role.

In the case where the organic compound according to the present invention is used for a photoelectric conversion layer together with the n-type semiconductor such as a fullerene analogue, the organic compound according to the present invention functions as an electron donor, so that good photoelectric conversion is provided. That is, the use of the organic compound according to the present invention together with the n-type semiconductor results in the panchromatic performance and good photoelectric conversion properties to provide good photoelectric conversion properties in the entire wavelength region.

Next, comparisons are made between the organic compound according to the present invention and comparative compound a-1 in terms of thermal stability and elemental durability.

The organic compound according to the present invention has high thermal stability and thus can be simply subjected to sublimation purification. Exemplified compound A1 according to the present invention has a high decomposition temperature of 307° C. and thus was able to be stably subjected to sublimation purification. The purity of organic compound according to the present invention is easily enhanced by sublimation purification.

The melting point is preferably 200° C. or higher, more preferably 240° C. or higher, still more preferably 280° C. or higher.

In contrast, comparative compound a-1 has a decomposition temperature of 189° C., which indicates low thermal stability, because it has a carboxy group. Thus, comparative compound a-1 is inappropriate for sublimation purification and vacuum deposition.

Comparative compound a-1 is a compound used for dye-sensitized solar cells and has a carboxy group because, as a photoelectric conversion compound, the compound is required to chemically modify a metal oxide such as titanium oxide. A photoelectric conversion compound for dye-sensitized solar cells has a structure containing the Bronsted acid, which is a proton donor such as a carboxy group.

Table 2 presents the decomposition temperature (temperature at which the mass is decreased by 1%) and the sublimation temperature of each of exemplified compound A1 according to the present invention and comparative compound a-1 measured by thermogravimetry-differential thermal analysis (TG-DTA), the sublimation temperature being defined as a temperature at which sublimation is performed at a rate of 10 mg/h. Although an attempt was made to subject comparative compound a-1 to sublimation purification, comparative compound a-1 was decomposed before sublimation. The reason for this is presumably that the compound has a decomposition temperature of 189° C. and thus was decomposed before the sublimation temperature.

A larger Δtemperature (melting point–sublimation temperature) is more preferred in consideration of sublimation purification. The sublimation temperature is defined as a temperature at which sublimation purification is performed at a rate of 10 mg/hour. The Δtemperature (melting point–sublimation temperature) is preferably higher than 0° C., more preferably 30° C. or higher. A Δtemperature (melting point–sublimation temperature) of 0 or lower may result in a significant decrease in sublimation rate or partial decomposition during vapor deposition.

The use of an organic compound having high thermal stability can stably produce an element even by a vacuum deposition process. In contrast, a compound having low thermal stability cannot be used in the vacuum deposition process because it is thermally decomposed. A compound having a structure such as a carboxy group is dimerized by intermolecular hydrogen bonding to increase the molecular weight and allows the highly reactive carboxy groups to bind to each other, thereby causing thermal decomposition.

TABLE 2

| Exemplified compound A1 | Comparative compound a-1 |
|---|---|
| A1 | a-1 |
| Sublimation temperature/° C. | 196 | — |
| Decomposition temperature/° C. | 307 | 189 |

The organic compound according to the present invention does not have a site to generate a proton when the organic compound absorbs light to separate charges. A generation of a large number of protons in a photoelectric conversion element can result in an increase in dark current and thus is not preferred.

In contrast, a compound having a carboxy group is ionized into a proton and a carboxylate anion. In the case where comparative compound a-1 is used for a photoelectric conversion element, protons and carboxylate anions are generated. This causes, for example, an increase in dark current and the occurrence of an irreversible reaction to accelerate the degradation of the element.

As described above, exemplified compound A1 according to the present invention is superior to comparative compound a-1 in terms of absorption sensitivity properties in the entire visible light region and thermal stability. That is, the organic compound according to the present invention has high vapor deposition stability; thus, it is possible to produce an element that can perform photoelectric conversion in the entire visible light region.

Comparison of Exemplified Compounds B16 and BB22 According to Present Invention and Comparative Compound b-1

Exemplified compound B16 according to the present invention is represented by a structural formula illustrated below.

[Chem. 15]

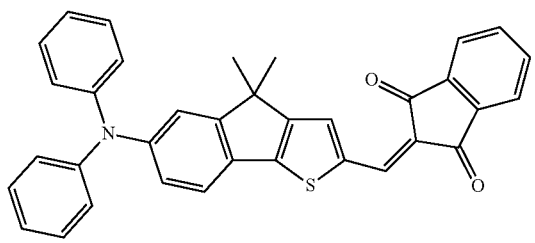

B16

Exemplified compound B22 according to the present invention is represented by a structural formula illustrated below.

[Chem. 16]

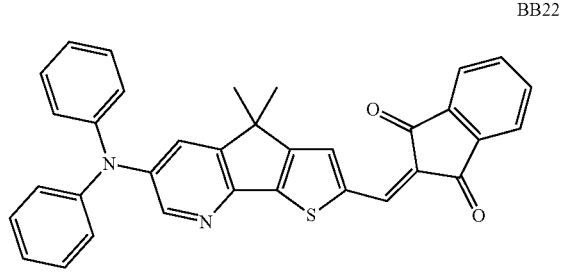

BB22

Comparative compound b-1 is represented by a structural formula illustrated below.

[Chem. 17]

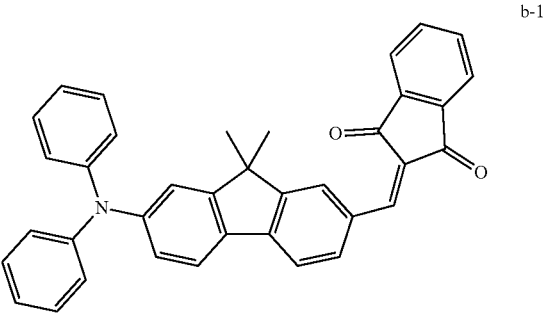

b-1

The properties of exemplified compounds B16 and BB22 according to the present invention differ significantly from those of comparative compound b-1 because they have spacer moieties with significantly different structures. The differences therebetween will be described in detail below from the two points of view: the number of ring members and the presence or absence of a hetero atom.

A first point of view is a difference in the number of members of a ring bonded to an electron-withdrawing group. The electron-withdrawing group is $R_4$ in general formula [1]. In exemplified compounds B16 and BB22 according to the present invention, the rings are five-membered rings. In comparative compound b-1, the ring is a six-membered ring. Thereby, the molecules differ from each other in the planarity and the rigidity.

In the case of a molecule having high planarity and high rigidity, the molecular motion is inhibited to raise the melting point, and the conjugation of π-electrons is lengthened. This makes the absorption wavelength longer.

In each of exemplified compounds B16 and BB22 according to the present invention as illustrated in structure formulae [4-1] and [4-2], hydrogen on the five-membered ring can be flush with a carbonyl group in the electron-withdrawing group. They are immobilized by intramolecular hydrogen bonding. This enhances the planarity and the rigidity of the molecule.

In comparative compound b-1 as illustrated in structure formula [5], hydrogen on the benzene ring adjacent to the electron-withdrawing group cannot be flash with oxygen of the carbonyl group in the electron-withdrawing moiety because of steric hindrance; thus, they are not immobilized and can rotate. Accordingly, the planarity and the rigidity of the molecule are much lower than those of exemplified compounds B16 and BB22 according to the present invention.

FIGS. 1A-1, 1A-2, and 1B illustrate proton signals measured by $^1$H-NMR in d-tetrahydrofuran. The vertical axis represents the signal intensity. The signals of hydrogen on the thiophene rings of structure formulae [4-1] and [4-2] are observed as broad peaks, which indicates that intramolecular interaction occurs.

In contrast, the signal of hydrogen on the benzene ring in structure formula [5] is observed as a sharp peak, which indicates that intramolecular interaction does not occur.

Accordingly, the bonding of the electron-withdrawing group, in particular, the carbonyl group-containing substituent, to the five-membered ring improves the planarity and the rigidity to provide the effects of making the absorption wavelength longer and improving the melting point.

[Chem. 18]

[4-1]

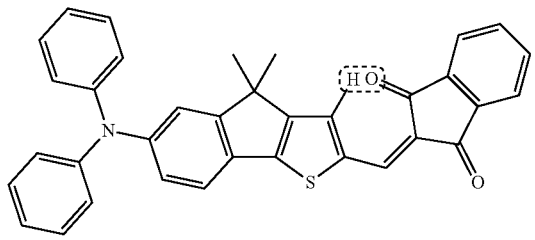

[4-2]

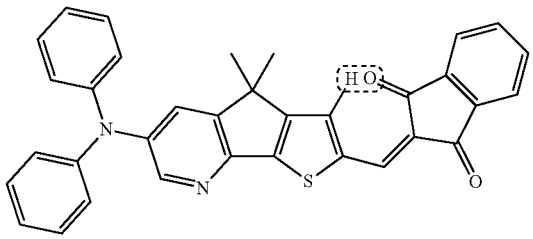

[5]

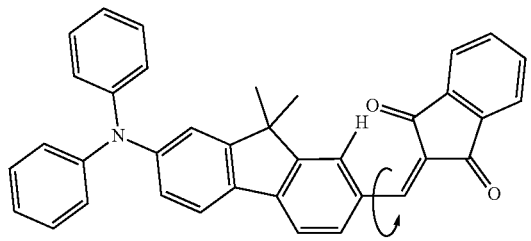

Second, each of exemplified compounds B16 and BB22 according to the present invention has a π-electron-rich thiophene ring. Thus, the thiophene ring has an improved electron density, compared with the benzene ring in comparative compound b-1. This can make the absorption wavelength in the absorption spectrum longer. A furan ring, which is the same π-electron-rich system, also has this effect.

Table 3 presents absorption edge wavelengths and the maximum absorption peak wavelengths in absorption spectra measured in dilute chloroform solutions, and melting points.

The absorption edge wavelengths in the absorption spectra of exemplified compounds B16 and BB22 according to the present invention are longer than that of comparative compound b-1 by 36 nm and 26 nm, respectively. The maximum absorption peak wavelengths in the absorption spectra of exemplified compounds B16 and BB22 are longer than that of comparative compound b-1 by 59 nm and 39 nm, respectively. The melting points of exemplified compounds B16 and BB22 are higher than that of comparative compound b-1 by 46° C. and 33° C., respectively.

The organic compound according to the present invention is more thermally stable than comparative compound b-1 and absorbs light in a long wavelength region, specifically, in the red region, compared with comparative compound b-1. Accordingly, the organic compound according to the present invention can be suitably used for a photoelectric conversion element.

TABLE 3

| | B16 | BB22 | b-1 |
|---|---|---|---|
| Absorption edge wavelength in dilute chloroform solution/nm | 620 | 610 | 584 |
| Maximum absorption wavelength in dilute chloroform solution/nm | 569 | 549 | 510 |
| Melting point/° C. | 308 | 295 | 262 |

Characteristics of Photoelectric Conversion Element According to Present Invention As illustrated in general formula [1], the organic compound according to the present invention has a structure in which an arylamine moiety serving as an electron-donating group (D) and an electron-withdrawing group (A) are bonded with a π-conjugated spacer including a charcogenophene, such as a furan ring or a thiophene ring, fused with an indeno group.

The organic compound according to the present invention has the electron-withdrawing group containing no Bronsted acid and thus has high thermal stability. Even if the organic compound is used for a photoelectric conversion element, the photoelectric conversion element having suppressed dark current and high elemental durability can be produced.

[Chem. 19]

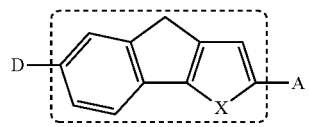

[6]

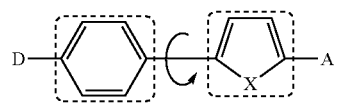

[7]

TABLE 4

| | Exemplified compound A1 | Comparative compound a-2 |
|---|---|---|
| | A1 | a-2 |
| Maximum absorption wavelength/nm | 535 | 507 |
| Molar extinction coefficient/$M^{-1}cm^{-1}$ | 57600 | 37600 |
| Melting point/° C. | 215 | 180 |

The organic compound according to the present invention does not have a rotation axis in the π-conjugated spacer. This stabilizes a π-electron or an electron associated with light absorption transition and results in the absorption of light with longer wavelengths than that of a compound having a rotation axis in the spacer. That is, the absorption sensitivity to red light is improved.

The organic compound according to the present invention has no rotation axis in the spacer and thus has the effect of improving the transition probability of an electron between D and A in its molecule. For example, as illustrated in structure formula [7], in the case where a rotation axis is present between D and A, energy levels corresponding to rotational states are present, thus decreasing the transition probability from D to A. That is, a smaller number of rotation axes between D and A results in higher transition probability. High transition probability between D and A results in a high molar extinction coefficient. If an organic compound having a high molar extinction coefficient is used for a photoelectric conversion layer, a small thickness can be used. The small thickness contributes to a reduction in the voltage of an element.

Table 4 presents the maximum absorption peak wavelengths, the molar extinction coefficients, which are measured in dilute chloroform solutions, and the melting points of exemplified compound A1 according to the present invention and comparative compound a-2. The results also indicate that the compound according to the present invention having a highly planar π-conjugated spacer that has no rotation axis is superior.

The organic compound according to the present invention is highly stable in a radical cation state.

When photoelectric conversion elements absorb light to separate charges, radical cation species and radical anion species are formed. These species must be collected by both electrodes. Thus, a compound used for photoelectric conversion elements preferably has higher stability in a radical cation state. In particular, when the compound is used together with an n-type semiconductor such as a fullerene analogue, the high stability thereof is highly effective.

Regarding the compound according to the present invention, the five-consecutive sweep evaluation of one-electron oxidation in cyclic voltammetry (CV) measurement revealed that a reversible oxidation wave was obtained and that no degradation was observed by repeated sweeping. This indicates that even if the compound is subjected to one-electron oxidation, the compound can be stably present without decomposition or reaction. Thus, in the case where the organic compound according to the present invention is used for an organic compound layer of an organic photoelectric conversion element, a highly durable element is provided.

The CV measurement was performed in a 0.1 M solution of tetrabutylammonium perchlorate in ortho-dichlorobenzene with a reference electrode of $Ag/Ag^+$, a counter electrode of Pt, and a working electrode of glassy carbon. The sweep rate was 0.1 V/s. As a measurement device, a Model 660C electrochemical analyzer, available from ALS Co., Ltd., was used.

As described above, the organic compound according to the present invention has a broad light absorption and high thermal stability and thus can be suitably used for a photoelectric conversion element. A photoelectric conversion element containing the organic compound according to the present invention has a broad light absorption and is operated at a low voltage with high efficiency and high durability.

In the case where at least one of $Y_1$ to $Y_3$ in general formula [1] is a nitrogen atom, a deep HOMO level is obtained, compared with the case where $Y_1$ to $Y_3$ are each a carbon atom. The use of the compound for a photoelectric conversion element is more effective in suppressing dark current. The expression "deep HOMO level" can also be referred to as a "high HOMO level". The same is true for LUMO. The deep HOMO level indicates a large absolute value of the HOMO level and a large distance from the vacuum level.

In a photoelectric conversion element, upon applying a voltage, a current flows without irradiation with light, in some cases. Unlike solar cells, dark current is not preferred in view of the characteristics of the element. One of the factors of the generation of the dark current is seemingly that only the application of a voltage in the dark results in an interaction between the HOMO level of a molecule to be excited by absorbing light and the LUMO levels of an n-type semiconductor such as a fullerene analogue that accelerates photoinduced charge separation and a peripheral charge blocking layer, thereby generating the dark current in the photoelectric conversion layer. The reason for this is that the LUMO levels of the n-type semiconductor such as a fullerene analogue and the peripheral charge blocking layer are deep and thus are close to the HOMO level of the molecule to be excited by absorbing light. Thus, charge transfer occurs easily between these two molecules.

An example of a method for reducing dark current without decreasing photoelectric conversion efficiency is to selectively deepen the HOMO level of the molecule to be excited by absorbing light in order to reduce the HOMO-LUMO interaction between the two molecules.

The organic compound according to the present invention is a molecule that is excited by absorbing light and that has a structure in which an amino group is bonded to a nitrogen-containing hetero ring, which is a π-electron-deficient system. The HOMO level of the molecule is affected by the electron states of the amino group and its periphery. The LUMO level of the molecule is affected by the electron states of the substituent represented by $R_4$ in general formula [1] and its periphery.

Thus, the HOMO level varies, depending on the properties of the substituent to which the amino group is attached. In the compound in which at least one of $Y_1$ to $Y_3$ in general formula [1] is a nitrogen atom, the amino group and the nitrogen-containing hetero ring, which is a π-electron-deficient system, are bonded together; thus, electrons near the electron-rich amino group are stabilized to deepen the HOMO level. That is, only the HOMO level can be deepened without affecting the LUMO level.

Accordingly, in the case where the organic compound according to the present invention in which at least one of $Y_1$ to $Y_3$ in general formula [1] is a nitrogen atom is used as a photoelectric conversion layer of an organic photoelectric conversion element, dark current can be suppressed without decreasing the photoelectric conversion efficiency.

Example of Organic Compound According to Present Invention

Specific structure formulae of the organic compound according to the present invention will be exemplified below. The present invention, however, is not limited to these specific examples.

[Chem. 20]

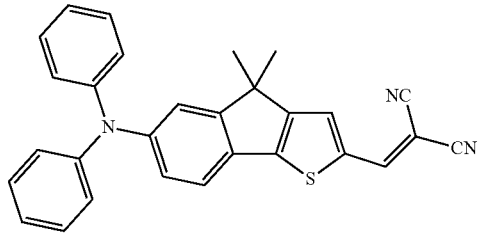

A1

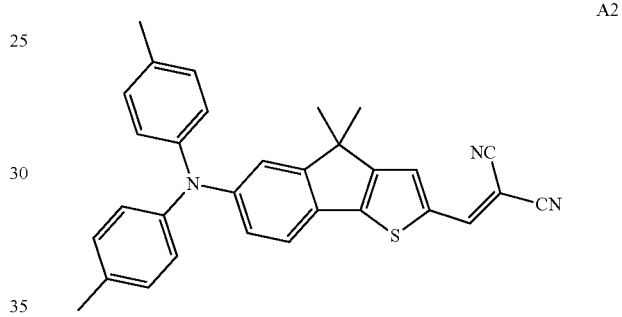

A2

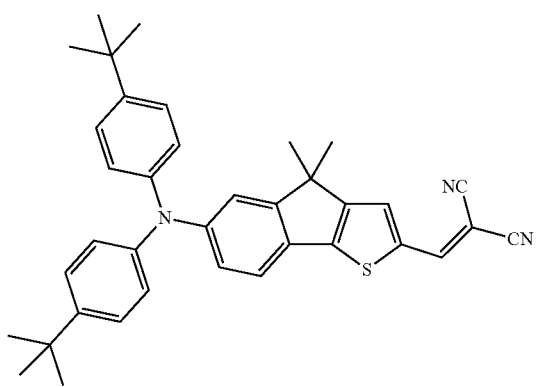

A3

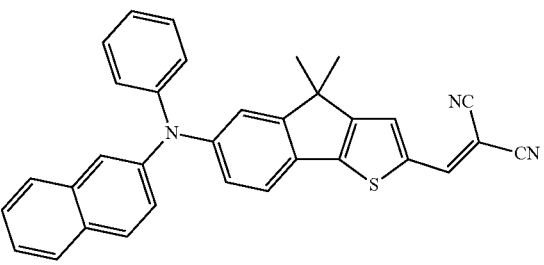

A4

-continued
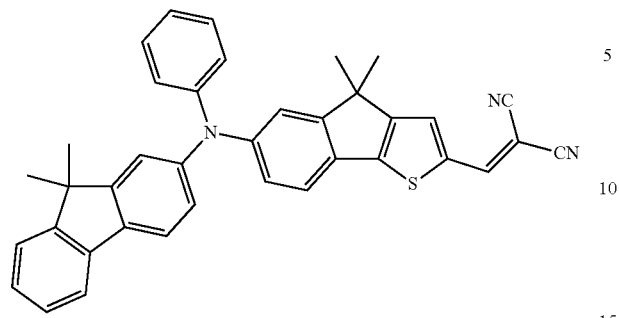
A5
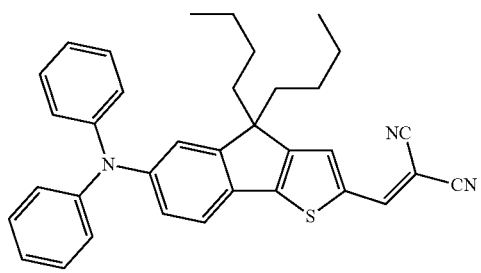
A9
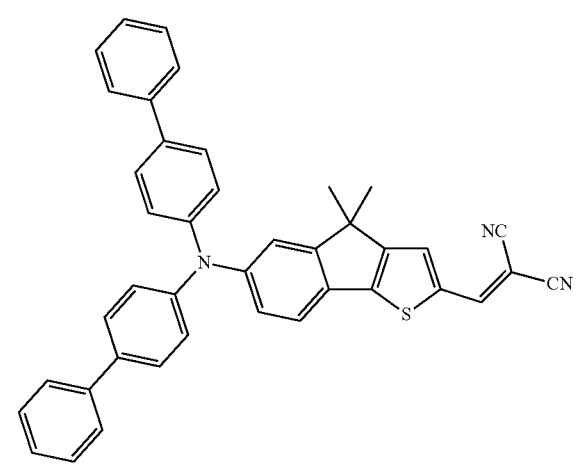
A6
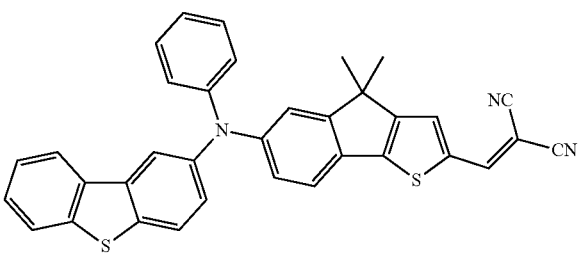
A10
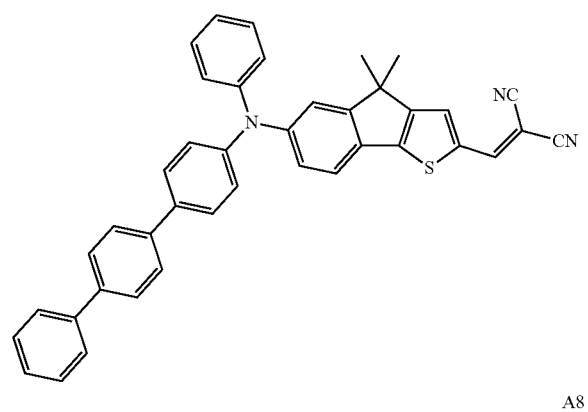
A7
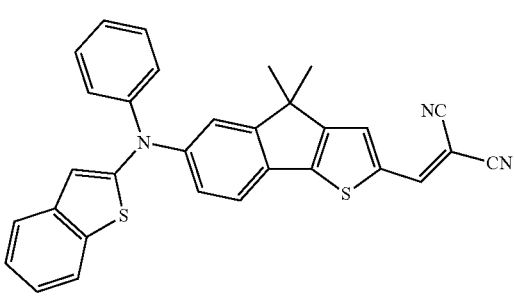
A11
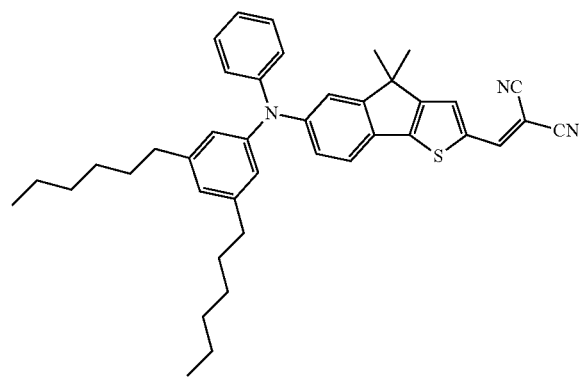
A8
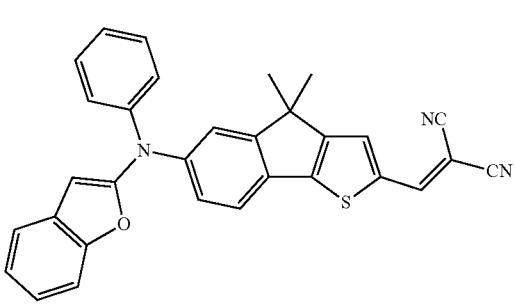
A12
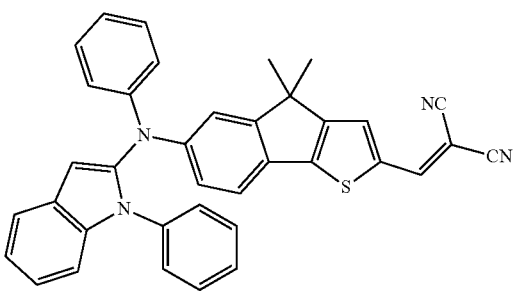
A13

A14
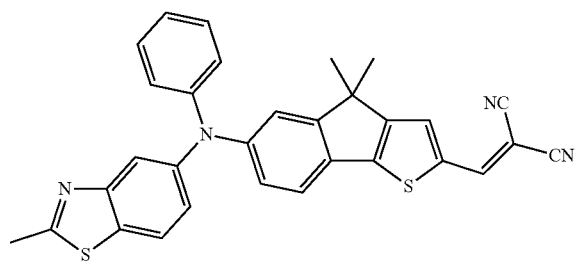
A15
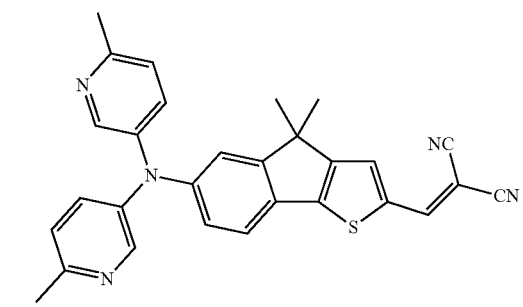
A16
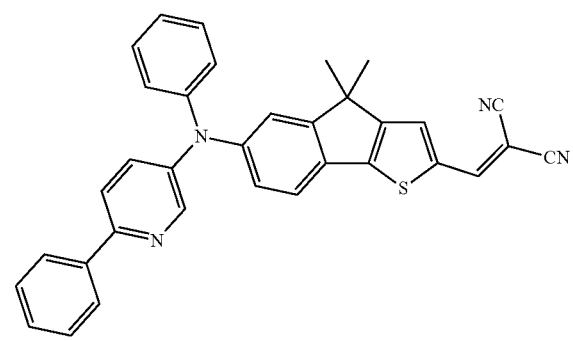
A17
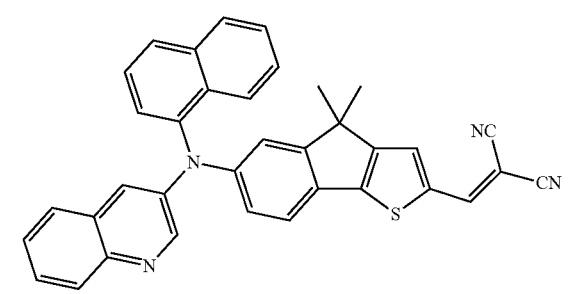
A18
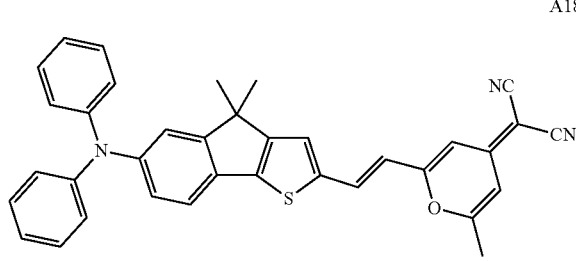
A19
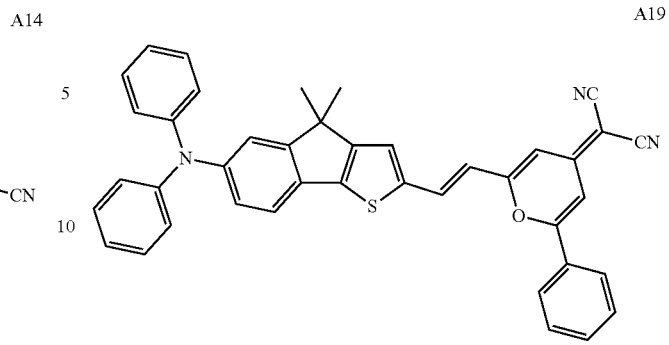
A20
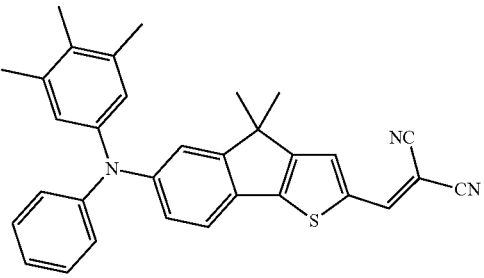
[Chem. 21]
A21
A22
A23
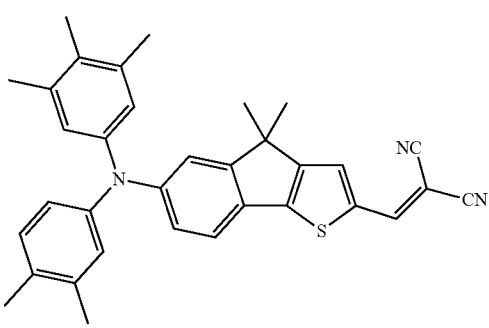

A24
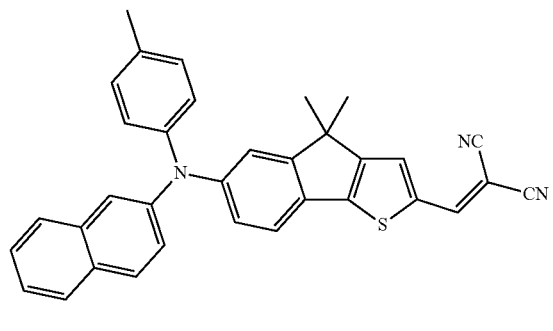
A25
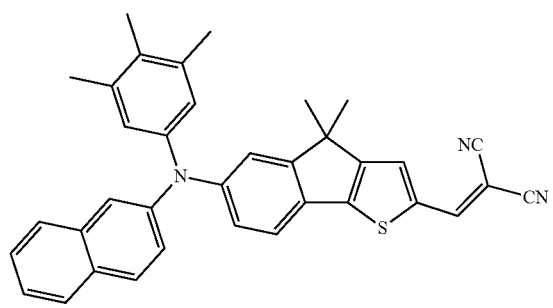
A26
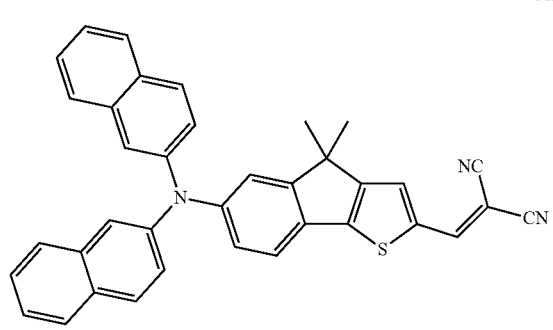
A27
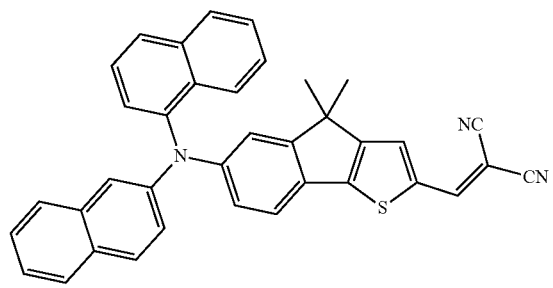
A28
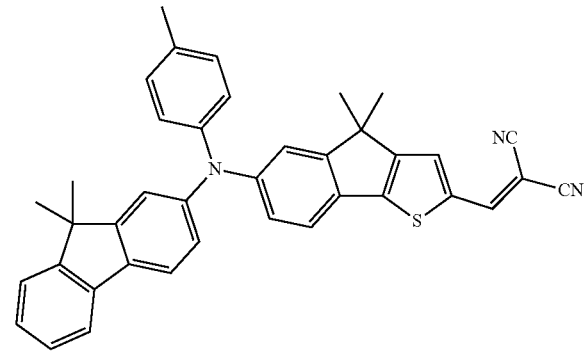
A29
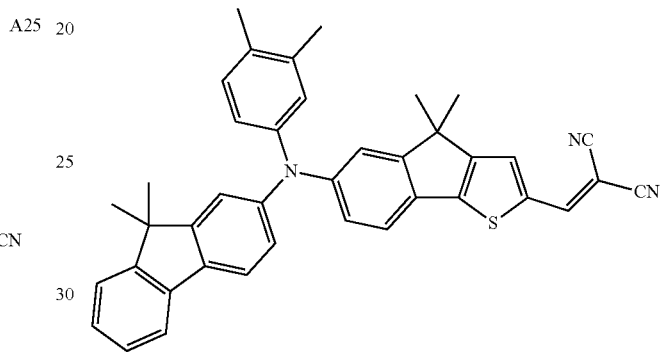
A30
A31
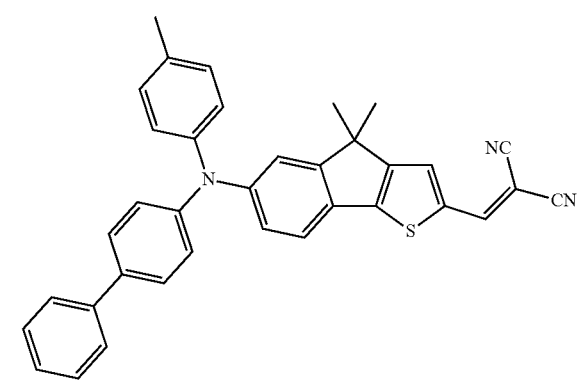

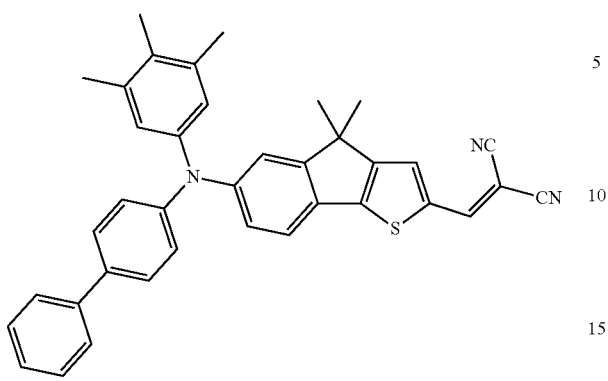
A32
A33
A34
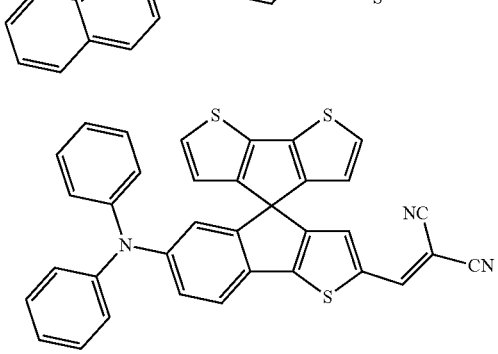
A35
A36
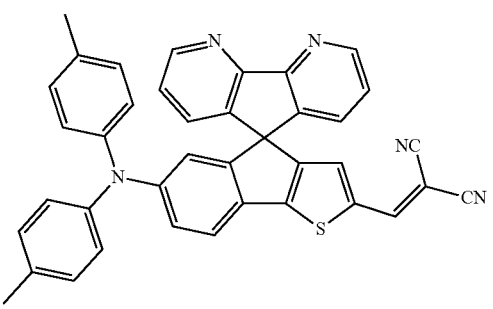
A37
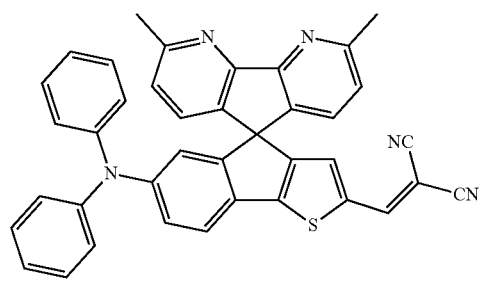
A38
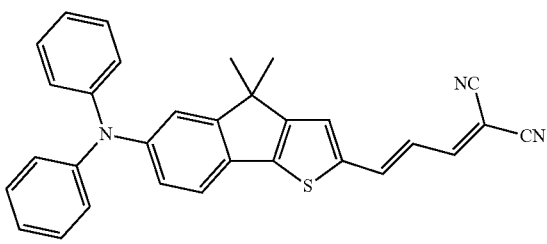
A39
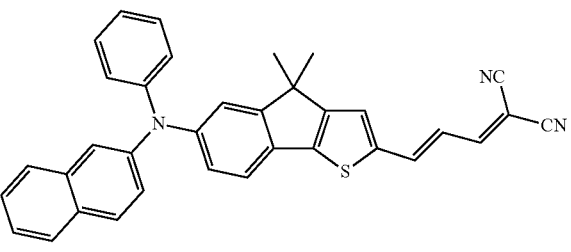
A40
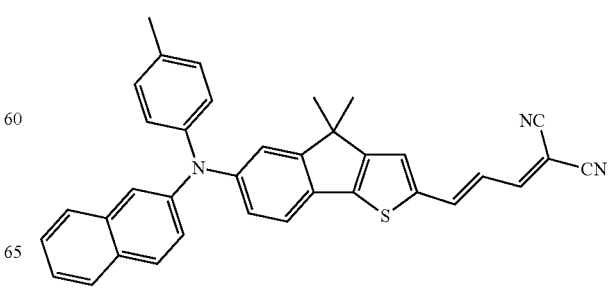
A41

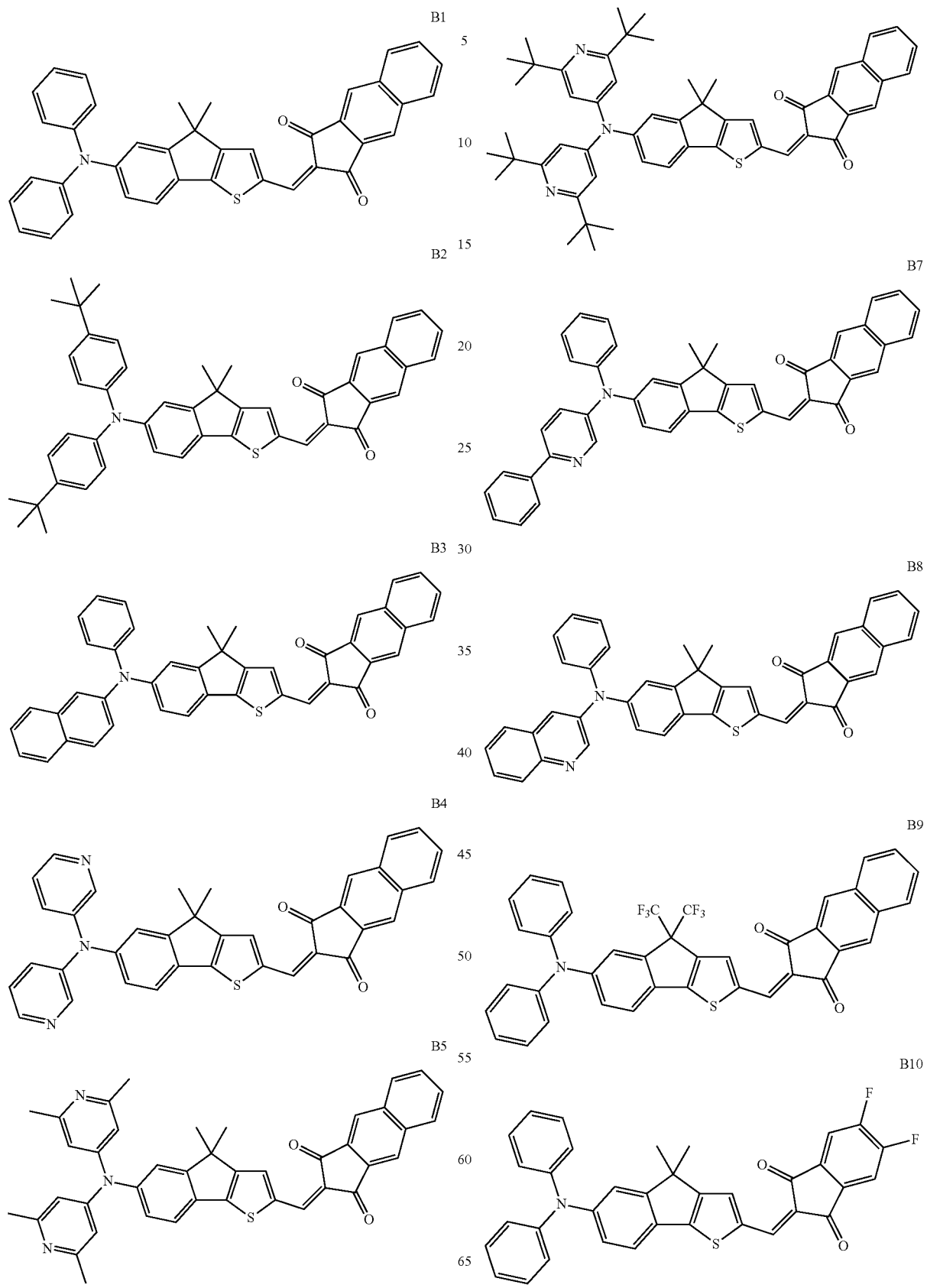

-continued
B11
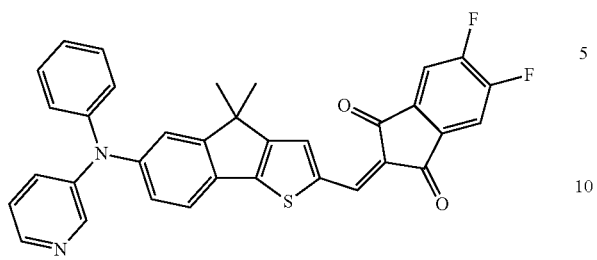
B12
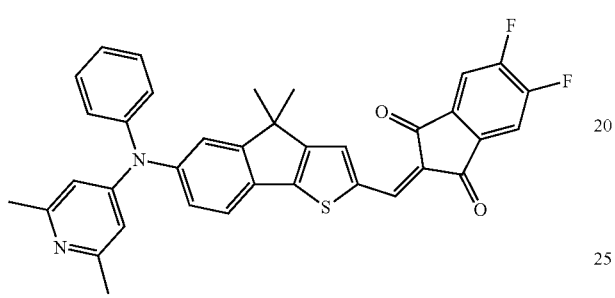
B13
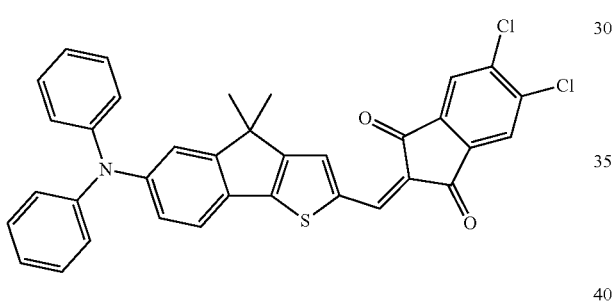
B14
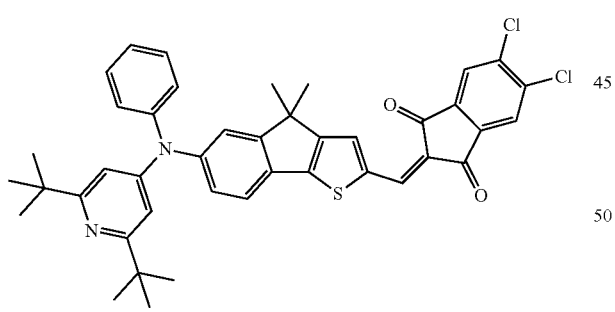
B15
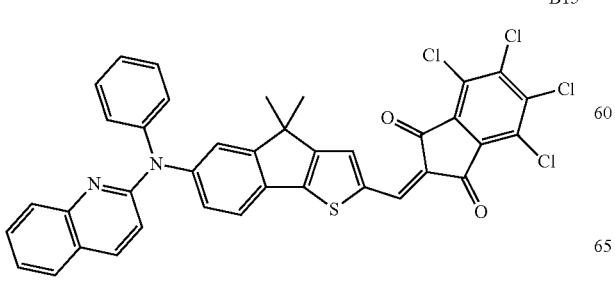
-continued
B16
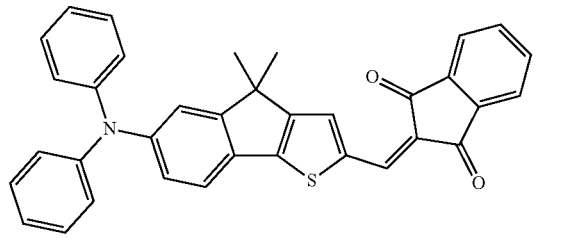
B17
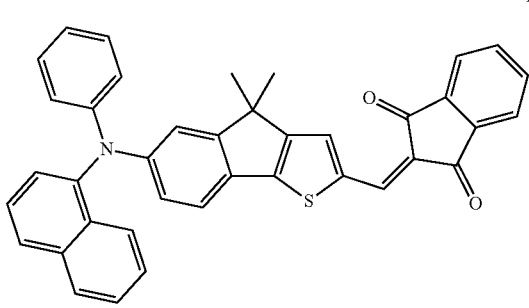
B18
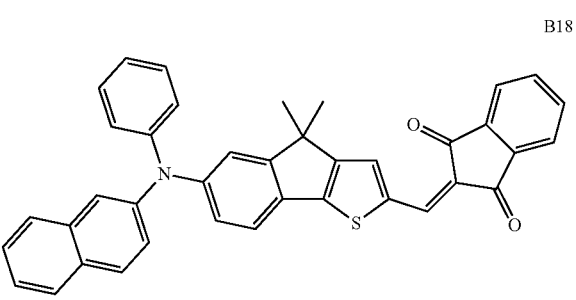
B19
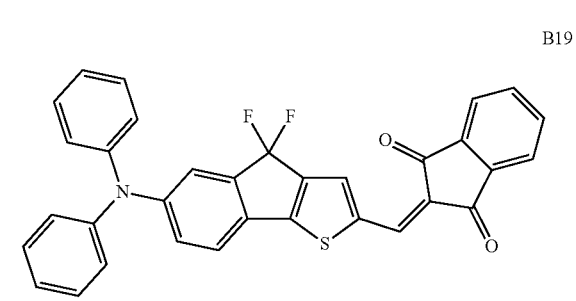 [SMILES: CC1(C)c2cc(C=C3C(=O)c4ccccc4C3=O)sc2-c2ccc(N(c3ccccc3)c3ccccc3)nc21]
B20
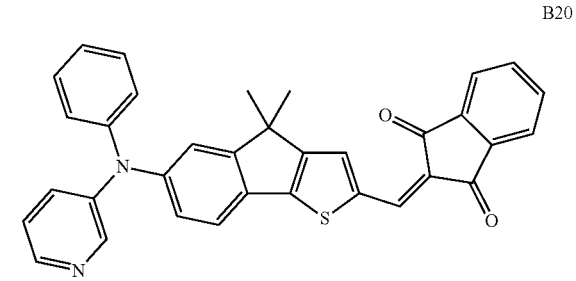

B21 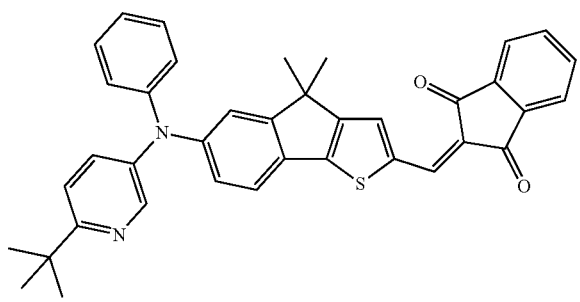
B22 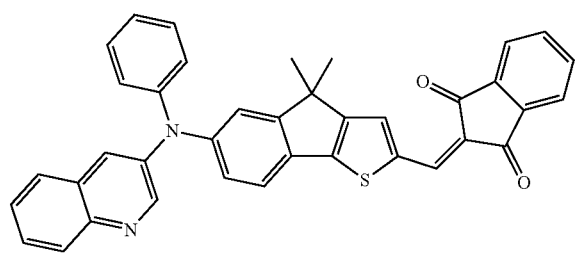
B23 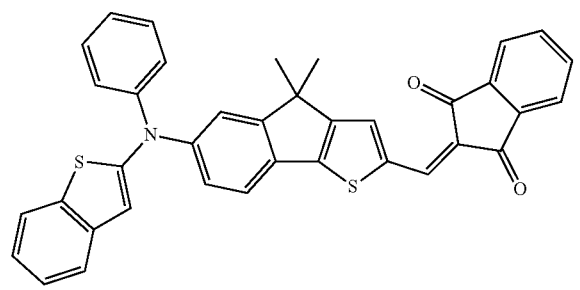
B24 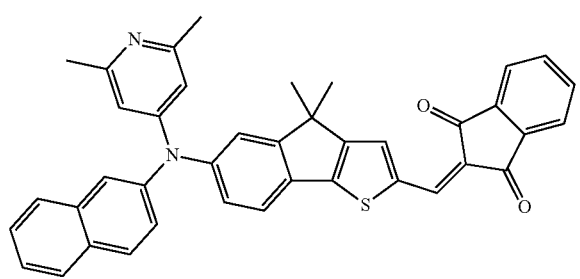
[Chem. 23]
B25 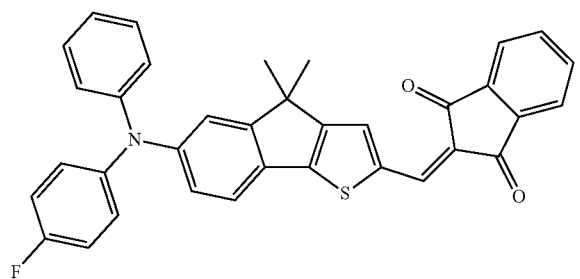
B26 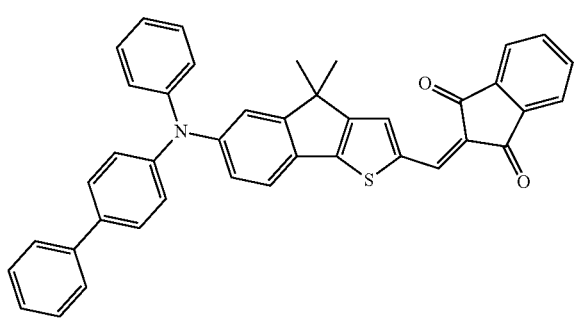
B27 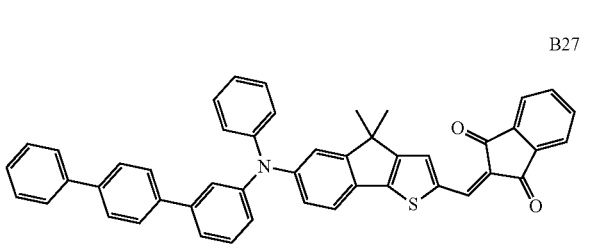
B28 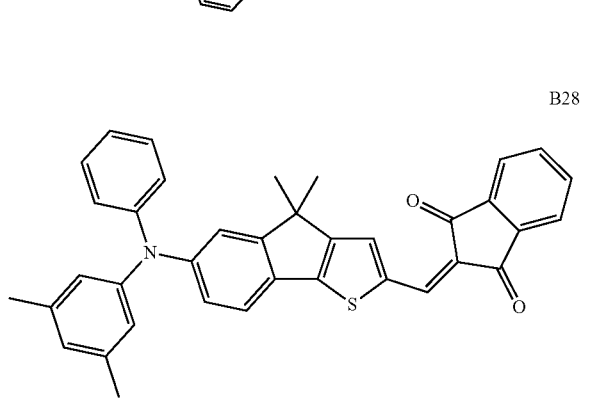
B29 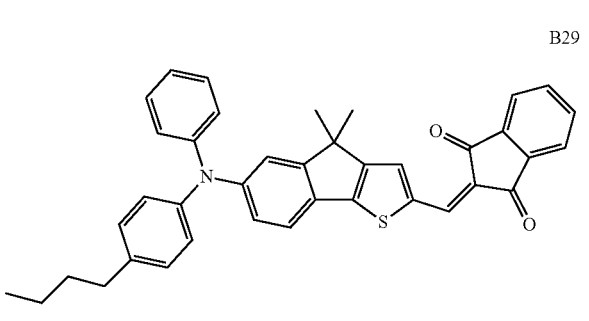
B30 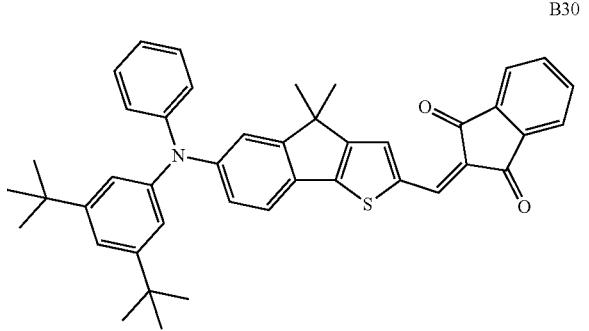

B31 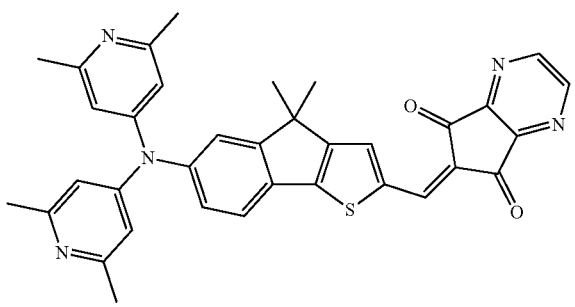
B36 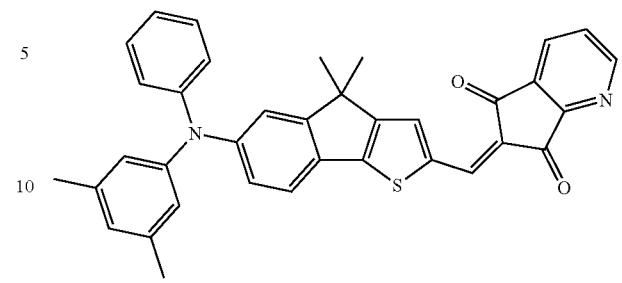
B32 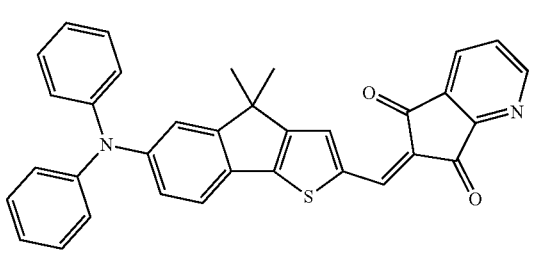
B37 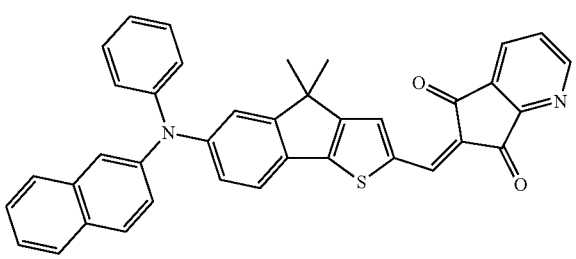
B33 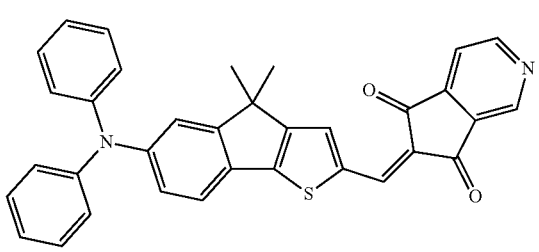
B38 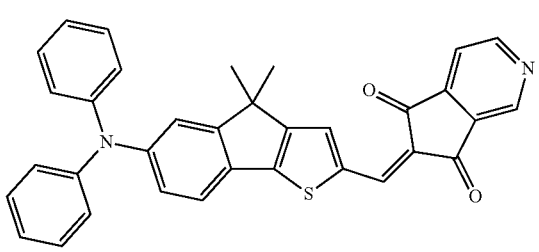
B34 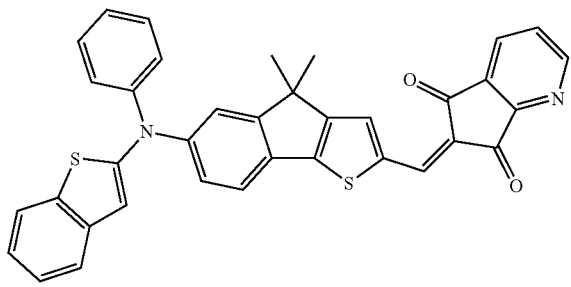
B39 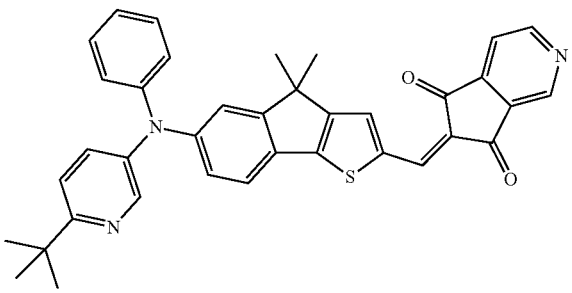
B35 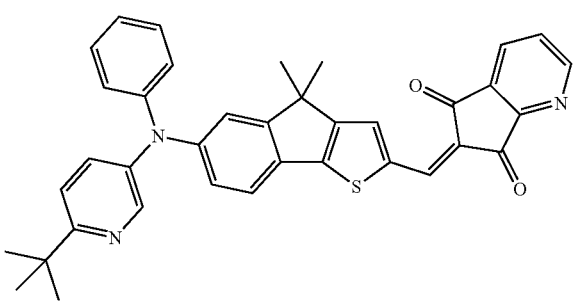
B40 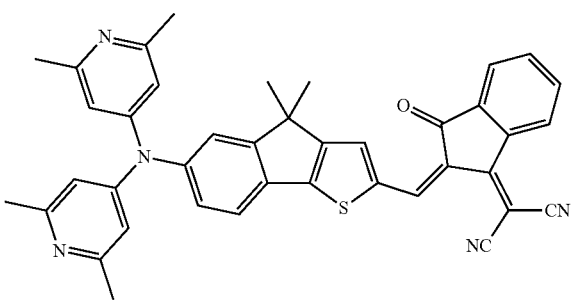

-continued
B41
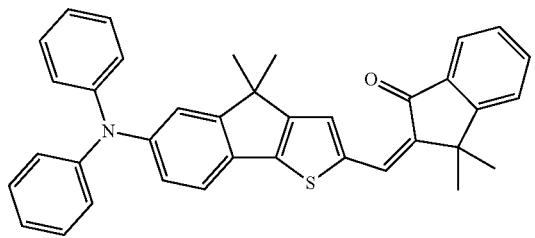
B42
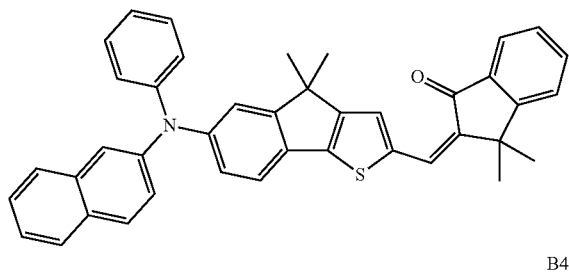
B43
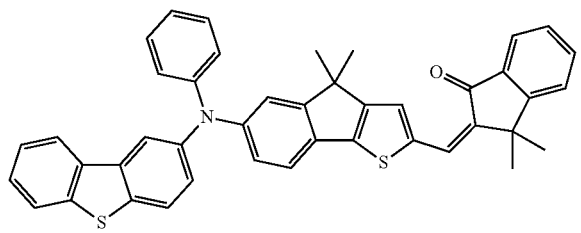
B44
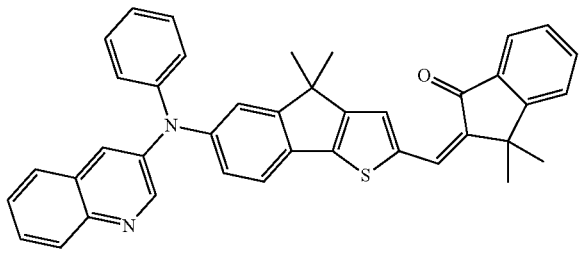
B45
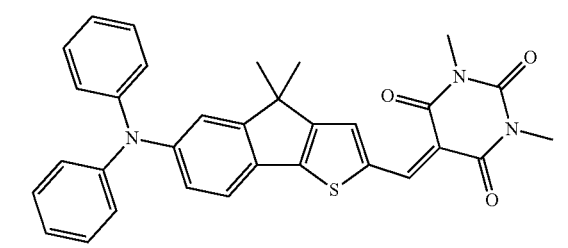
B46
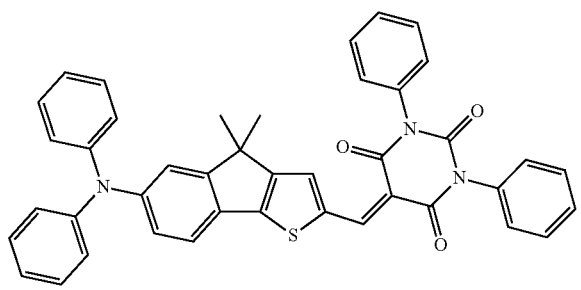
-continued
B47
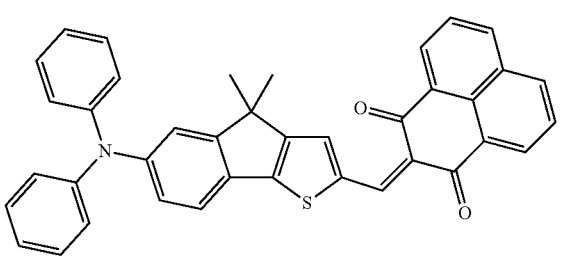
B48
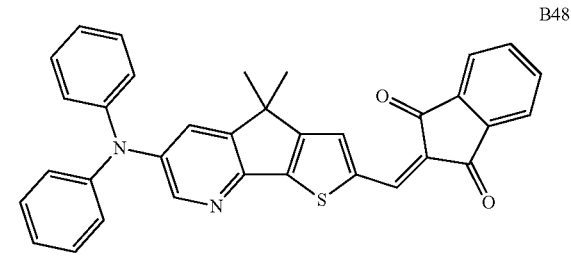
[Chem. 24]
B49
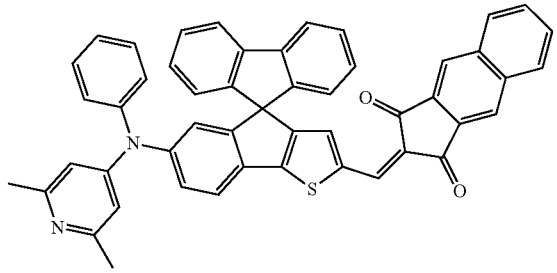
B50
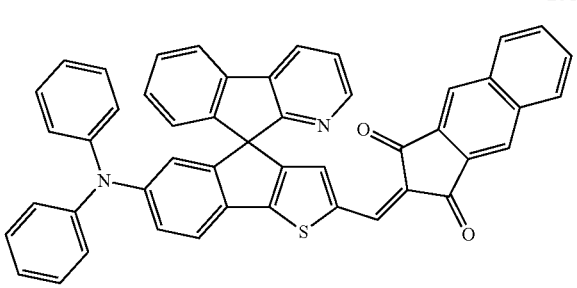
B51

B52 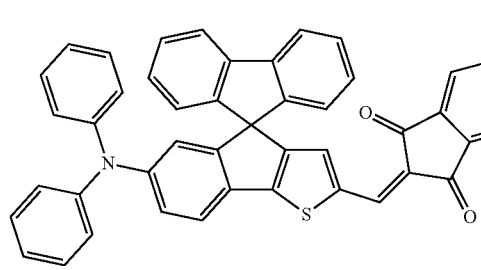
B53 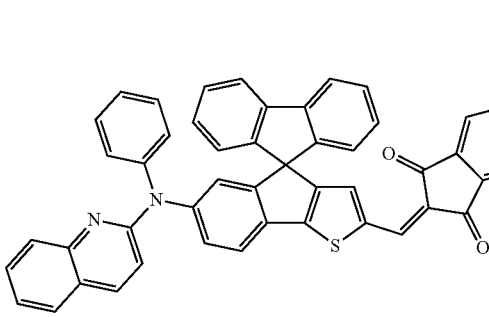
B54 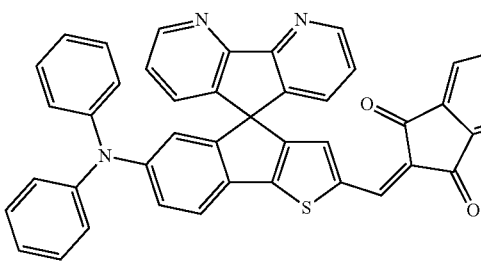
B55 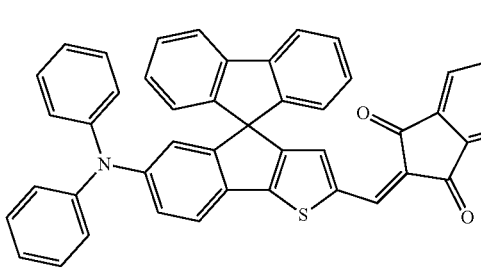
B56 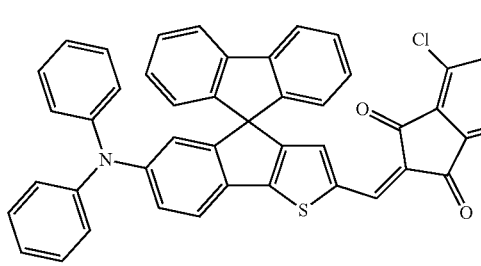
B57 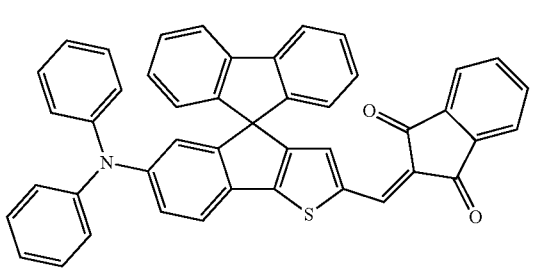
B58 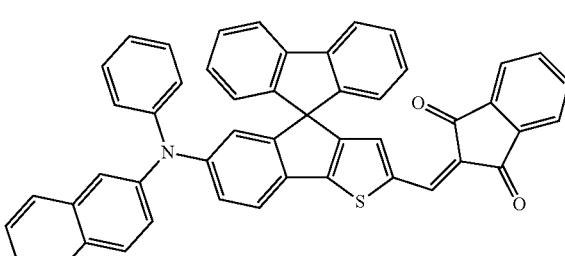
B59 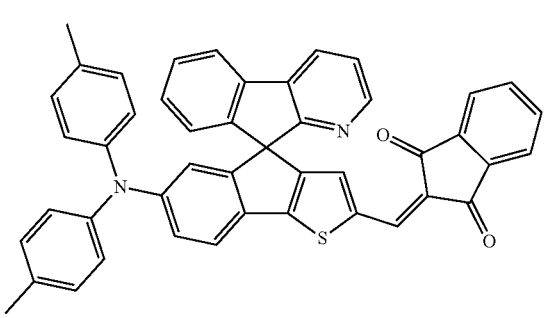
B60 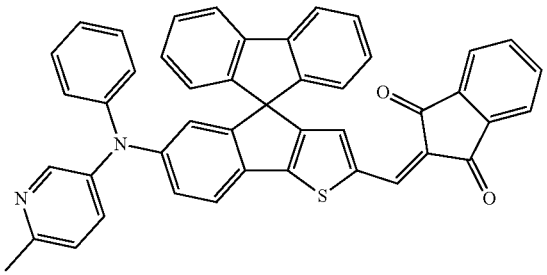
B61 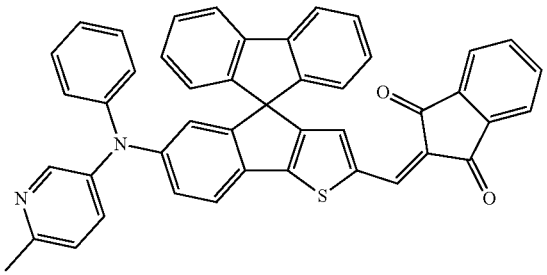

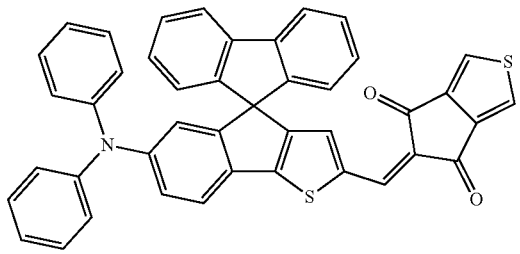
B62
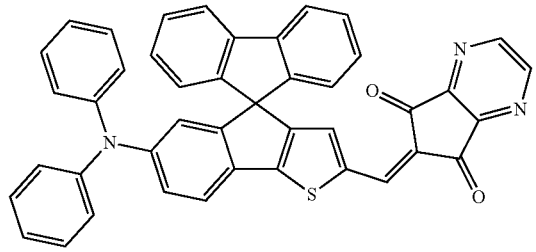
B67
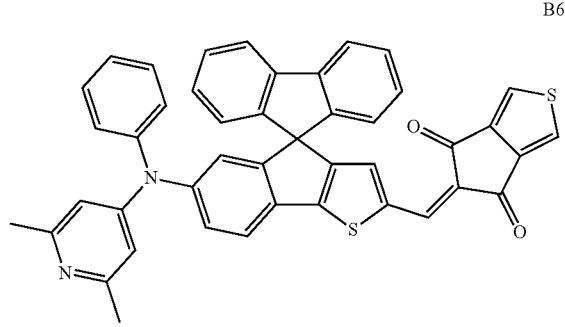
B63
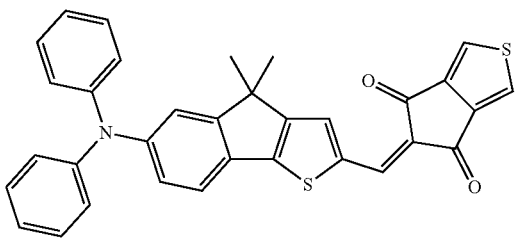
B68
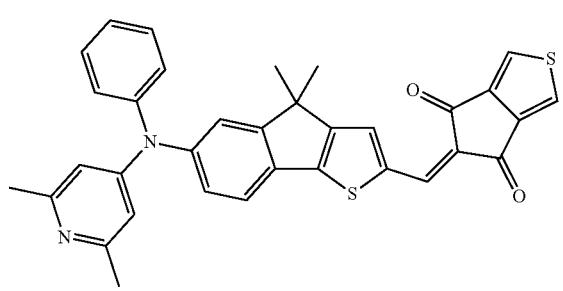
B69
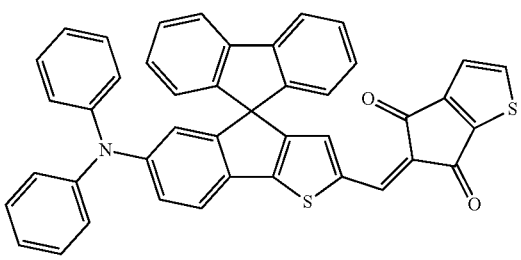
B64
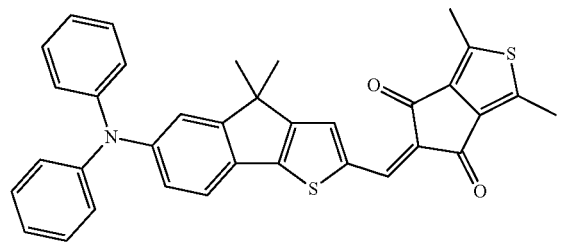
B70
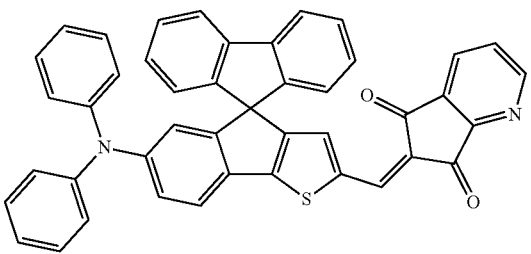
B65
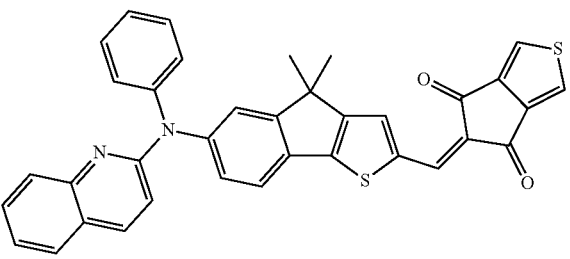
B71
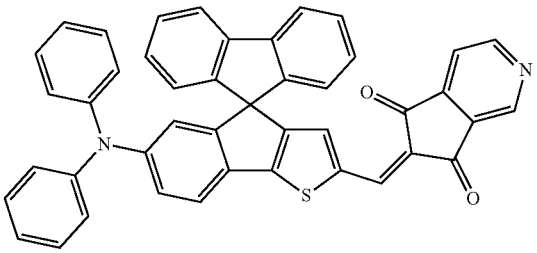
B66
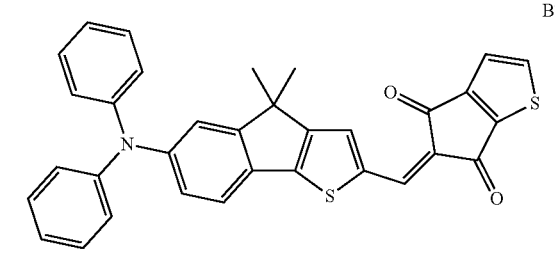
B72

[Chem. 25]
C1
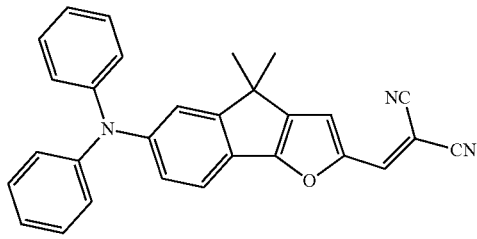
C2
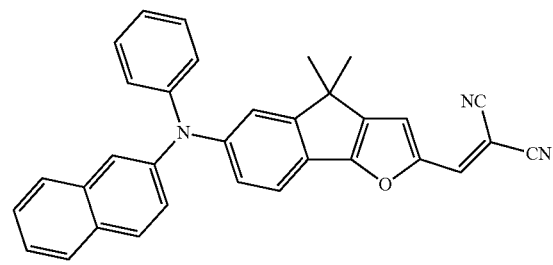
C3
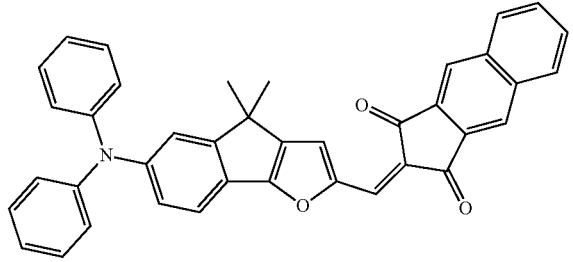
C4
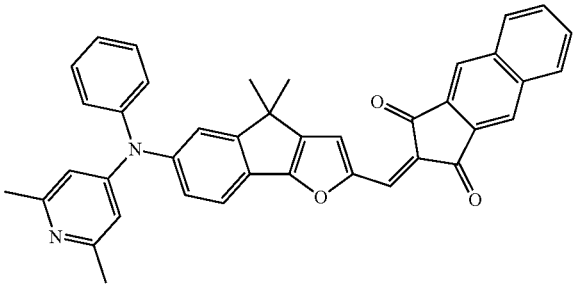
C5
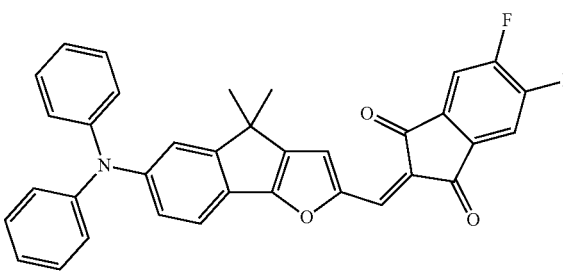
C6
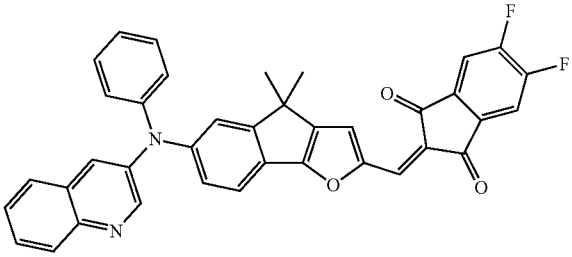
C7
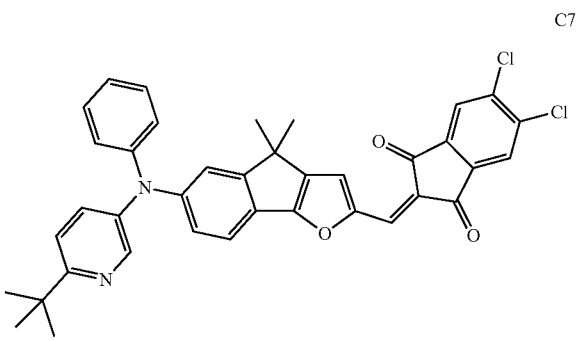
C8
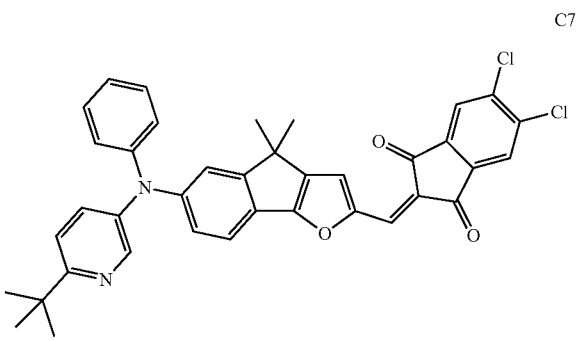
C9
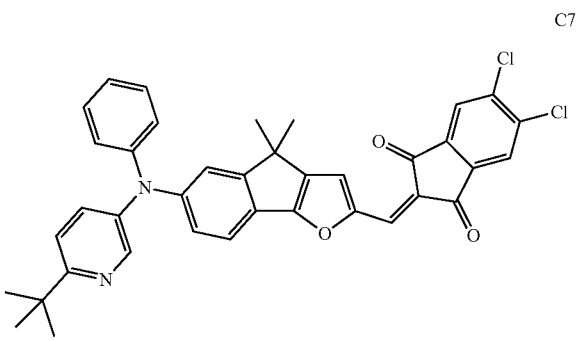
C10
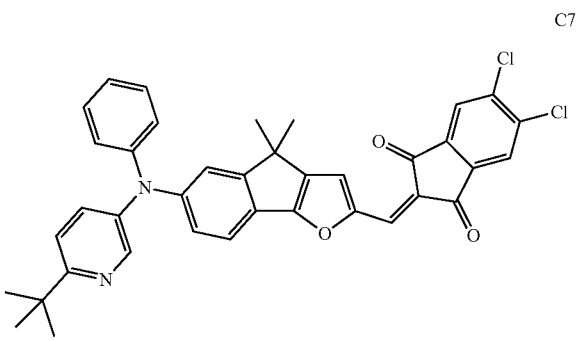

-continued
C11
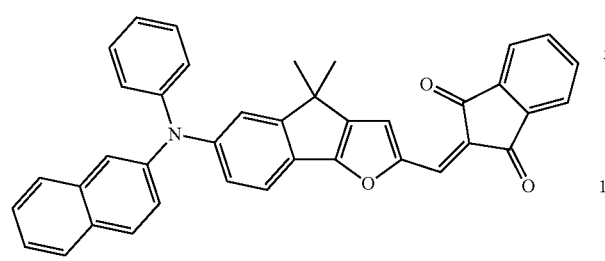
C12
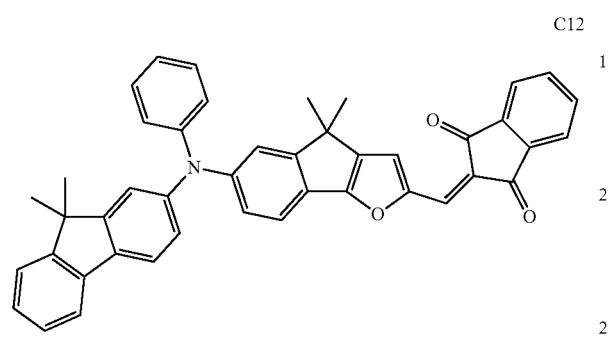
C13
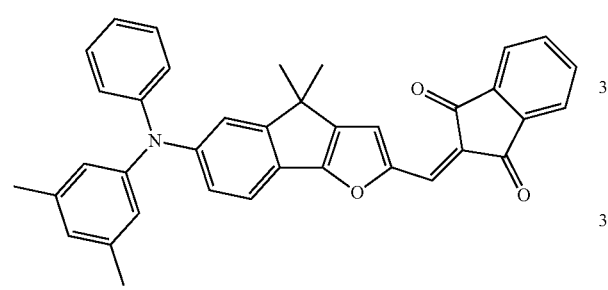
C14
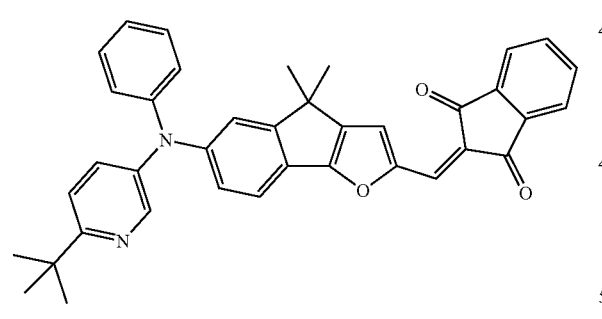
C15
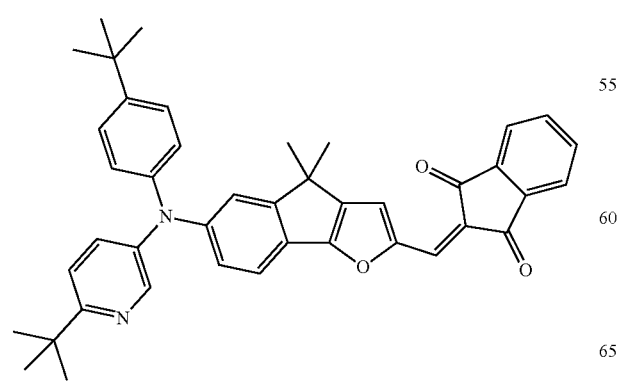
-continued
C16
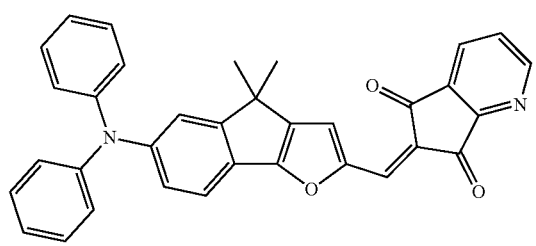
C17
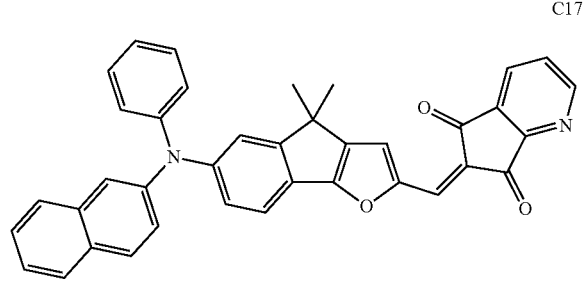
C18
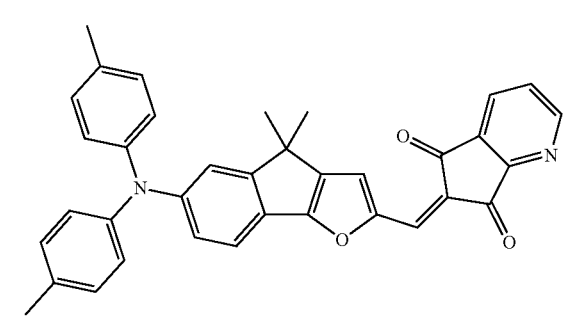
C19
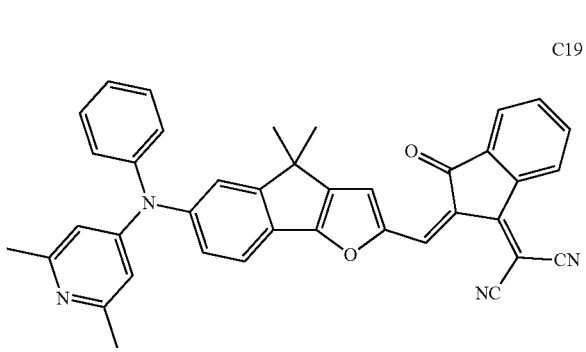
C20

-continued
C21
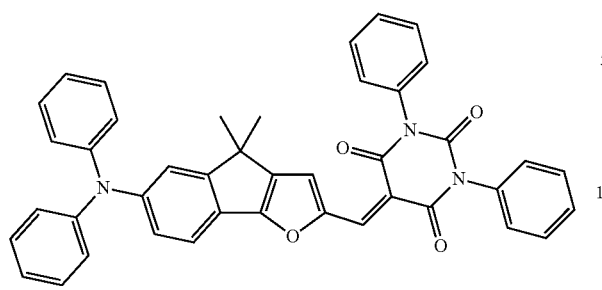
C22
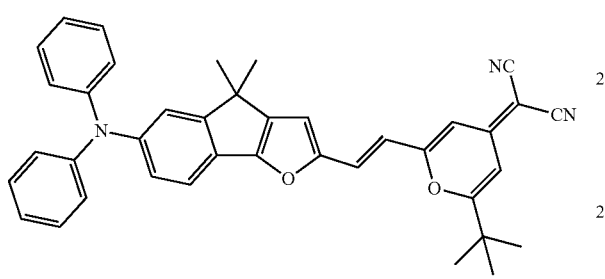
C23
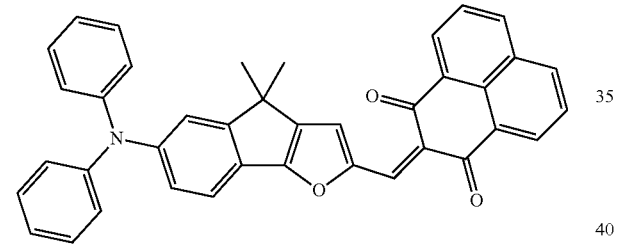
C24
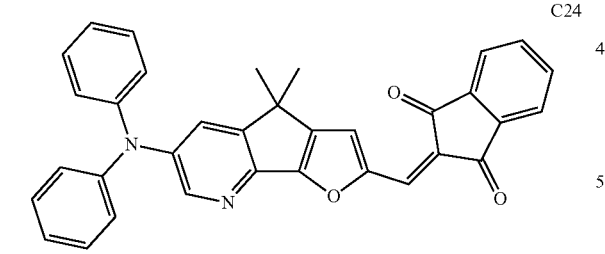
[Chem. 26]
AA1
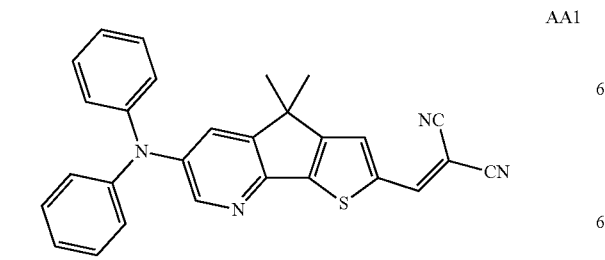
-continued
AA2
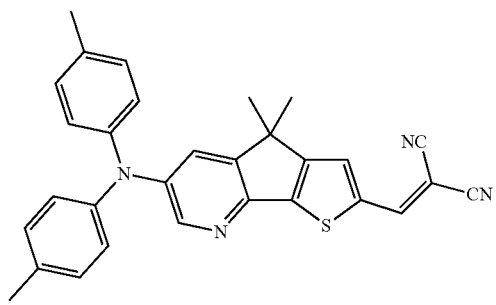
AA3
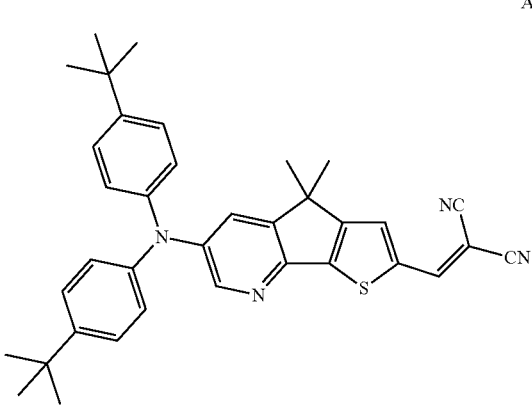
AA4
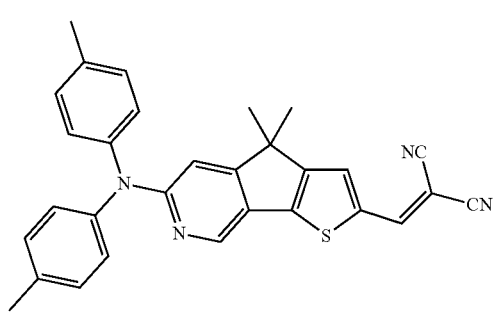
AA5
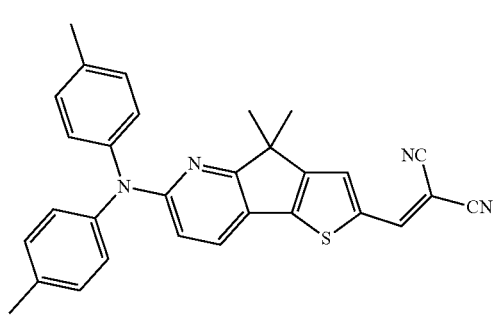

51
-continued
AA6
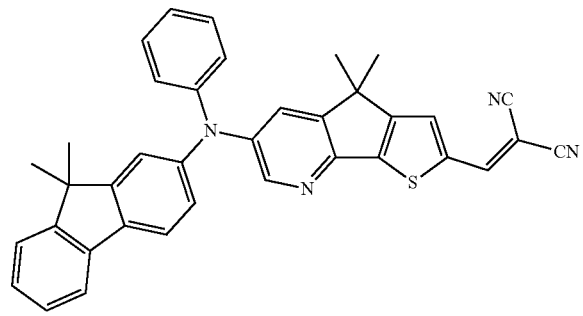
AA7
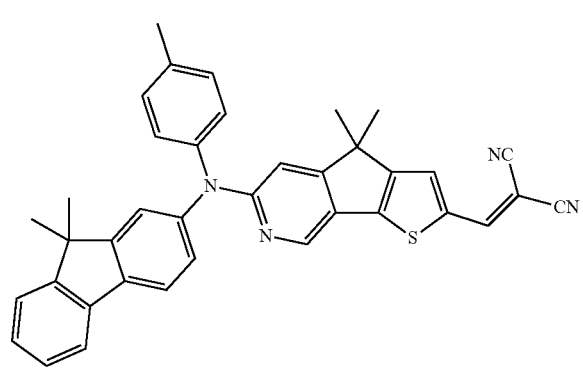
AA8
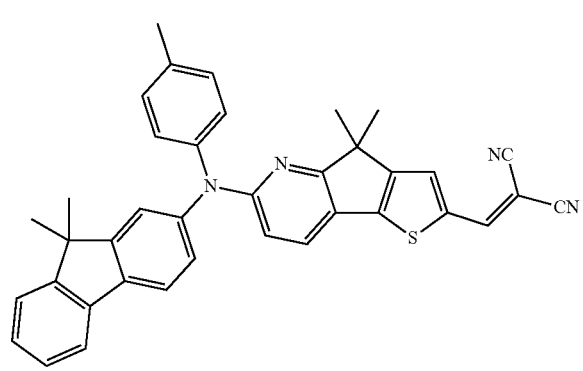
AA9
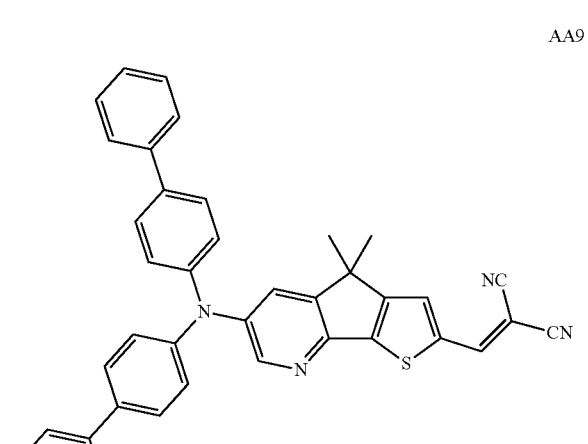
52
-continued
AA10
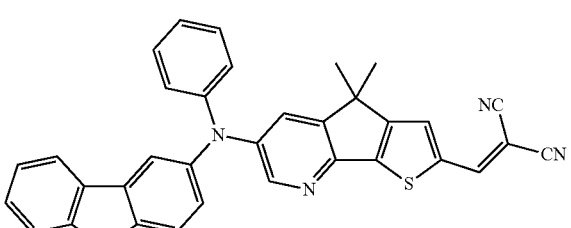
AA11
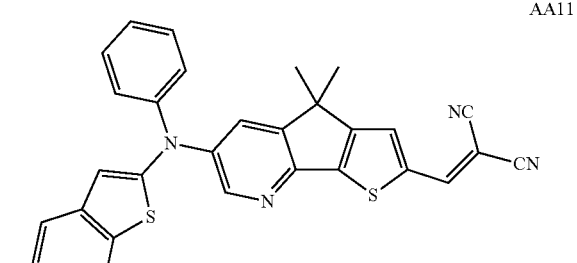
AA12
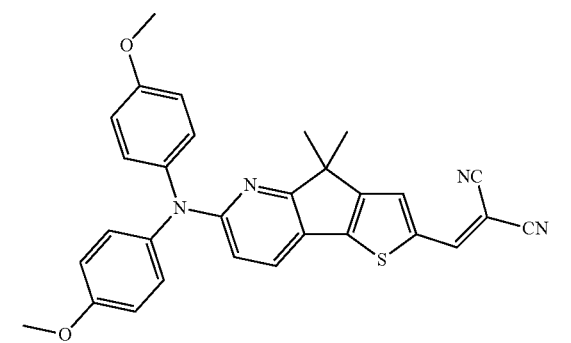
AA13
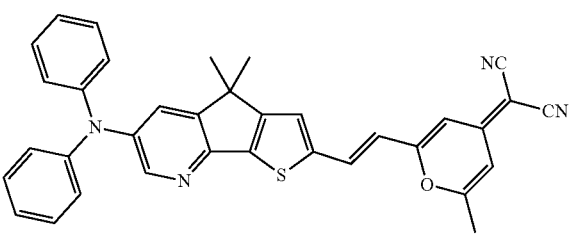
AA14
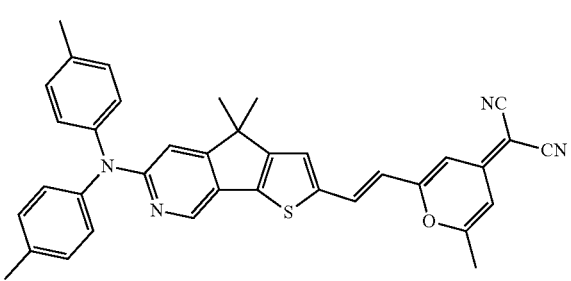

AA15

AA16

AA17

AA18

[Chem. 27]

AA19

AA20

AA21

AA22

AA23

AA24
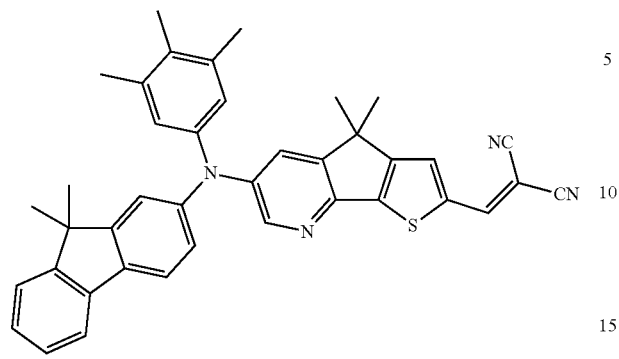
AA28
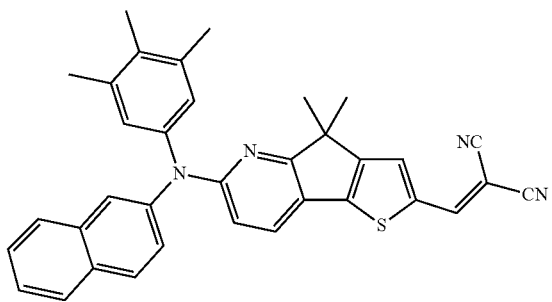
AA25
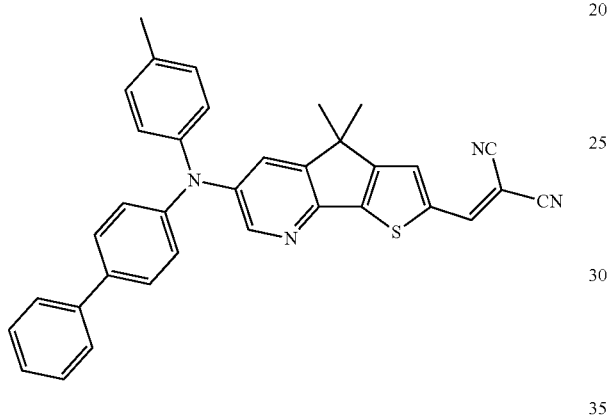
AA29
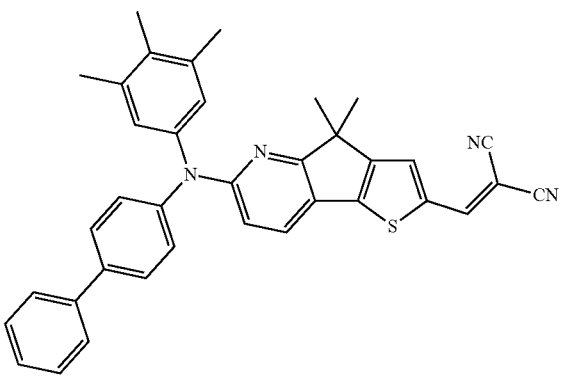
AA26
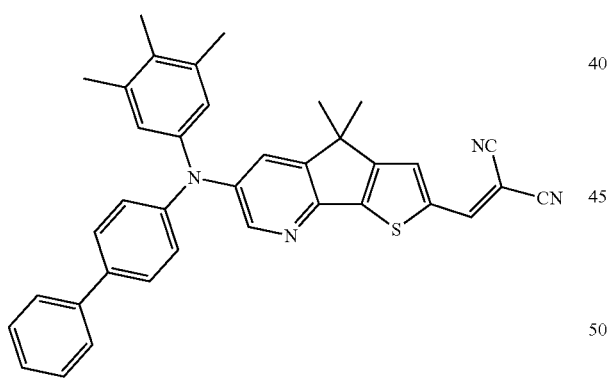
AA30
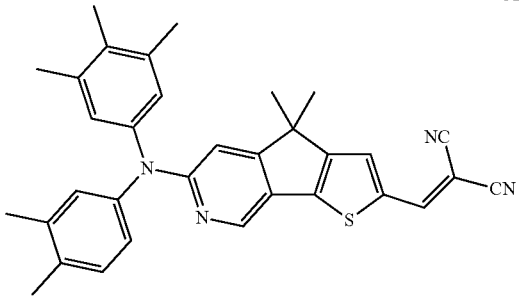
AA27
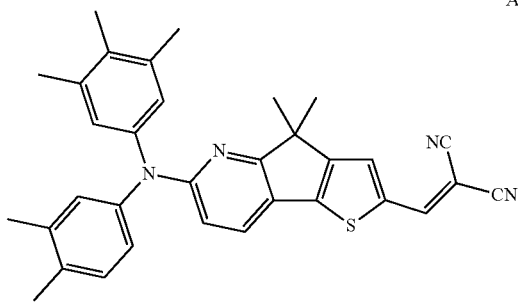
AA31
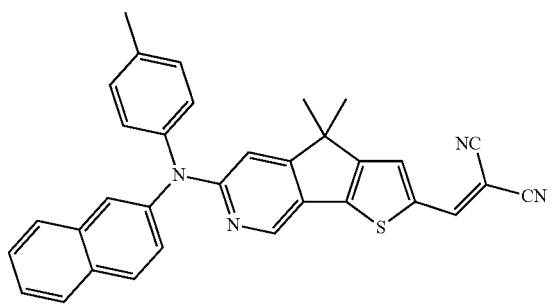

[Chem. 28]
AA32
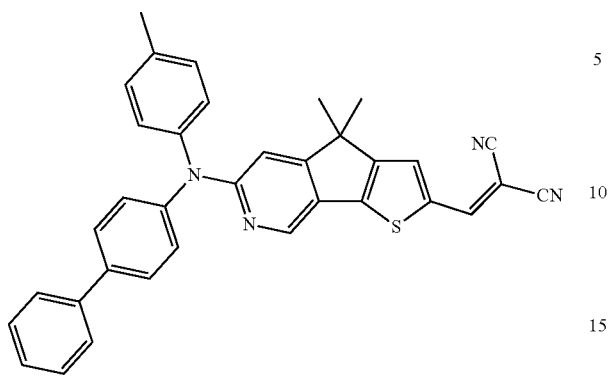
AA33
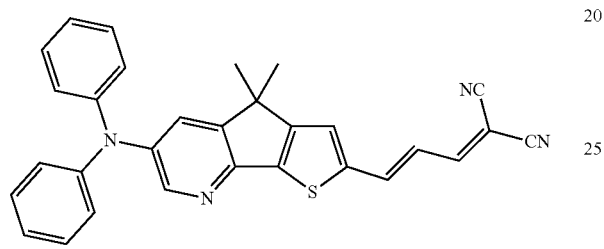
AA34
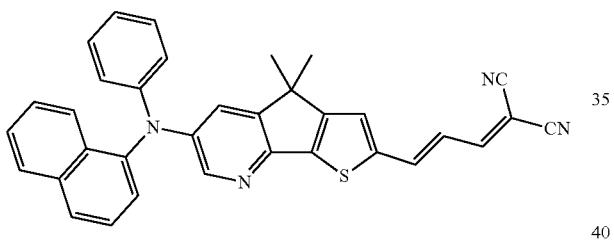
AA35
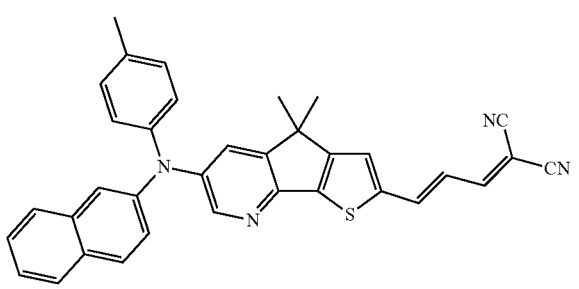
AA36
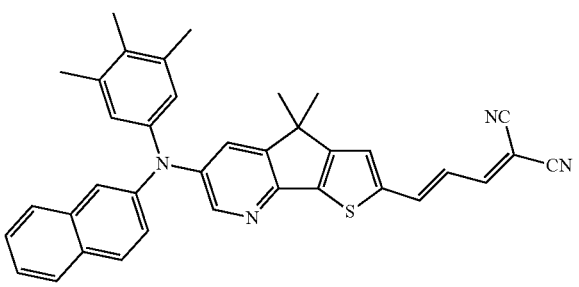
BB1
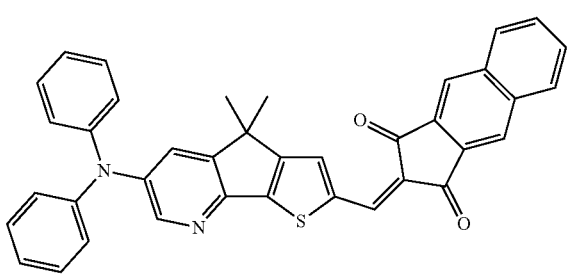
BB2
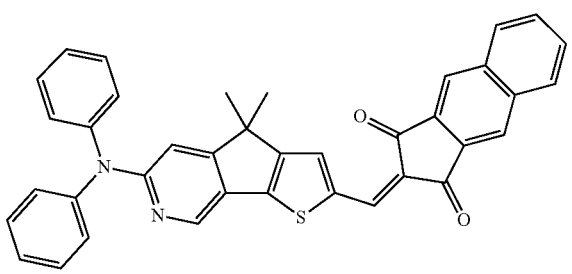
BB3
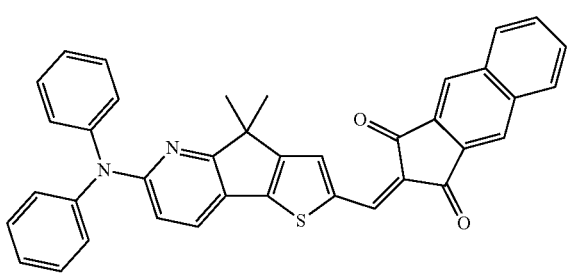
BB4
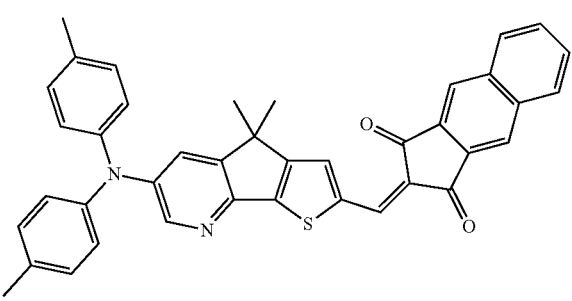
BB5
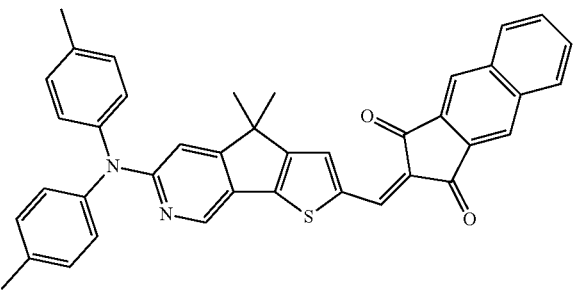

BB6
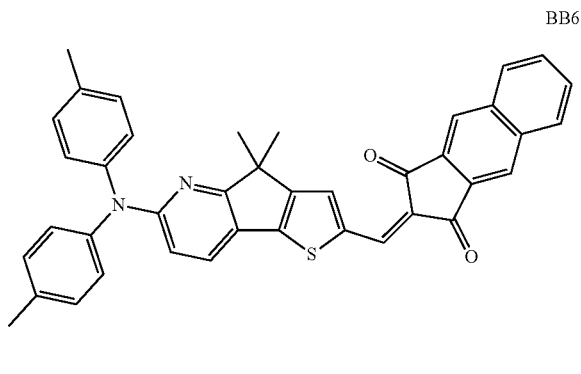
BB10
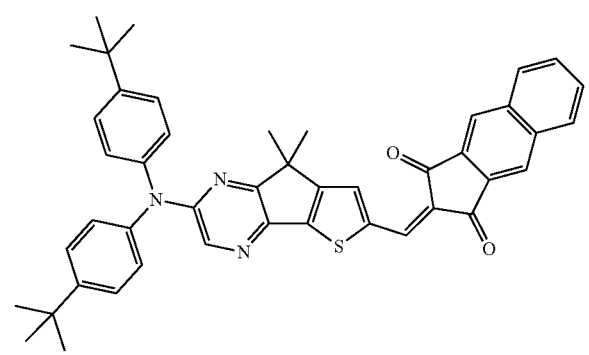
BB7
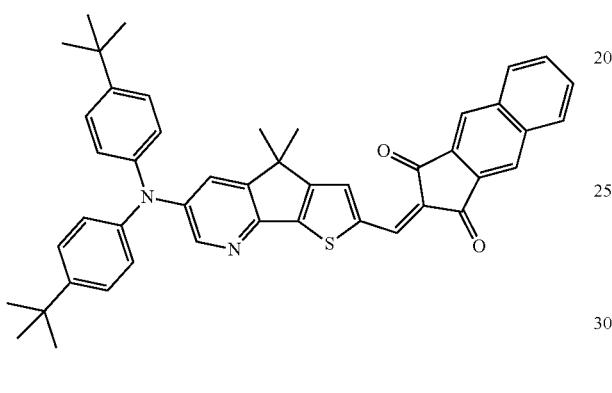
BB11
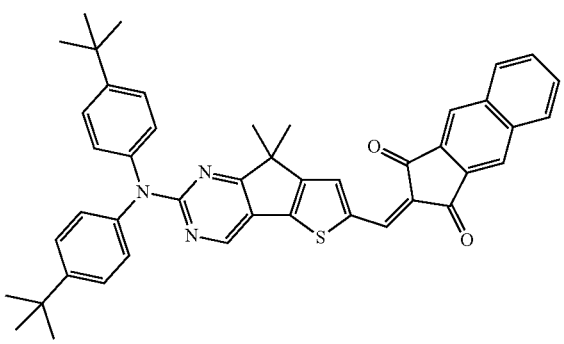
BB8
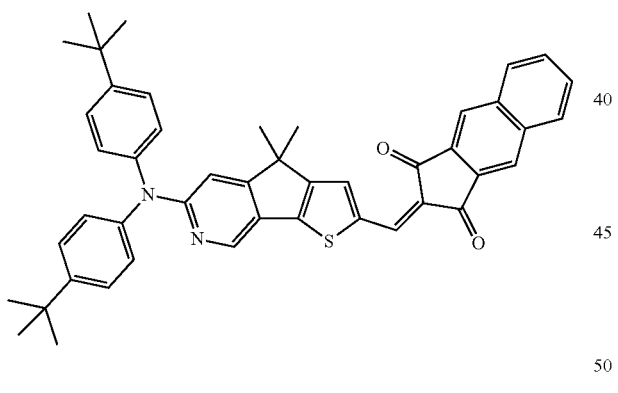
BB12
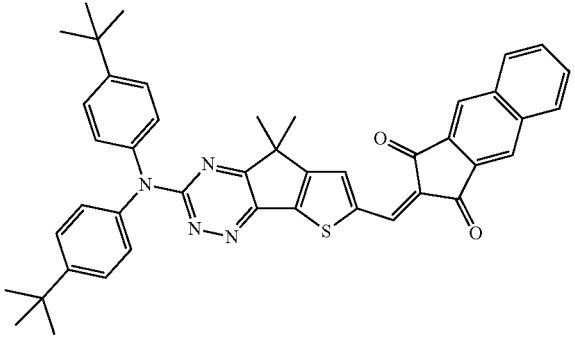
BB9
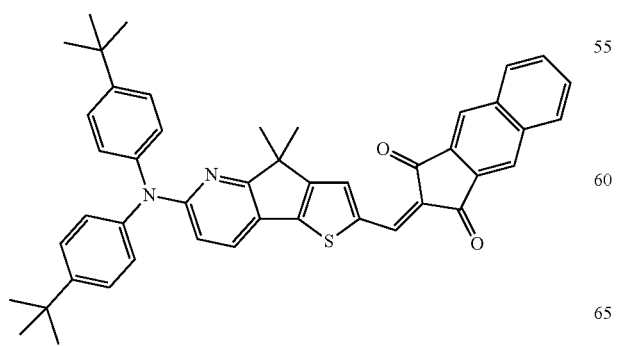
BB13
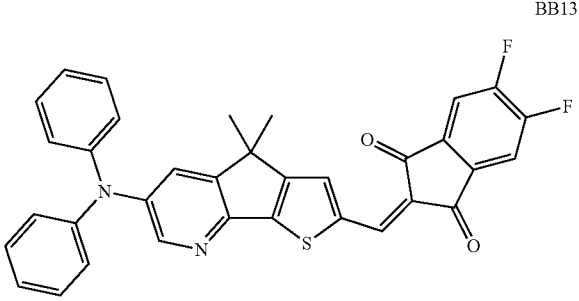

BB14
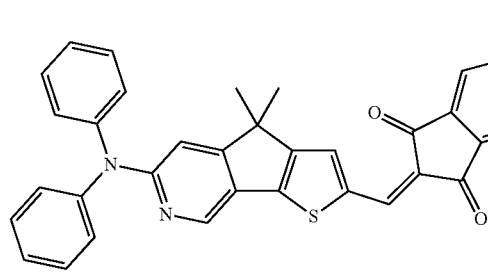
BB15
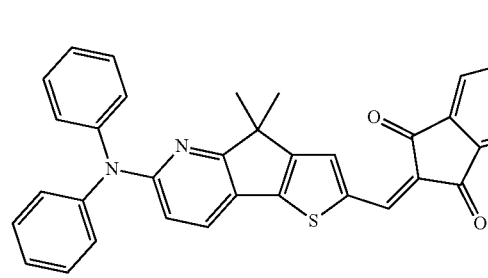
BB16
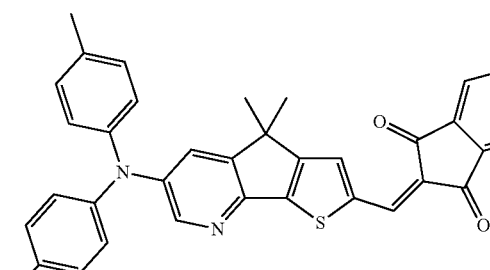
BB17
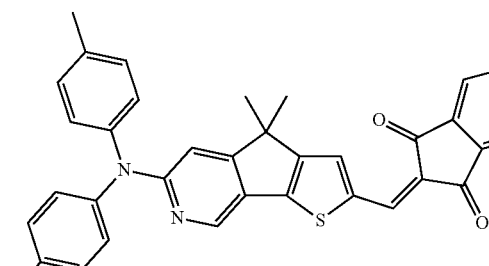
BB18
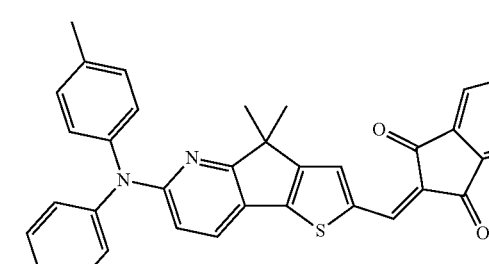
BB19
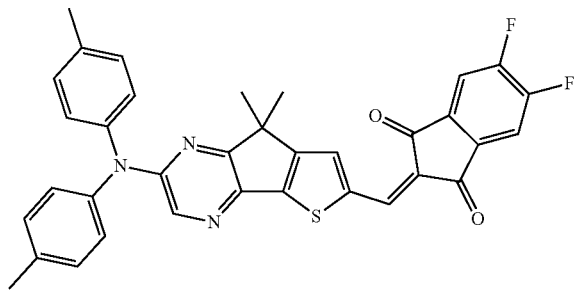
BB20
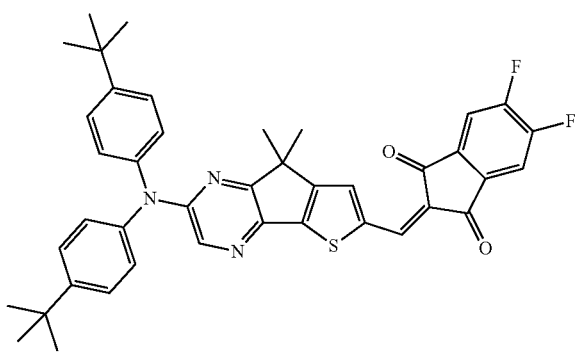
BB21
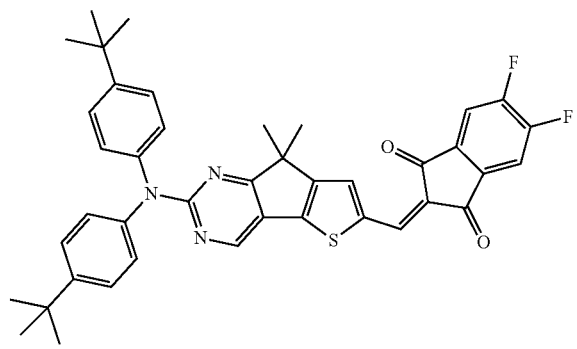
BB22
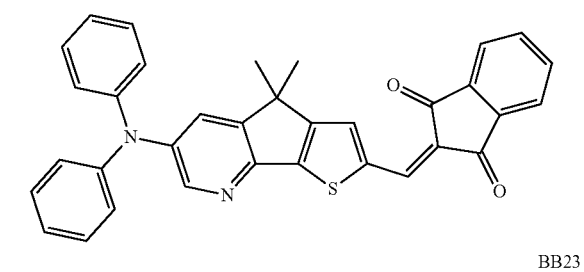
BB23
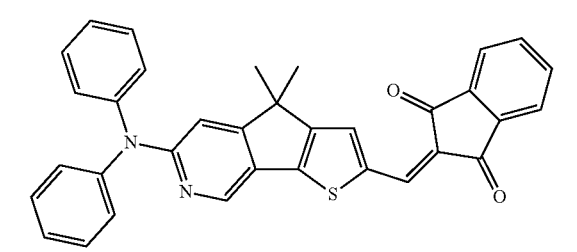

-continued
BB24
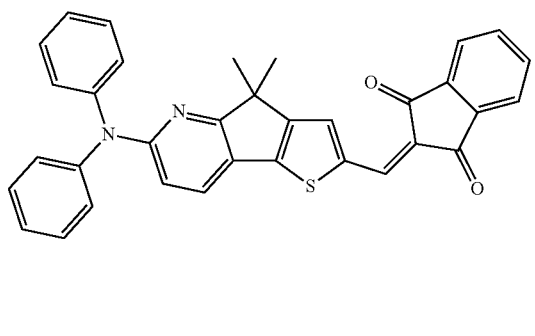
[Chem. 29]
BB25
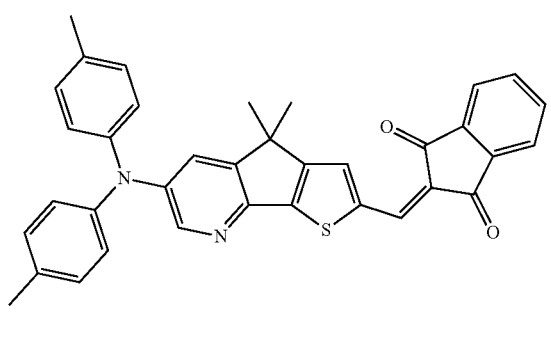
BB26
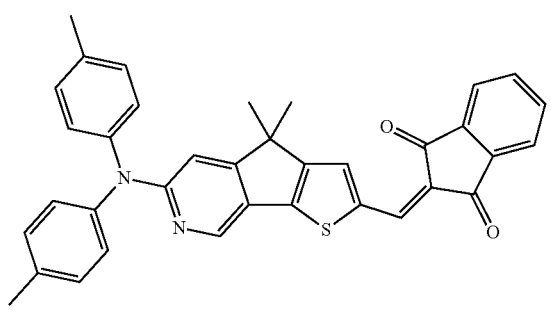
BB27
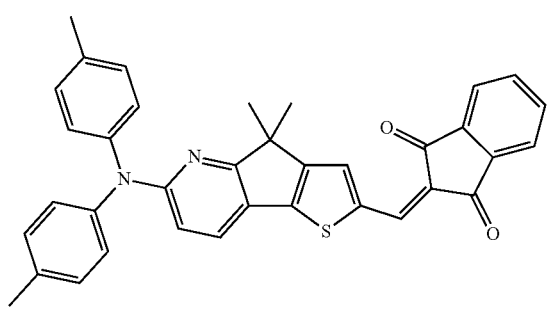
BB28
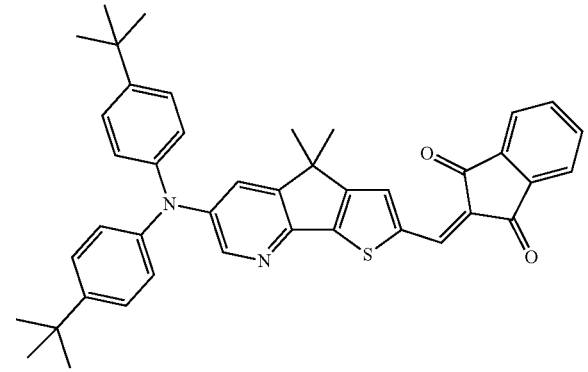
BB29
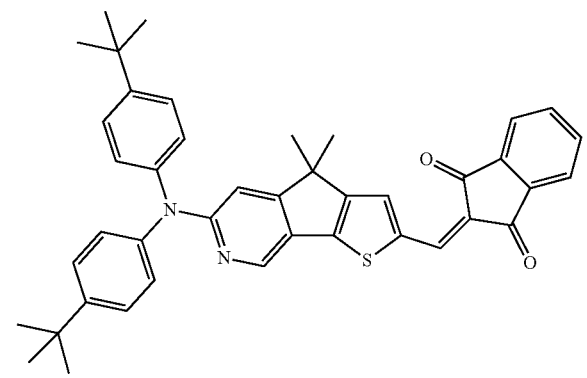
BB30
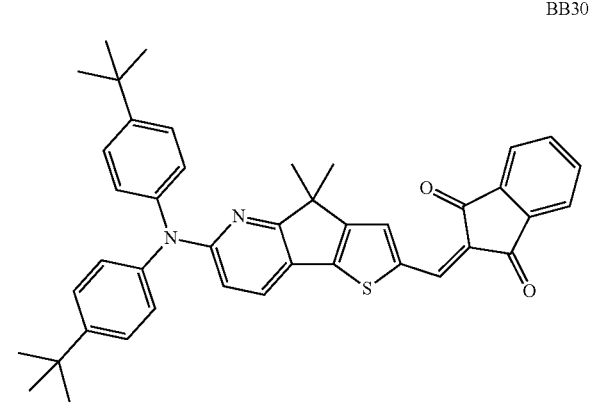
BB1
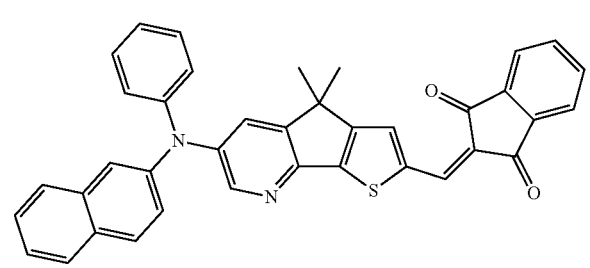

BB32
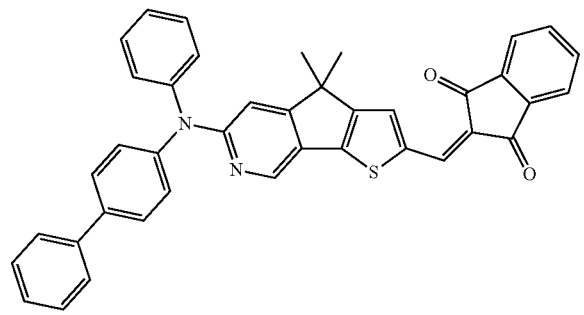
BB33
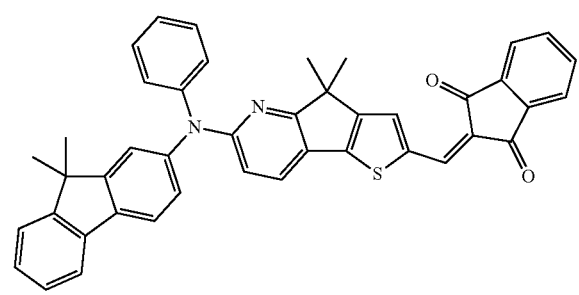
BB34
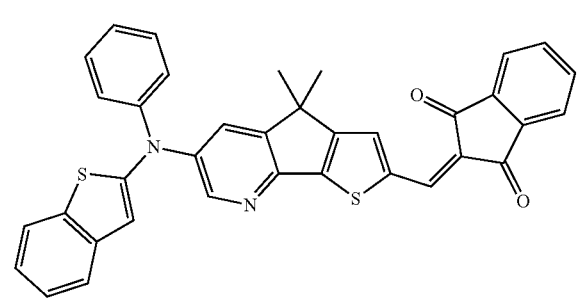
BB35
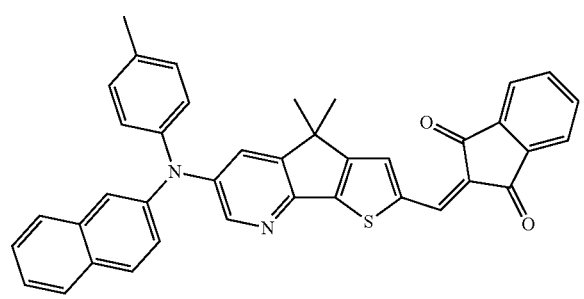
BB36
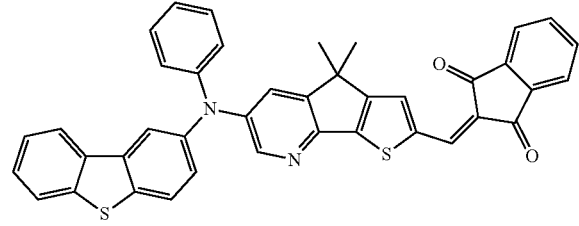
BB37
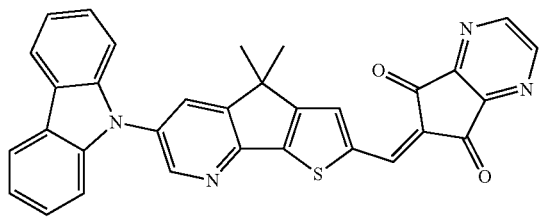
BB38
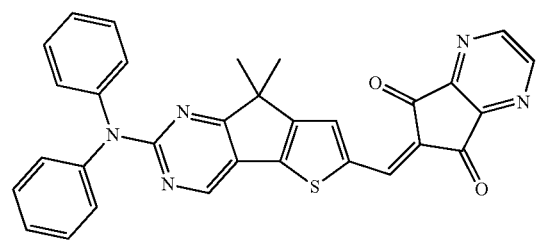
BB39
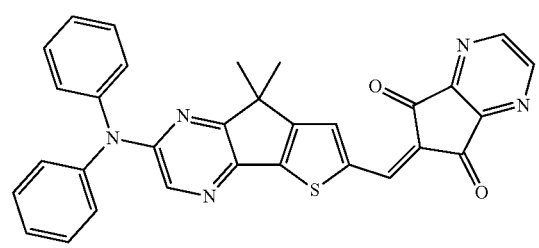
BB40
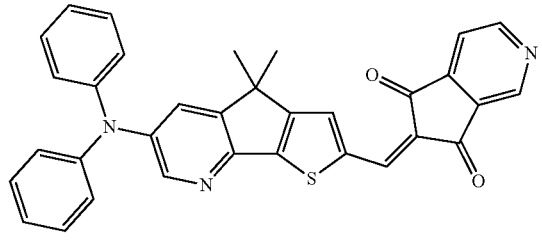
BB41
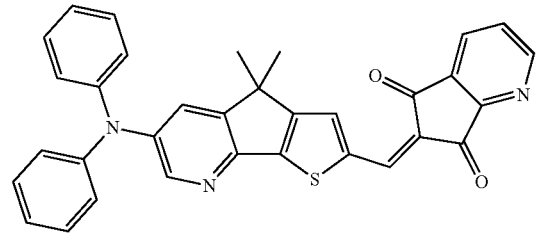
BB42
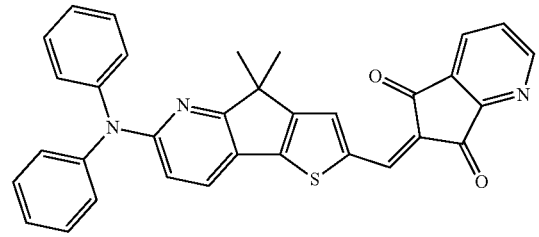

-continued
BB43
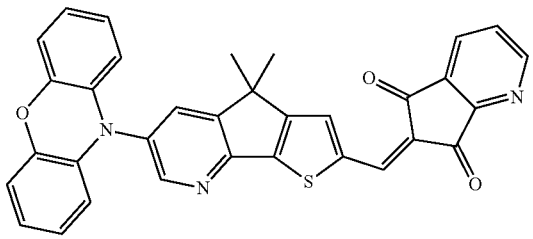
BB44
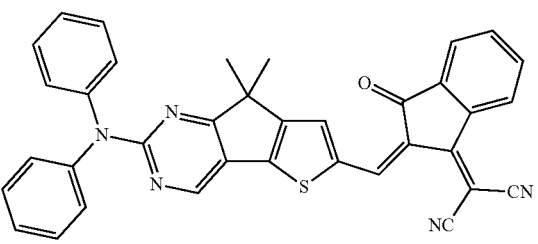
BB45
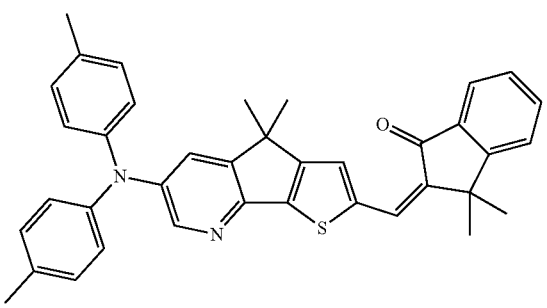
BB46
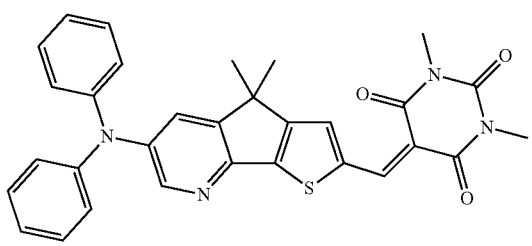
BB47
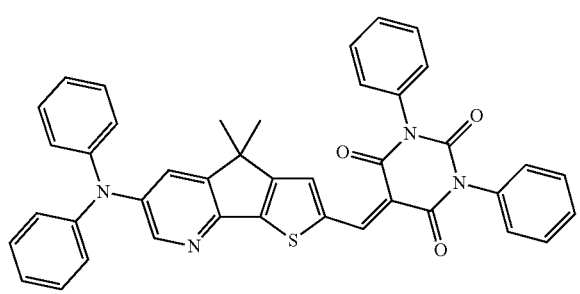
-continued
BB48
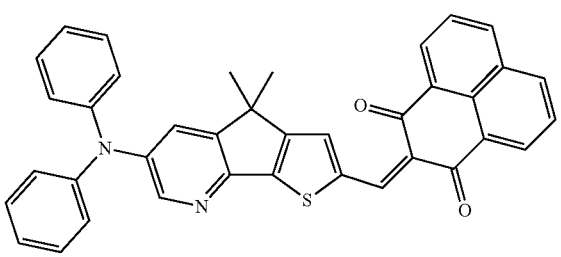
[Chem. 30]
BB49
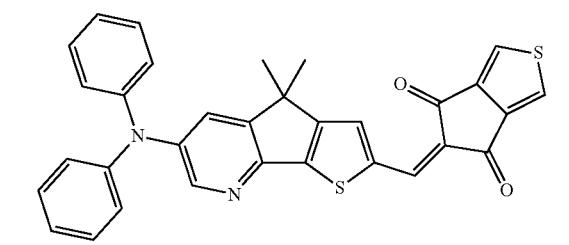
BB50
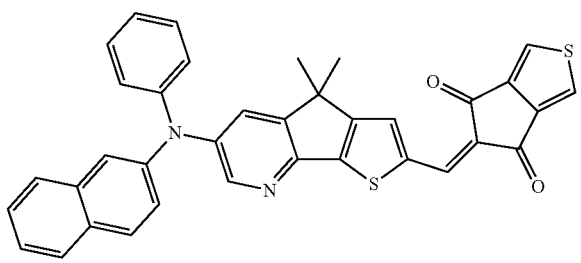
BB51
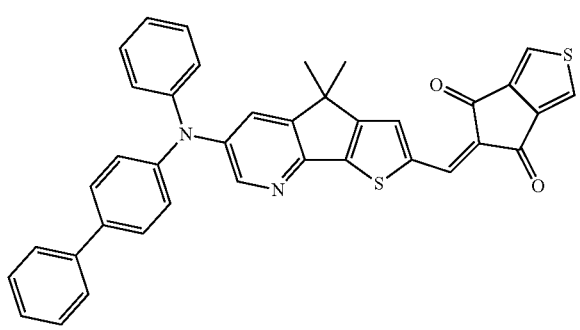
BB52
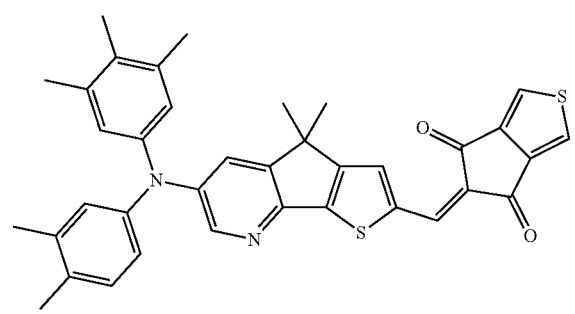

BB53
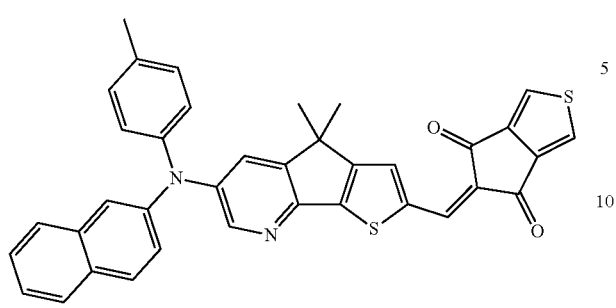
BB58
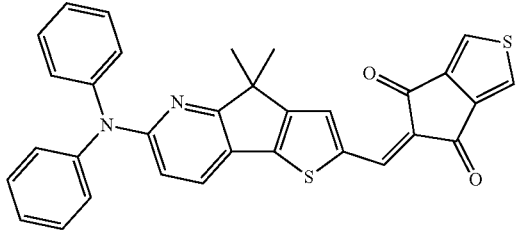
BB54
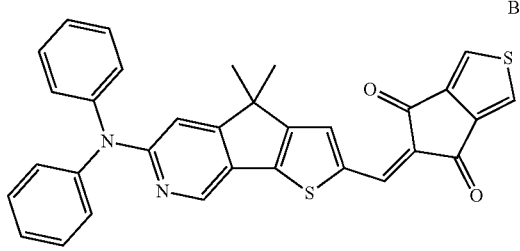
BB59
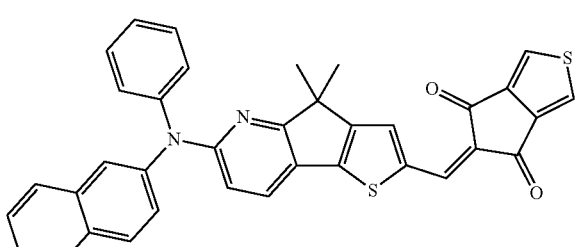
BB55
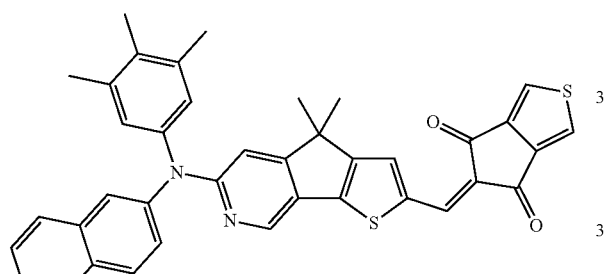
BB60
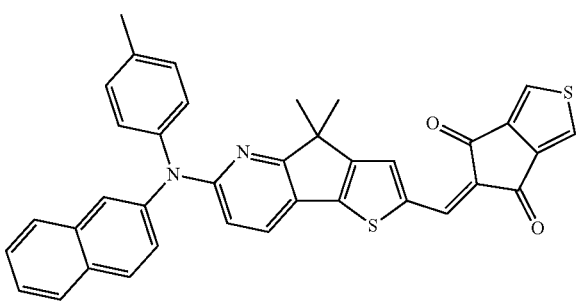
BB56
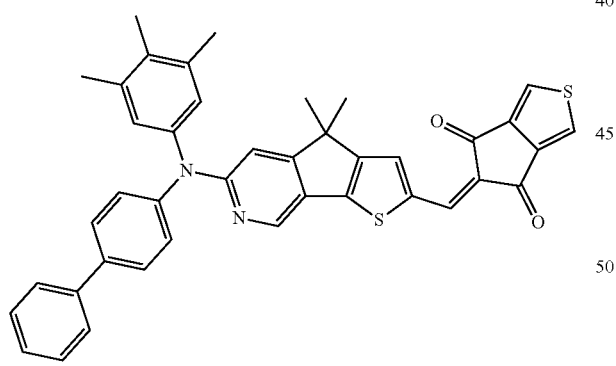
BB61
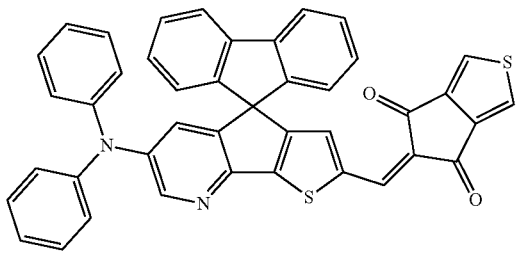
BB57
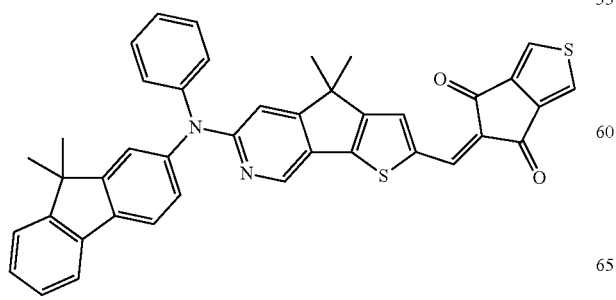
BB62
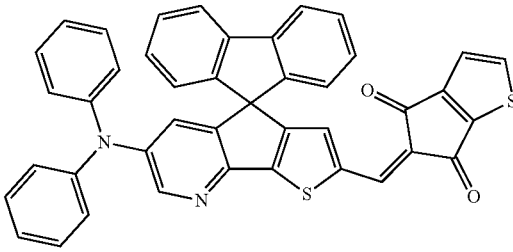

-continued
BB63
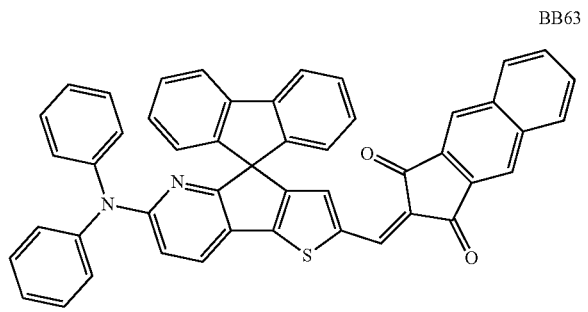
BB64
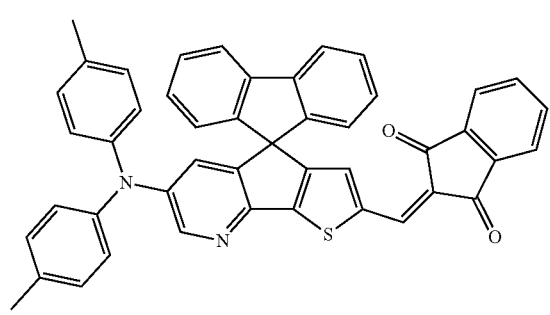
BB65
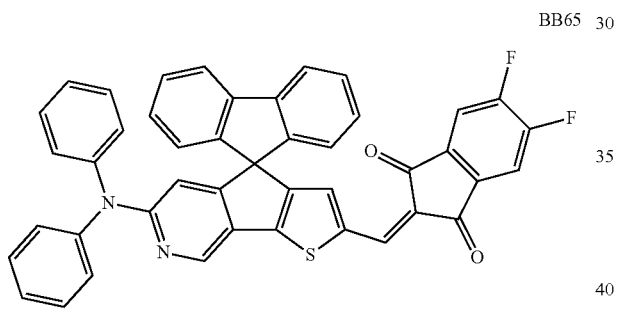
BB66
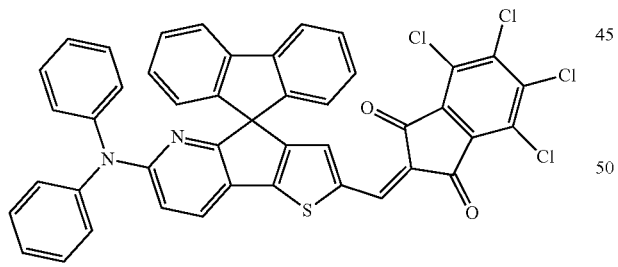
BB67
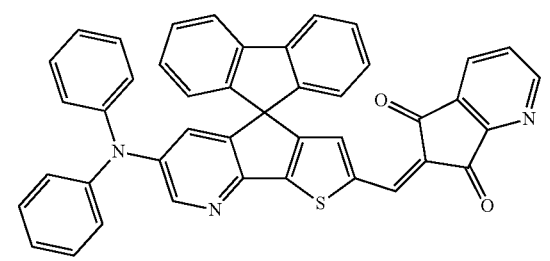
-continued
BB68
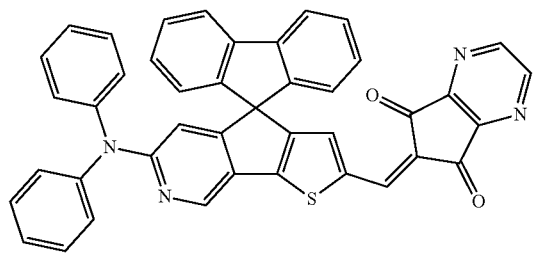
BB69
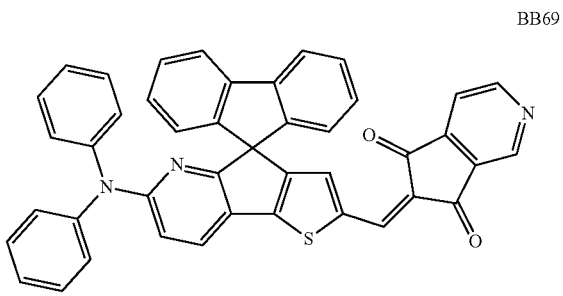
[Chem. 31]
CC1
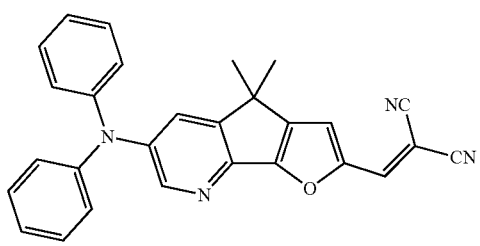
CC2
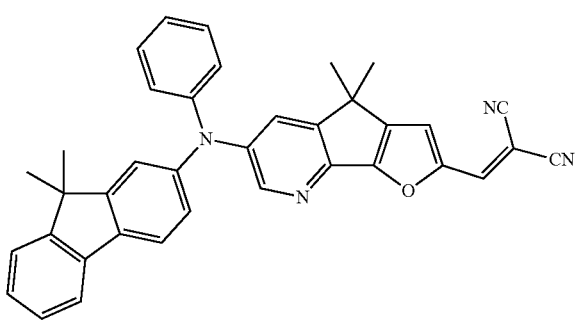
CC3
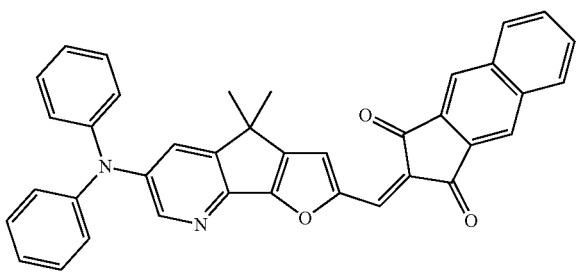

-continued
CC4
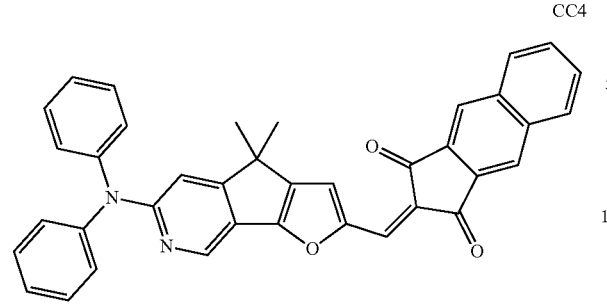
CC5
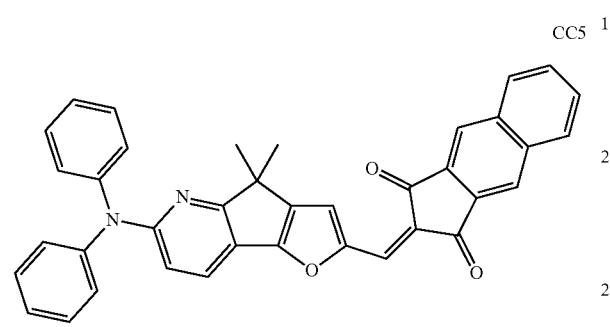
CC6
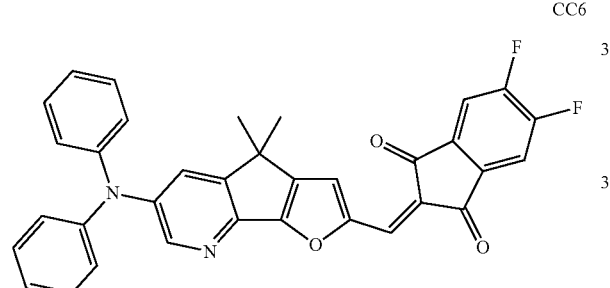
CC7
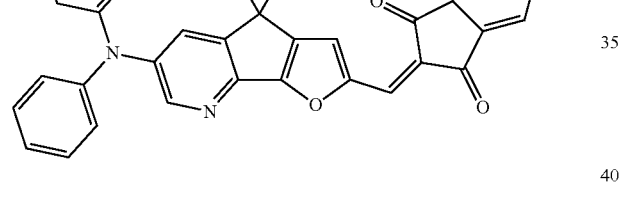
CC8
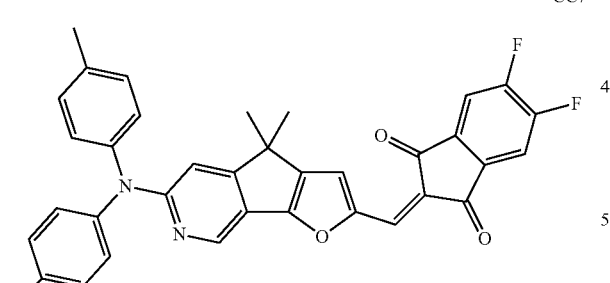
-continued
CC9
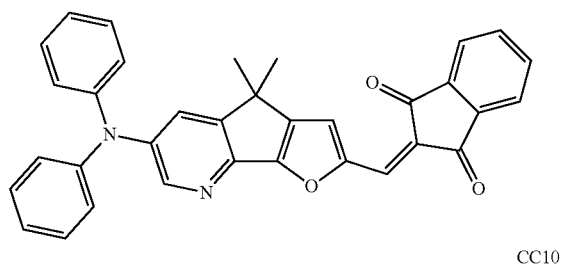
CC10
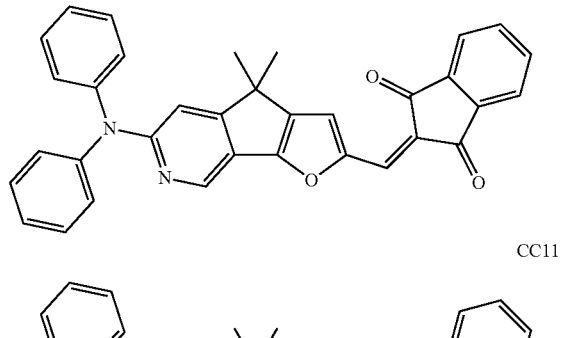
CC11
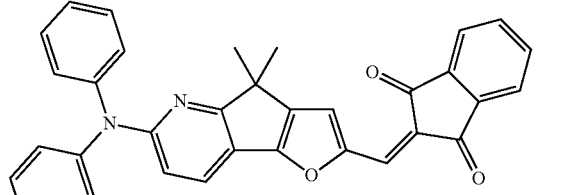
CC12
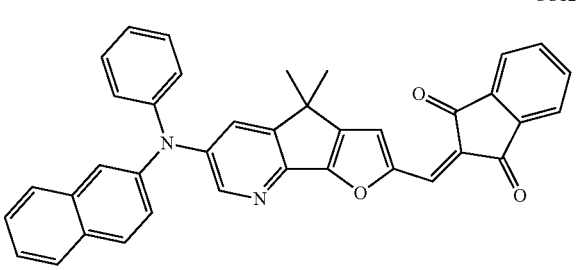
CC13
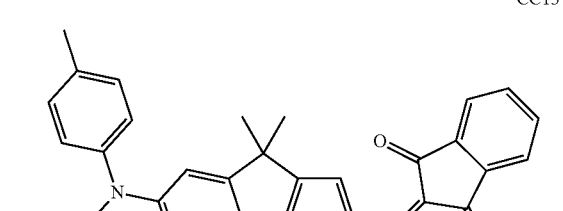
CC14
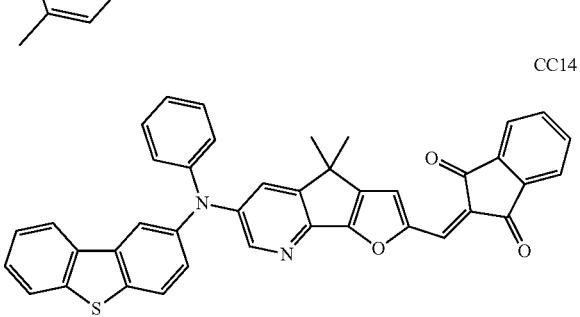

-continued
CC15
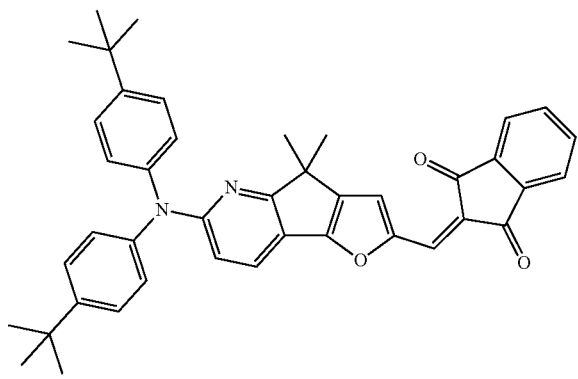
CC16
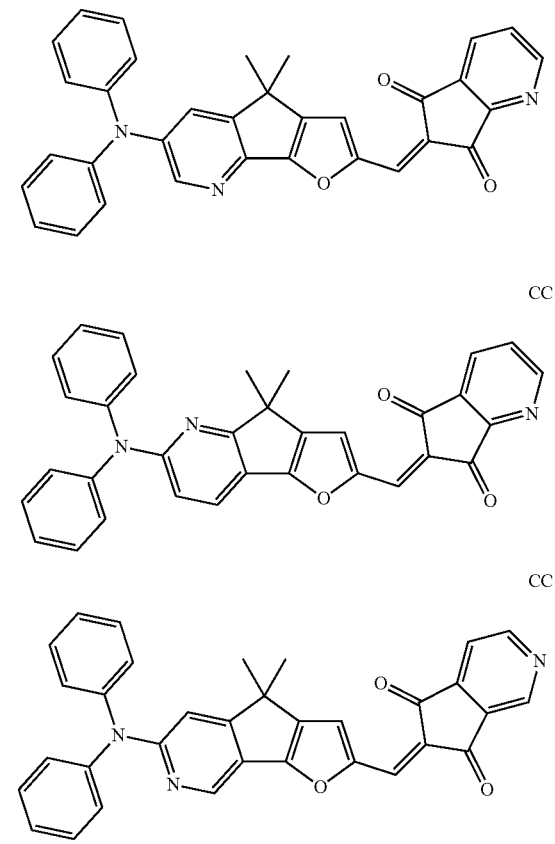
CC20
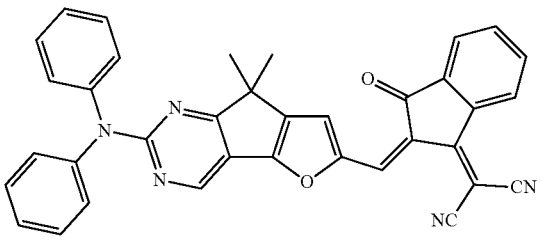
CC21
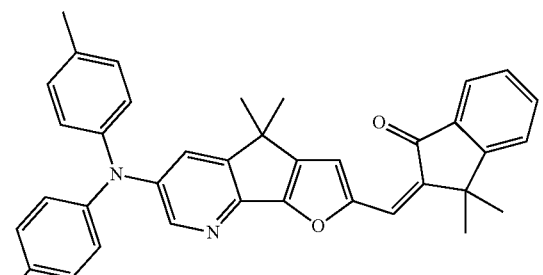
CC22
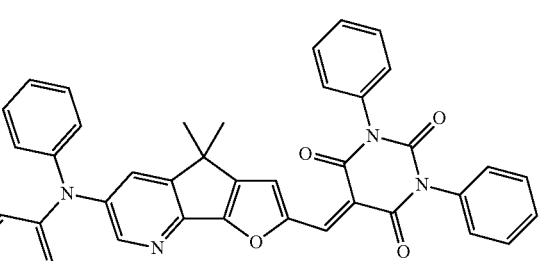
CC23
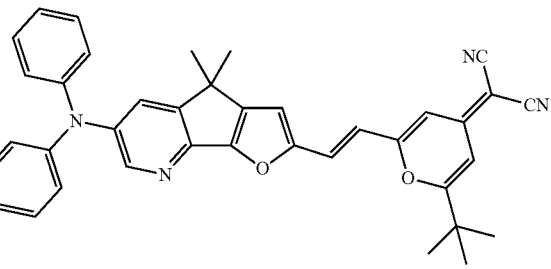
CC24
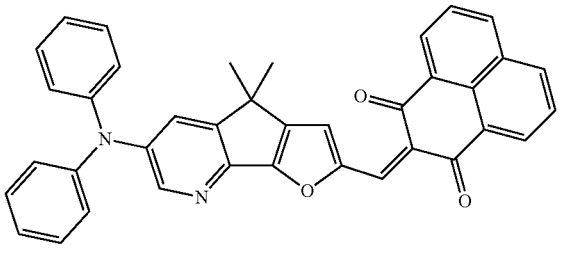
In each of the compounds categorized as group A and group AA among the exemplified compounds, $X_1$ is sulfur, and $R_4$ is represented by general formula [1-1], in general formula [1]. Among groups A and AA, A1 to A17, A21 to A32, AA1 to AA12, and AA19 to A32 are compounds that can be sublimed at low temperatures because of their low molecular weights.

In each of the compounds categorized as group B and group BB among the exemplified compounds, $X_1$ is sulfur, and $R_4$ has at least one carbonyl group, in general formula [1]. That is, these are examples of the compound represented by general formula [2]. Among the compounds according to the present invention, the compounds categorized as groups B and BB have high absorption sensitivities to red light and high photoelectric conversion efficiencies in the red region. Furthermore, the compounds have high melting points and thus have large values of Δtemperature (sublimation temperature–melting point), high thermal stability, and high vapor deposition stability.

Among these, each of exemplified compounds B1 to B39, B49 to B72, BB1 to BB43, and BB49 to BB69 has two carbonyl groups in $R_4$. That is, these compounds are represented by general formula [3]. These exemplified compounds among the compounds categorized as groups B and BB are highly symmetric and thus have high melting points, high thermal stability, and high vapor deposition stability.

The compounds categorized as groups A, B, AA, and BB are each a compound in which $X_1$ in general formula [1] is sulfur. The thiophene ring has high aromaticity and a stable backbone and thus is more preferred. In addition, for example, when the molecules are stacked in a thin film state, the molecules can be regularly arranged by weak intermolecular sulfur-sulfur bonding. This increases the charge mobility in the thin film state to increase the photoelectric conversion efficiency and thus is preferred.

Among the exemplified compounds, compounds categorized as groups C and CC are each a compound in which $X_1$ in general formula [1] is oxygen. Oxygen has a high electronegativity and a small atomic radius, compared with sulfur. Thus, the dipole moment is large from the amino group toward $R_4$. Thus, these compounds have high molar extinction coefficients than compounds in which $X_1$ is sulfur.

Among these compounds categorized as groups C and CC, exemplified compounds C3 to C18 and CC3 to CC19 each have two carbonyl groups in the electron-withdrawing group. That is, these compounds are represented by general formula [3]. These exemplified compounds are highly symmetric and thus have high melting points, high thermal stability, and high vapor deposition stability.

Among the exemplified compounds, the compounds of groups AA, BB, and CC each have a nitrogen-containing hetero ring in the spacer. Each of the compounds has a deep HOMO level due to the effect of the nitrogen-containing hetero ring, which is a π-electron-deficient system, compared with when no nitrogen atom is present. The compound having a deep HOMO level is preferred because the compound is highly effective in suppressing dark current when used for a photoelectric conversion element. In general formula [1], if at least one of $Y_1$ to $Y_3$ is a nitrogen atom, the compounds have deep HOMO levels, regardless of the number and positions, and have molar extinction coefficients as high as groups A, B, and C.

Among the exemplified compounds of groups AA, BB, and CC, the compounds categorized as groups AA1 to AA3, AA6, AA9 to AA11, AA13, AA16, AA10 to AA26, AA33 to AA36, BB1, BB4, BB7, BB13, BB16, BB22, B25, BB28, BB31, BB34 to BB37, BB40, BB41, BB43, BB45 to 48, BB49 to BB53, BB61 to BB62, BB64, BB67, CC1 to CC3, CC6, CC9, CC12 to 14, CC17, and CC21 to 24 are each a compound in which, in general formula [1], $Y_3$ is a nitrogen atom, and $Y_1$ and $Y_2$ are each a carbon. Among groups AA, BB, and CC, these compounds have better absorption sensitivity in the red region.

Among the exemplified compounds of groups AA, BB, and CC, compounds AA4, AA5, AA7, AA8, AA12, AA14, AA15, AA17, AA18, AA27 to AA32, BB2, BB3, BB5, BB6, BB8, BB9, BB14, BB15, BB17, BB18, BB23, BB24, BB26, BB27, BB29, BB30, BB32, BB33, BB42, BB54 to BB60, BB63, BB65 to BB66, BB68, BB69, CC4, CC5, CC7, CC8, CC10, CC11, CC15, CC18, and CC19 are each a compound in which one of $Y_1$ and $Y_2$ in general formula [1] is a nitrogen atom. The nitrogen atom in the spacer is located next to a substituent position to which the amino group is attached, thereby increasing the dipole moment in the molecule. Thus, these compounds have high molar extinction coefficients among the compounds according to the present invention.

Among the exemplified compounds of groups AA, BB, and CC, compounds BB10 to 12, BB19 to BB21, BB38, BB39, BB44, CC16, and CC20 are each a compound in which two or more of $Y_1$ and $Y_3$ in general formula [1] are each a nitrogen atom. The hetero rings each containing two or more nitrogen atoms are systems more deficient in electrons, compared with the hetero ring containing one nitrogen atom. Thus, these compounds have deep HOMO levels among the compounds according to the present invention.

Among the exemplified compounds, the compounds of groups A, AA, C1, C2, CC1, and CC2 are each a compound in which $R_4$ is represented by general formula [1-1]. These compounds have low molecular weights and can be sublimed at low temperatures among the compounds according to the present invention.

Among the exemplified compounds, the compounds of groups B1 to B9, B49 to B51, BB1 to BB12, BB63, C3, C4, CC3, and CC5 are each a compound in which a benzoindandione derivative is substituted as a substituent attached to the spacer with a vinyl group in general formula [1]. These compounds have high absorption sensitivity in the red region among the compounds according to the present invention. The substituent attached to the spacer is $R_4$.

Among the exemplified compounds, compounds B10 to B39, B52 to B61, BB13 to BB43, BB64 to BB66, C5 to C18, and CC6 to C19 are each a compound in which an indandione derivative is substituted as a substituent attached to the spacer with a vinyl group in general formula [1]. These compounds have good absorption sensitivity in the red region and high vapor deposition stability among the compounds according to the present invention.

Method for Synthesizing Organic Compound According to Present Invention

Next, a method for synthesizing the organic compound according to the present invention will be described below.

An indenochalcogenophene backbone, which is a spacer moiety of the organic compound according to the present invention, can be synthesized according to, for example, a synthetic scheme represented by formula [8].

[Chem. 32]

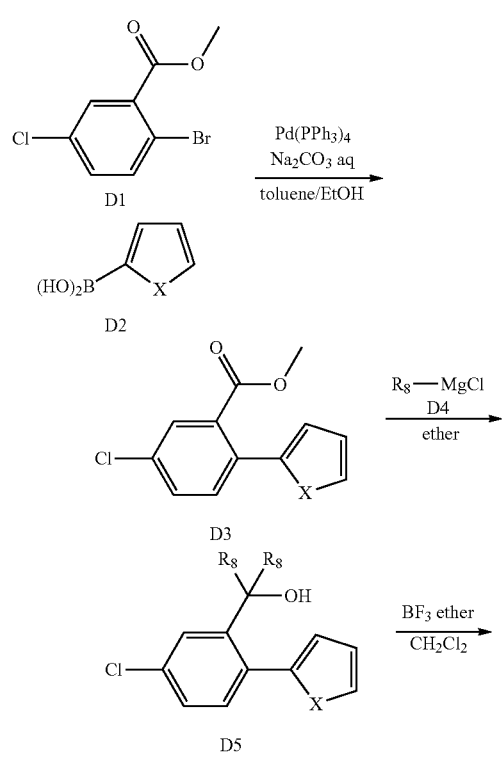

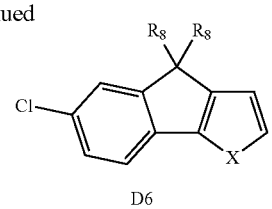

Specifically, the backbone is synthesized by sequentially performing reactions (1) to (3) below.

(1) D3 can be synthesized by a cross-coupling reaction of a chalcogenophene-boron compound (D2) with D1 in the presence of a Pd catalyst. When D2 is 2-thiopheneboronic acid, a compound in which $X_1$ is sulfur can be synthesized. When D2 is 2-furanylboronic acid, a compound in which $X_1$ is oxygen can be synthesized.

(2) D5 can be synthesized by subjecting D3 to a nucleophilic addition reaction to carbonyl with a Grignard reagent (D4). Regarding D4, when $R_4$ is an alkyl group, the synthesis can be similarly performed with a corresponding Grignard reagent. In the case of substitution with fluorine, for example, the synthesis can be performed using thionyl chloride and pyridine as reagents.

(3) D6 can be synthesized by subjecting D5 to an intramolecular cyclization reaction with a Lewis acid or an acid.

An exemplified compound according to the present invention can be synthesized according to a synthetic scheme represented by formula [9] with the basic backbone (D6). Various exemplified compounds can be synthesized by changing D6, $Ar_1$, and $Ar_2$. Table 5 presents the specific examples.

[Chem. 33]

[9]

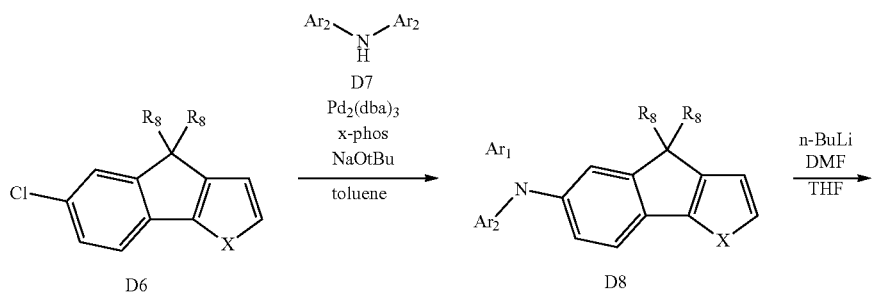

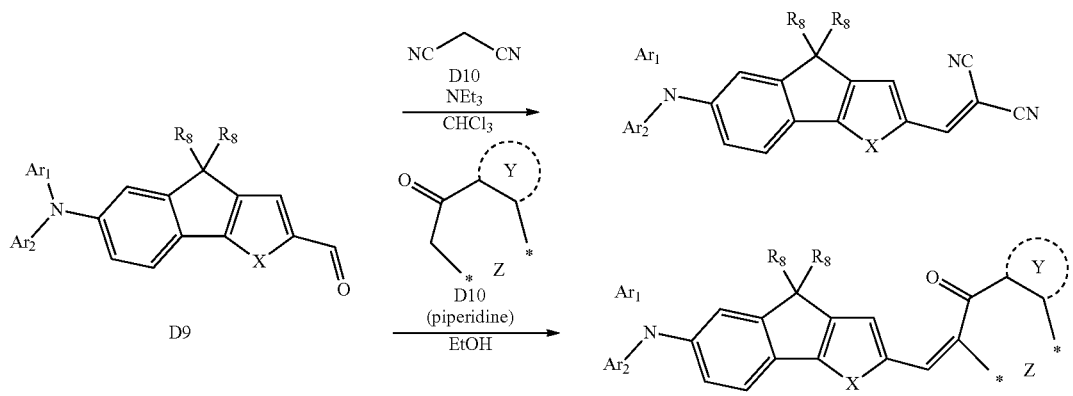

Specifically, the synthesis is performed by sequentially performing reactions (1) to (3) below.

(1) D8 can be synthesized by a cross-coupling reaction of an indenochalcogenophene backbone (D6) with an amine (D7) in the presence of a Pd catalyst.

(2) D9 can be synthesized by a formylation reaction of D8 with n-butyllithium.

(3) An exemplified compound can be synthesized by the Knoevenagel condensation of D9 with D10.

The spacer backbone of the nitrogen-containing organic compound according to the present invention can be synthesized according to, for example, a synthetic scheme represented by formula [10].

[Chem. 34]

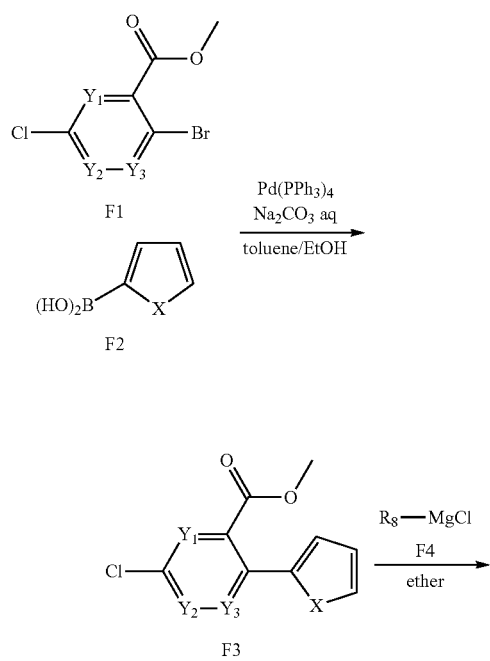

[10]

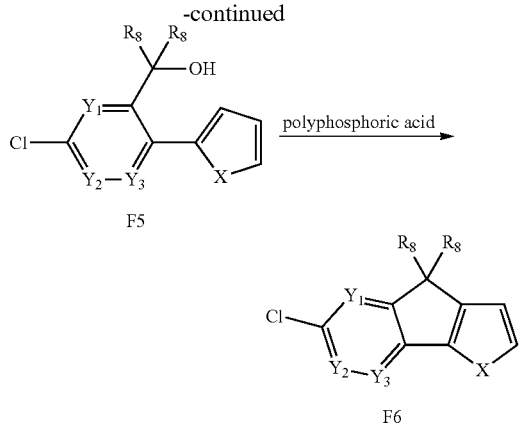

Specifically, the synthesis is performed by sequentially performing reactions (1) to (3) below.

(1) F3 can be synthesized by a cross-coupling reaction of a chalcogenophene-boron compound (F2) with F1 in the presence of a Pd catalyst. When F1 is a pyridine ring, a pyrimidine ring, a pyrazine ring, or a triazine ring, a compound corresponding thereto can be synthesized. When F2 is 2-thiopheneboronic acid, a compound in which X is sulfur can be synthesized. When F2 is 2-furanylboronic acid, a compound in which X is oxygen can be synthesized.

(2) F5 can be synthesized by subjecting F3 to a nucleophilic addition reaction to carbonyl with a Grignard reagent (F4). Regarding F4, when $R_4$ is an alkyl group, the synthesis can be similarly performed with a corresponding Grignard reagent. In the case of substitution with fluorine, for example, the synthesis can be performed using thionyl chloride and pyridine as reagents.

(3) F6 can be synthesized by subjecting F5 to an intramolecular cyclization reaction with a Lewis acid or an acid.

An exemplified compound according to the present invention can be synthesized according to a synthetic scheme represented by formula [11] with the basic backbone (F6). Various exemplified compounds can be synthesized by changing F6, $Ar_1$, and $Ar_2$. Table 5 presents the specific examples.

[Chem. 35]

[11]

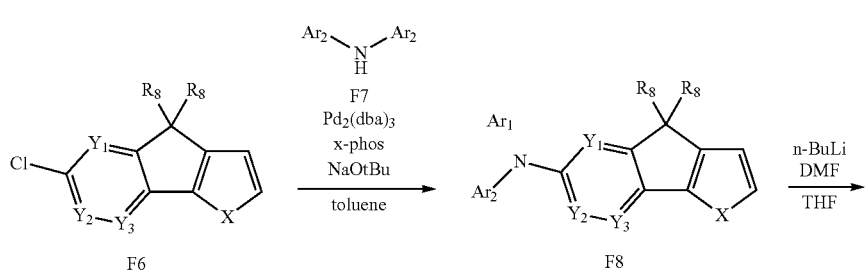

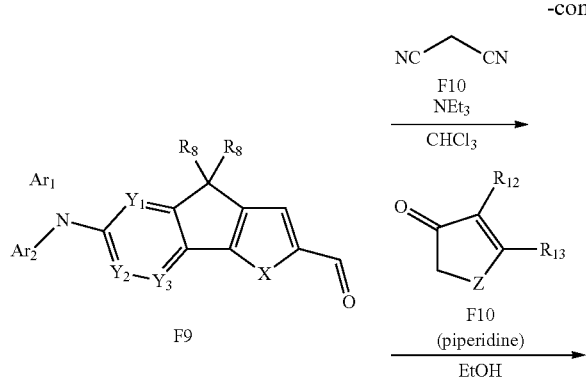

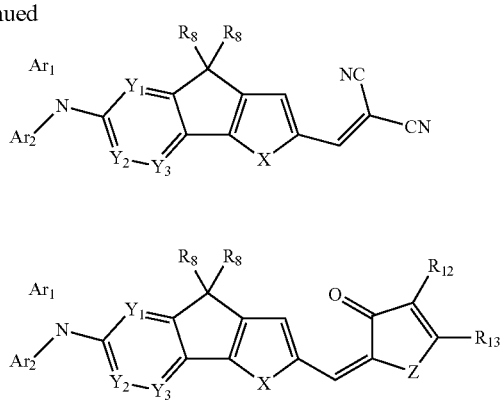

Specifically, the synthesis is performed by sequentially performing reactions (1) to (3) below.

(1) F8 can be synthesized by a cross-coupling reaction of an intermediate (F6) with an amine (F7) in the presence of a Pd catalyst.

(2) F9 can be synthesized by a formylation reaction of F8 with n-butyllithium.

(3) An exemplified compound can be synthesized by the Knoevenagel condensation of F9 with F10. Similarly, an exemplified compound can also be synthesized by converting F10 into a compound represented by general formula [12]. $R_{50}$ to $R_{60}$ are each independently selected from a hydrogen atom, a halogen atom, an alkyl group, an aryl group, and a heteroaryl group.

[Chem. 36]

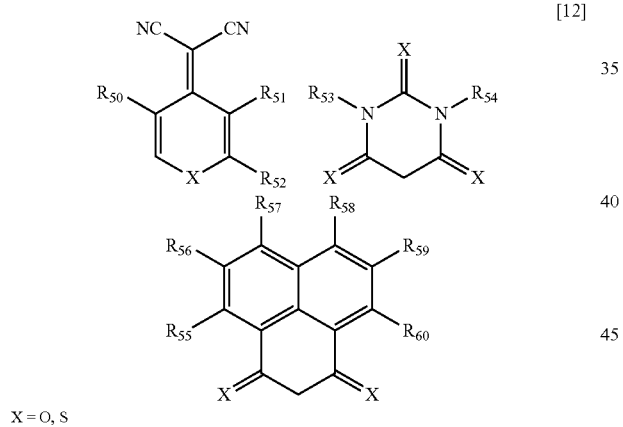

[12]

X = O, S

The spacer backbone of a spare compound according to the present invention can be synthesized according to, for example, a synthetic scheme represented by formula [13].

[Chem. 37]

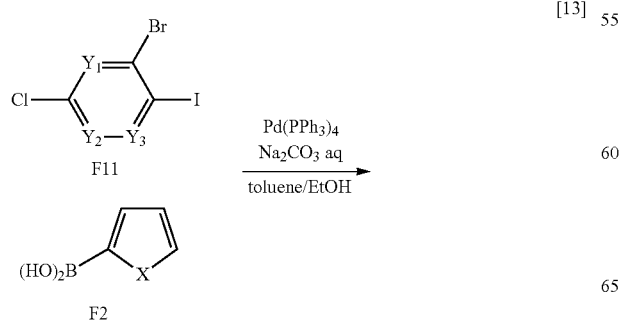

[13]

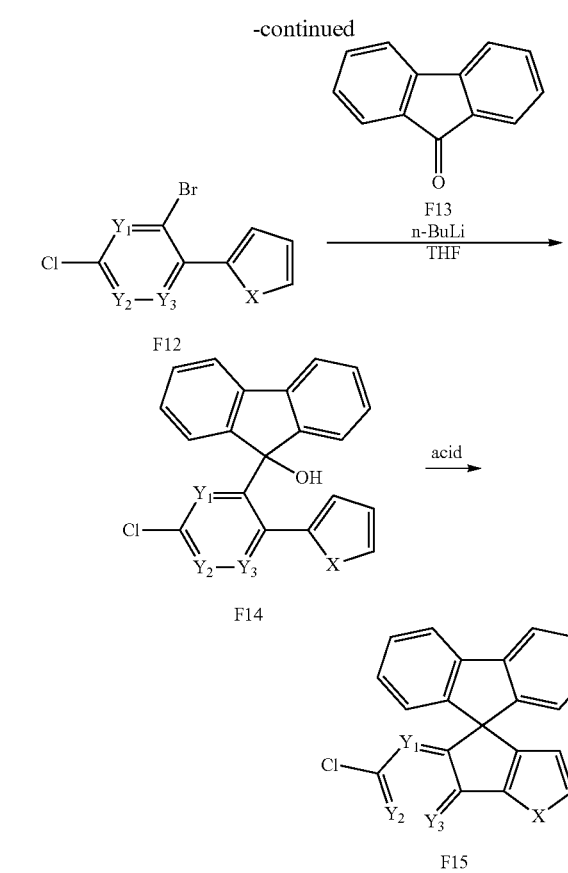

Specifically, the synthesis is performed by sequentially performing reactions (1) to (3) below.

(1) F12 can be synthesized by a cross-coupling reaction of a chalcogenophene-boron compound (F2) with F11 in the presence of a Pd catalyst. When F11 is a pyridine ring, a pyrimidine ring, a pyrazine ring, or a triazine ring, a compound corresponding thereto can be synthesized. When F2 is 2-thiopheneboronic acid, a compound in which X is sulfur can be synthesized. When F2 is 2-furanylboronic acid, a compound in which X is oxygen can be synthesized.

(2) F14 can be synthesized by lithiation of F12 with an alkyllithium reagent and then a nucleophilic addition reaction to a carbonyl compound (F13). F13 is not limited to 9-fluorenone represented by general formula [13], may be a 9-fluorenone derivative containing a substituent or a nitrogen atom.

(3) F15 can be synthesized by subjecting F14 to an intramolecular cyclization reaction with a Lewis acid or an acid.

Exemplified compounds according to the present invention can be synthesized according to the synthetic schemes represented by formulae [9] and [11] by changing D6 and F6 to the basic backbone F15 and similarly performing synthesis. Various exemplified compounds can be synthesized by changing F15, $Ar_1$, and $Ar_2$. Table 5 presents the specific examples.

TABLE 5

| | D6 | D7 | D10 | Exemplified compound No. |
|---|---|---|---|---|
| 1 | | | | A1 |
| 2 | | | | A3 |
| 3 | | | | A7 |
| 4 | | | | A9 |
| 5 | | | | A10 |
| 6 | | | | A16 |
| 7 | | | | B2 |

TABLE 5-continued
| | | | | Exemplified compound No. |
|---|---|---|---|---|
| 8 | 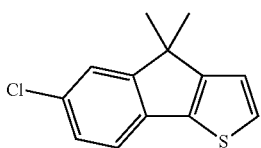 | 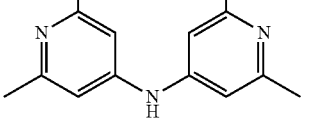 | 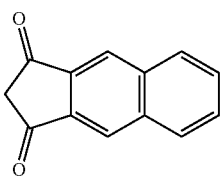 [SMILES: O=C1CC(=O)c2cc3ccccc3cc21] | B5 |
| 9 | 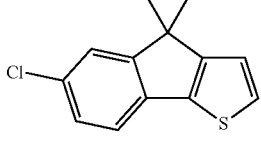 | 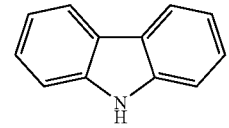 [SMILES: c1ccc2c(c1)[nH]c1ccccc12] | 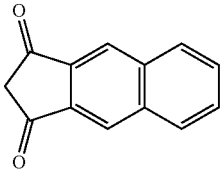 [SMILES: O=C1CC(=O)c2cc3ccccc3cc21] | B9 |
| 10 | 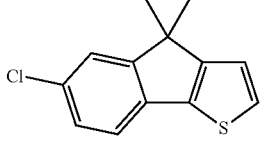 | 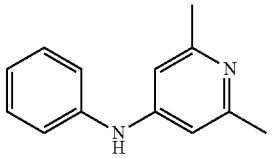 | 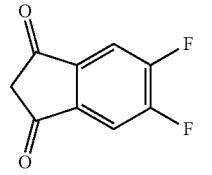 [SMILES: O=C1CC(=O)c2cc(F)c(F)cc21] | B12 |
| 11 | 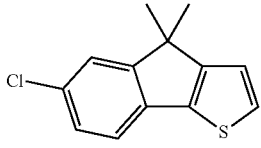 | 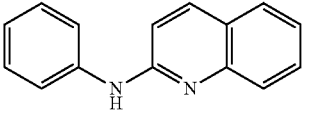 [SMILES: c1ccc(Nc2ccc3ccccc3n2)cc1] | 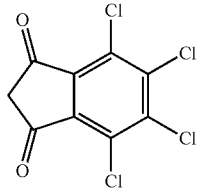 [SMILES: O=C1CC(=O)c2c(Cl)c(Cl)c(Cl)c(Cl)c21] | B15 |
| 12 | 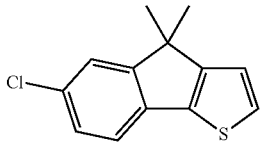 | 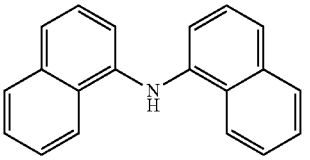 [SMILES: c1ccc2c(Nc3cccc4ccccc34)cccc2c1] | 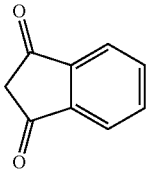 [SMILES: O=C1CC(=O)c2ccccc21] | B19 |
| 13 | 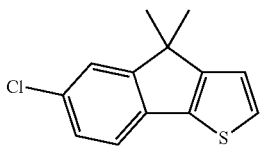 | 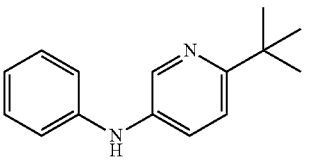 [SMILES: CC(C)(C)c1ccc(Nc2ccccc2)cn1] | 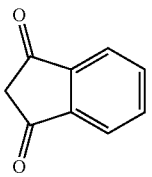 [SMILES: O=C1CC(=O)c2ccccc21] | B21 |
| 14 | 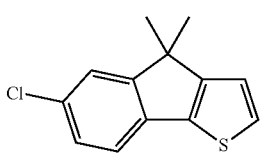 | 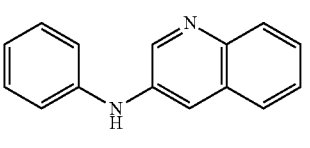 [SMILES: c1ccc(Nc2cnc3ccccc3c2)cc1] | 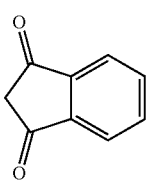 [SMILES: O=C1CC(=O)c2ccccc21] | B22 |
| 15 | 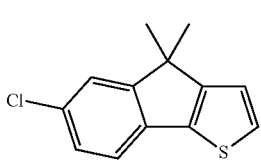 | 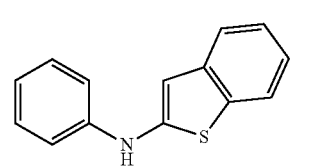 [SMILES: c1ccc(Nc2cc3ccccc3s2)cc1] | 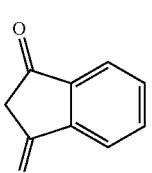 | B23 |

TABLE 5-continued
| | | | | Exemplified compound No. |
|---|---|---|---|---|
| 16 | 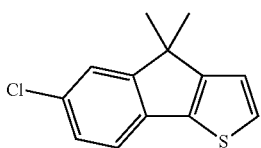 | 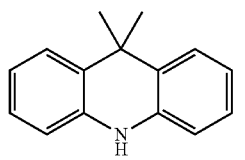 [SMILES: CC1(C)c2ccccc2Nc2ccccc21] | 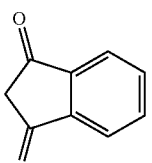 | B30 |
| 17 | 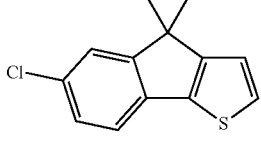 | 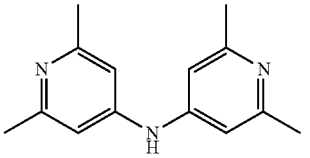 | 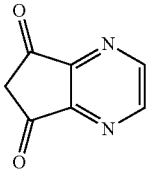 [SMILES: O=C1CC(=O)c2nccnc21] | B31 |
| 18 | 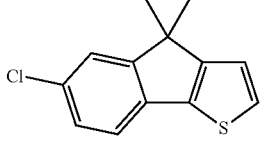 | 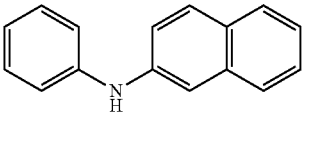 [SMILES: c1ccc(Nc2ccc3ccccc3c2)cc1] | 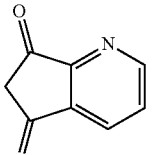 | B33 |
| 19 | 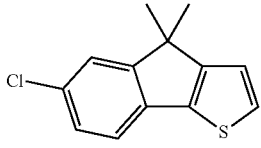 | 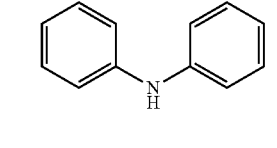 [SMILES: c1ccc(Nc2ccccc2)cc1] | 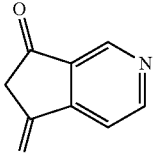 | B38 |
| 20 | 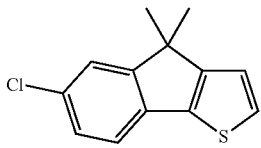 | 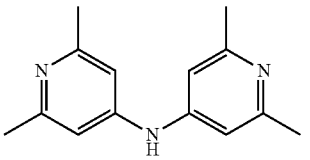 | 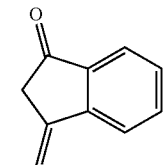 | B40 |
| 21 | 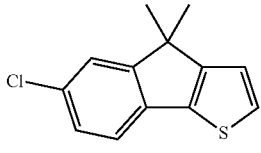 | 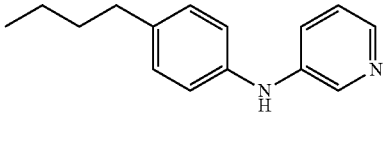 [SMILES: CCCCc1ccc(Nc2cccnc2)cc1] | 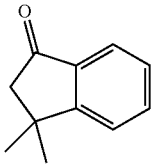 | B45 |
| 22 | 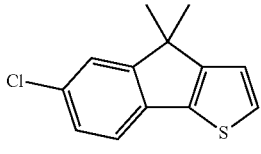 | 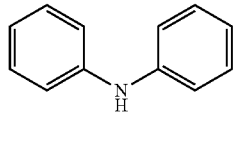 [SMILES: c1ccc(Nc2ccccc2)cc1] | 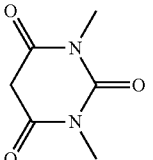 | B46 |
| 23 | 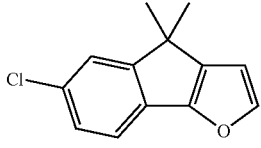 | 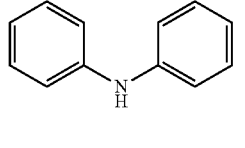 [SMILES: c1ccc(Nc2ccccc2)cc1] | 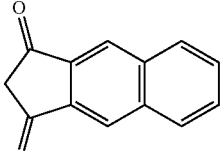 | C3 |

TABLE 5-continued
| | | | | Exemplified compound No. |
|---|---|---|---|---|
| 24 | 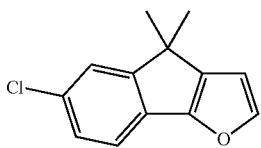 | 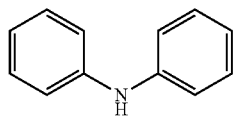 | 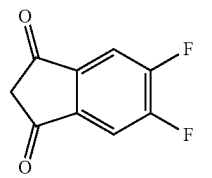 [SMILES: O=C1CC(=O)c2cc(F)c(F)cc21] | C5 |
| 25 | 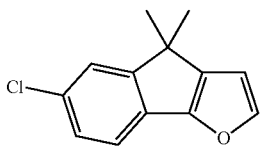 | 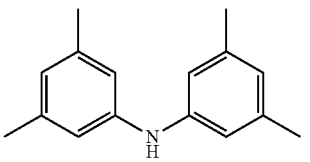 | 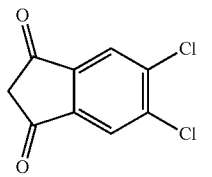 [SMILES: O=C1CC(=O)c2cc(Cl)c(Cl)cc21] | C8 |
| 26 | 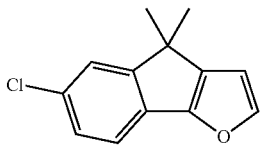 | 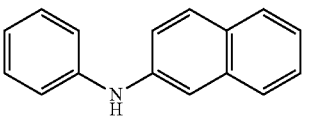 [SMILES: c1ccc(Nc2ccc3ccccc3c2)cc1] | 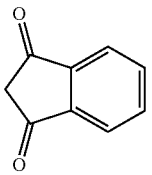 [SMILES: O=C1CC(=O)c2ccccc21] | C11 |
| 27 | 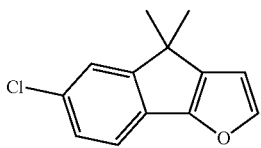 | 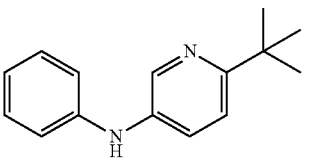 [SMILES: CC(C)(C)c1ccc(Nc2ccccc2)cn1] | 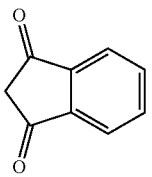 [SMILES: O=C1CC(=O)c2ccccc21] | C14 |
| 28 | 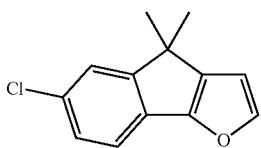 | 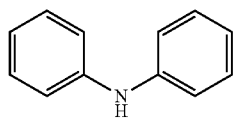 [SMILES: c1ccc(Nc2ccccc2)cc1] | 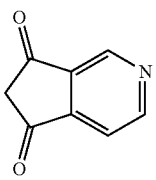 [SMILES: O=C1CC(=O)c2cnccc21] | C16 |
| 29 | 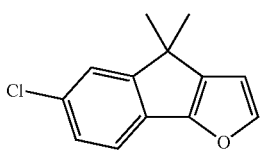 | 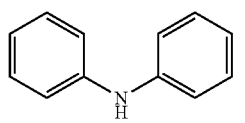 [SMILES: c1ccc(Nc2ccccc2)cc1] | 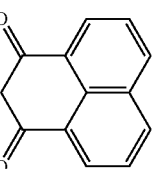 | C24 |
| | F6 | F7 | F10 | |
| 30 | 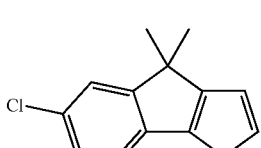 | 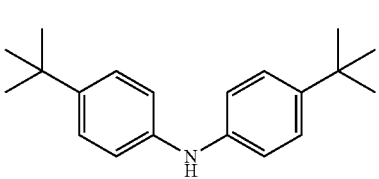 [SMILES: CC(C)(C)c1ccc(Nc2ccc(C(C)(C)C)cc2)cc1] | 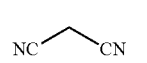 | AA3 |

TABLE 5-continued

| | | | | Exemplified compound No. |
|---|---|---|---|---|
| 32 | (structure) | (structure) | (structure) | AA6 |
| 33 | (structure) | (structure) | (structure) | AA10 |
| 34 | (structure) | (structure) | (structure) | AA13 |
| 35 | (structure) | (structure) | (structure) | BB7 |
| 36 | (structure) | (structure) | (structure) | BB8 |
| 37 | (structure) | (structure) | (structure) | BB9 |
| 38 | (structure) | (structure) | (structure) | BB11 |
| 39 | (structure) | (structure) | (structure) | BB15 |

TABLE 5-continued

| | | | | Exemplified compound No. |
|---|---|---|---|---|
| 40 | | | | BB21 |
| 41 | | | | BB34 |
| 42 | | | | BB37 |
| 43 | | | | BB40 |
| 44 | | | | BB44 |
| 45 | | | | BB47 |
| 46 | | | | BB48 |
| 47 | | | | CC3 |

TABLE 5-continued

| | | | | Exemplified compound No. |
|---|---|---|---|---|
| 48 | (chloro-dimethyl-pyridofurocyclopentene) | diphenylamine | naphtho-indanedione | CC4 |
| 49 | (chloro-dimethyl-pyridofurocyclopentene) | diphenylamine | naphtho-indanedione | CC5 |
| 50 | (chloro-dimethyl-pyridofurocyclopentene) | diphenylamine | difluoro-indanedione | CC6 |
| 51 | (chloro-dimethyl-pyridofurocyclopentene) | bis(4-methylphenyl)amine | difluoro-indanedione | CC8 |
| 52 | (chloro-dimethyl-pyridofurocyclopentene) | N-phenyl-2-naphthylamine | indanedione | CC12 |
| 53 | (chloro-dimethyl-pyridofurocyclopentene) | bis(4-tert-butylphenyl)amine | indanedione | CC15 |
| 54 | (chloro-dimethyl-pyrimidofurocyclopentene) | bis(4-methylphenyl)amine | cyclopenta-pyrazine-dione | CC16 |
| 55 | (chloro-dimethyl-pyridofurocyclopentene) | diphenylamine | cyclopenta-pyridine-dione | CC17 |

TABLE 5-continued

| | F15 | F7 | F10 | Exemplified compound No. |
|---|---|---|---|---|
| 56 | 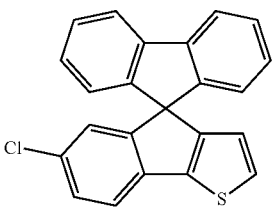 | 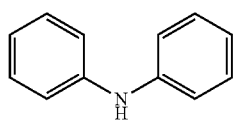 | 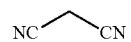 | A33 |
| 57 | 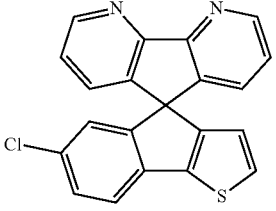 | 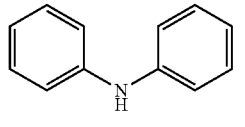 | 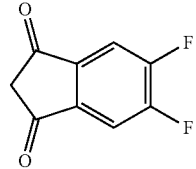 | B54 |
| 57 | 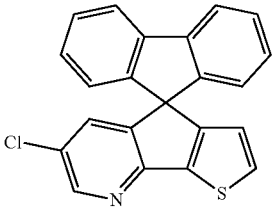 | 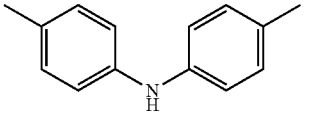 | 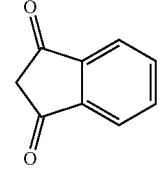 | BB64 |

Embodiment of Photoelectric Conversion Element

A photoelectric conversion element according to the present invention includes a pair of electrodes and a photoelectric conversion layer disposed between the pair of electrodes, the photoelectric conversion layer containing an organic compound represented by general formula [1]. The pair of electrodes includes a hole-collecting electrode and an electron-collecting electrode. They also may be referred to as a cathode and anode. The use of the organic compound according to the present invention is not limited to the photoelectric conversion element. The organic compound according to the present invention may be used for an organic electronic element including a pair of electrodes and an organic compound layer disposed between the pair of electrodes, the organic compound layer containing the organic compound represented by general formula [1].

FIG. 2 is a schematic cross-sectional view illustrating an example of a photoelectric conversion element according to this embodiment. The photoelectric conversion element includes a first organic compound layer 1 serving as a photoelectric conversion portion that converts light into an electrical charge, the first organic compound layer 1 being disposed between a hole-collecting electrode 4 and an electron-collecting electrode 5. The first organic compound layer 1 is a layer that converts light into an electrical charge and thus may also be referred to as a "photoelectric conversion layer". On the hole-collecting electrode, a protective layer 7, a wavelength selection portion 8, and a microlens 9 are disposed. The electron-collecting electrode is connected to a readout circuit 6.

The photoelectric conversion element includes a second organic compound layer 2 disposed between the first organic compound layer and the hole-collecting electrode and a third organic compound layer 3 disposed between the first organic compound layer and the electron-collecting electrode.

The second organic compound layer may be formed of multiple layers or a bulk heterojunction layer (mixed layer). The second organic compound layer is a layer to inhibit electrons from entering the first organic compound layer from the hole-collecting electrode and thus preferably has a low electron affinity (close to the vacuum level).

The third organic compound layer may be formed of multiple layers or a bulk heterojunction layer (mixed layer). The third organic compound layer is a layer to inhibit the holes from entering the first organic compound layer from the electron-collecting electrode and thus preferably has a high ionization potential (distant from the vacuum level).

To improve the injection properties of generated charges into the electrode or to inhibit the injection of charges from the electrode into the organic compound layer at the application of a voltage, an organic compound layer or an inorganic compound layer may be disposed between the organic compound layer and the hole-collecting electrode 4 and between the organic compound layer and the electron-collecting electrode 5.

The first organic compound layer may contain different types of organic compounds. In the case where the first organic compound layer contains the different types of organic compounds, a mixture of the different types of organic compounds may be present in one layer. Alternatively, the different types of organic compounds may be contained in different layers.

In the case where the photoelectric conversion element includes multiple layers, the multiple layers are stacked in the direction from the electron-collecting electrode to the hole-collecting electrode.

The first organic compound layer preferably contains a p-type organic semiconductor or an n-type organic semiconductor. More preferably, the first organic compound layer at least partially includes a bulk heterojunction layer (mixed layer) in which an organic p-type compound and an organic n-type compound are mixed together.

Because the first organic compound layer includes the bulk heterojunction layer, the photoelectric conversion efficiency (sensitivity) can be improved. The arrangement of the bulk heterojunction layer having an optimal mixing ratio can enhance the electron mobility and the hole mobility of the first organic compound layer 1 to increase the optical response speed of the photoelectric conversion element.

The first organic compound layer preferably contains fullerene or a fullerene analogue as an n-type organic semiconductor. Electron paths are formed by fullerene molecules or molecules of the fullerene analogue, thus improving the electron transport properties to improve the fast responsiveness of the photoelectric conversion element.

The fullerene content or the fullerene analogue content is preferably 20% or more by volume and 80% or less by volume with respect to 100% of the total amount of the photoelectric conversion layer.

The term "fullerene analogue" is the generic name of a closed-shell hollow cluster consisting only of many carbon atoms. Examples thereof include C60 and higher-order fullerenes such as C70, C74, C76, and C78. These materials may be used alone or in combination. Regarding a material used for charge separation and electron transport, other different materials may be used together with the fullerene analogues. Examples of materials other than fullerene include naphthalene compounds such as NTCDI, perylene compounds such as PTCDI, phthalocyanine compounds such as SubPc, and thiophene compounds such as DCV3T, which are known as n-type organic semiconductors.

Examples of the fullerene analogue are, but not limited to, described below.

Fullerenes

Examples thereof include fullerene C60, fullerene C70, fullerene C76, fullerene C78, fullerene C80, fullerene C82, fullerene C84, fullerene C90, fullerene C96, fullerene C240, fullerene 540, mixed fullerene, and fullerene nanotubes.

[Chem. 38]

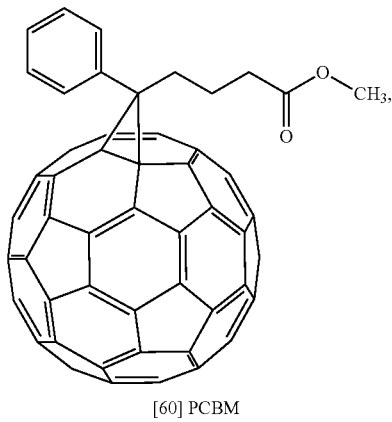

[60] PCBM

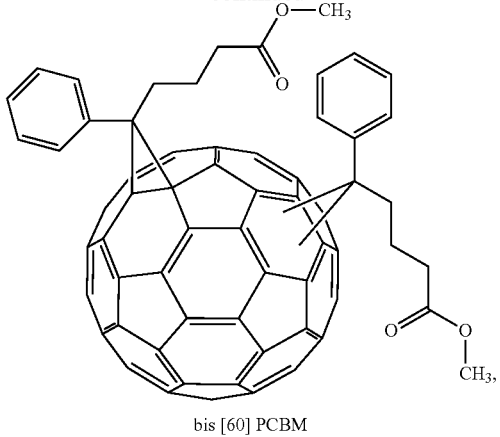

bis [60] PCBM

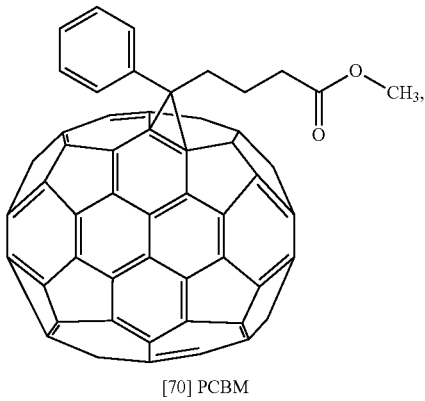

[70] PCBM

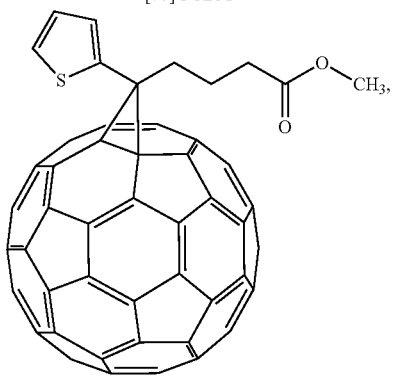

[60] ThCBM

The photoelectric conversion element according to the present invention may include a semiconductor substrate. The constituent element of the semiconductor substrate is not limited as long as a charge accumulation portion and FD can be formed by injection of an impurity. Examples thereof include Si, GaAs, and GaP. In particular, Si is preferred.

The semiconductor substrate may be an N-type epitaxial layer. In this case, the semiconductor substrate includes a P-type well, an N-type well, a P-type semiconductor region, and an N-type semiconductor region.

The charge accumulation portion is an N-type semiconductor region or a P-type semiconductor region formed by ion implantation in the semiconductor substrate and is a region where charges generated in the photoelectric conversion portion are accumulated.

In the case of accumulating electrons, the N-type semiconductor region may be formed on a surface of the semiconductor substrate. Alternatively, an accumulation diode having a PN structure may be formed on a surface of the substrate. In any case, electrons can be accumulated in the N-type semiconductor region.

In the case of accumulating holes, a P-type semiconductor region is formed on/in the semiconductor substrate. Alternatively, an accumulation diode having an NP structure may be formed on a surface of the substrate. In any case, electrons can be accumulated in the P-type semiconductor region.

The accumulated charges are transferred from the charge accumulation portion to FD. The charge transfer may be controlled using a gate electrode. The charges formed in the organic compound layer are accumulated in the charge accumulation portion. The charges accumulated in the charge accumulation portion are transferred to FD. Then the charges are converted by an amplifying transistor into a current.

In the case where the charge accumulation portion forms a PN junction, photoelectric conversion may be performed with light leaked from the photoelectric conversion portion.

The electrode 4 is also referred to as an "upper electrode" and is preferably composed of a transparent conductive material. The electrode is composed of, for example, indium-tin oxide (ITO), indium-zinc oxide (IZO), or a conducting organic material. Any optically transparent material other than those above may be used. For example, a thin film composed of silver, magnesium, or an alloy thereof may be formed. The electrode can be formed by a known method such as a sputtering method or a vapor deposition method.

The photoelectric conversion layers, the functional layers, and the electrodes of the photoelectric conversion elements may be formed separately or collectively by, for example, a vacuum deposition method or an application method.

The protective layer 7 is disposed on the upper portion of the electrode and is preferably an insulating layer. The protective layer may be composed of a single material or different materials. In the case where the protective layer is composed of the different materials, the protective layer may be formed of stacked layers or a layer containing a mixture of the different materials. Examples of a constituent material of the protective layer include organic materials such as resins; and inorganic materials such as SiNx, SiOx, and $Al_2O_3$. Each X is the value of an elemental ratio.

A planarizing layer may be disposed on the protective layer 7. The planarizing layer is disposed in order to eliminate the effect of the surface state of the protective layer on the wavelength selection portion. The planarizing layer can be formed by a known production method such as an application method or a vacuum deposition method. The planarizing layer may be formed by, for example, CMP, as needed.

Examples of a material of the planarizing layer include organic materials such as resins; and inorganic materials such as SiNx, SiOx, and $Al_2O_3$. The planarizing layer may be composed of an organic compound or a mixture thereof.

The wavelength selection portion 8 is disposed on the planarizing layer. In the case where the planarizing layer is not provided, the wavelength selection portion is disposed on the protective layer. The wavelength selection portion may be disposed on the light incident side of the photoelectric conversion element. Examples of the wavelength selection portion include color filters, scintillators, and prisms.

Color filters are each a filter that transmits a large quantity of light having a predetermined wavelength, compared with light having other wavelengths. For example, the use of three types of filters, i.e., RGB, can deal with the entire visible light region. In the case of using the three RGB filters, the color filters may be arranged in the Bayer pattern or the like. The wavelength selection portion may be formed of a prism that separates only light having a predetermined wavelength.

The position of the wavelength selection portion 8 is not limited to the position illustrated in FIG. 1. The wavelength selection portion may be disposed at any position in a light path extending from a subject or a light source to the photoelectric conversion layer 4.

The microlens 9 is an optical member to collect light from the outside into the photoelectric conversion layer. FIG. 1 illustrates the lens having a hemispherical shape. However, the shape of the lens is not limited thereto.

The microlens is composed of, for example, quartz, silicon, or an organic resin. The shape and the material are not limited as long as the collection of light is not impaired.

The photoelectric conversion element may include another photoelectric conversion element on the electrode. In the case of using the another photoelectric conversion element that photoelectrically converts light having a different wavelength, light beams having different wavelengths can be detected at the same in-plane position or substantially the same in-plane position on the substrate.

The photoelectric conversion element may further include another organic compound layer that photoelectrically converts light having a wavelength different from light photoelectrically converted by the organic compound layer, the another organic compound layer and the organic compound layer being stacked. In this structure, similarly to the structure in which the photoelectric conversion elements are stacked, light beams having different wavelengths can be detected at the same position or substantially the same position on the substrate.

The hole-collecting electrode 4 is an electrode that collects holes of charges generated in the photoelectric conversion layer. In the case of the structure of an image-pickup element, the hole-collecting electrode may be a pixel electrode. Any material that is highly conductive and transparent may be used for the hole-collecting electrode 4.

Specific examples thereof include metals, metal oxides, metal nitrides, metal borides, organic conductive compounds, and mixtures thereof. More specific examples thereof include conductive metal oxides such as tin oxide doped with antimony or fluorine (ATO or FTO), tin oxide, zinc oxide, indium oxide, indium-tin oxide (ITO), and indium-zinc oxide (IZO); metals such as gold, silver, chromium, nickel, titanium, tungsten, and aluminum; conductive compounds such as oxides and nitrides of these metals (for example, titanium nitride (TiN)); mixtures and laminates of the metals and the conductive metal oxides; inorganic conductive substances such as copper iodide and copper sulfide; organic conductive materials such as polyaniline, polythiophene, and polypyrrole; and laminates of these materials and ITO or titanium nitride. The hole-collecting electrode 4 is particularly preferably composed of titanium nitride, molybdenum nitride, tantalum nitride, or tungsten nitride.

The electron-collecting electrode 5 is an electrode that collects electrons of charges generated in the photoelectric conversion layer. In the case of the structure of an image pickup element, the electron-collecting electrode may be a pixel electrode. The electron-collecting electrode 5 may be disposed closer to a pixel circuit than the hole-collecting electrode 4.

Specifically, ITO, IZO, SnO2, antimony-doped tin oxide (ATO), ZnO, Al-doped zinc oxide (AZO), gallium-doped zinc oxide (GZO), $TiO_2$, or fluorine-doped tin oxide (FTO) is used.

A method for forming the electrode can be appropriately selected in consideration of suitability for the material of the electrode. Specifically, the electrode can be formed by a wet process such as a printing method or a coating method, a physical process such as a vacuum deposition method, a sputtering method, and an ion plating method, or a chemical process such as CVD or a plasma-enhanced CVD method. In the case where the electrode is composed of ITO, the electrode can be formed by an electron beam method, a sputtering method, a resistance heating evaporation method, a chemical reaction method (e.g., a sol-gel method), or application of an indium-tin oxide dispersion.

The resulting ITO can be subjected to, for example, UV-ozone treatment or plasma treatment. In the case where the electrode is composed of TiN, various methods such as a reactive sputtering method can be used. Furthermore, annealing treatment, UV-ozone treatment, plasma treatment, or the like can be performed.

When photoelectric conversion is performed in the photoelectric conversion element, a voltage is preferably applied between the hole-collecting electrode and the electron-collecting electrode. The voltage is preferably about 1 V or more and about 15 V or less, more preferably about 2 V or more and about 10 V or less, depending on the total thickness of the organic compound layers.

Image Pickup Element Including Photoelectric Conversion Element According to Present Invention The photoelectric conversion element according to the present invention can be used for an area photosensor including two-dimensionally arranged elements in the in-plane directions. The area photosensor includes photoelectric conversion elements arranged in the longitudinal and transverse directions.

The photoelectric conversion element according to the present invention can be used for an image pickup element. The image pickup element includes photoelectric conversion elements serving as light-receiving pixels and transistors connected to the respective photoelectric conversion elements. The transistors read charges generated in the photoelectric conversion elements. Information sets based on the read charges are transmitted to a sensor unit connected to the image pickup element. Examples of the sensor unit include CMOS sensors and CCD sensors. Information sets acquired from the light-receiving pixels are collected to the sensor unit, thereby forming an image.

The image pickup element includes the photoelectric conversion elements and different types of color filters. The different types of color filters transmit light beams having different wavelengths. The photoelectric conversion elements include a photoelectric conversion layer as a common layer. The common photoelectric conversion layer contains the organic compound according to the present invention and an n-type organic semiconductor.

In the case where the organic compound according to the present invention and the n-type organic semiconductor are used, a broad light absorption is provided; thus, photoelectric conversion can be performed in the wavelength range of all types of color filters without using another organic compound.

The photoelectric conversion element according to the present invention can be used for an image pickup element. The image pickup element includes a photoelectric conversion element and a signal processing circuit.

The image pickup element according to the present invention can be used for an image pickup device. The image pickup device includes an image pickup optical system including lenses and an image pickup element that receives light passing through the image pickup optical system. Furthermore, the image pickup device includes the image pickup element and a housing that accommodates the image pickup element. The housing may have a connection portion that is connectable to the image pickup optical system. Specifically, the image pickup device is a digital camera or a digital still camera.

The image pickup device may further include a receiving unit that receives a signal from the outside. The signal received by the receiving unit is a signal to control at least one of the image pickup range, the start of an image pickup operation, and the end of the image pickup operation of the image pickup device. The image pickup device may further include a transmitting unit that transmits an acquired image to the outside.

The image pickup device including the receiving unit and the transmitting unit can be used as a network camera.

Figure 3:
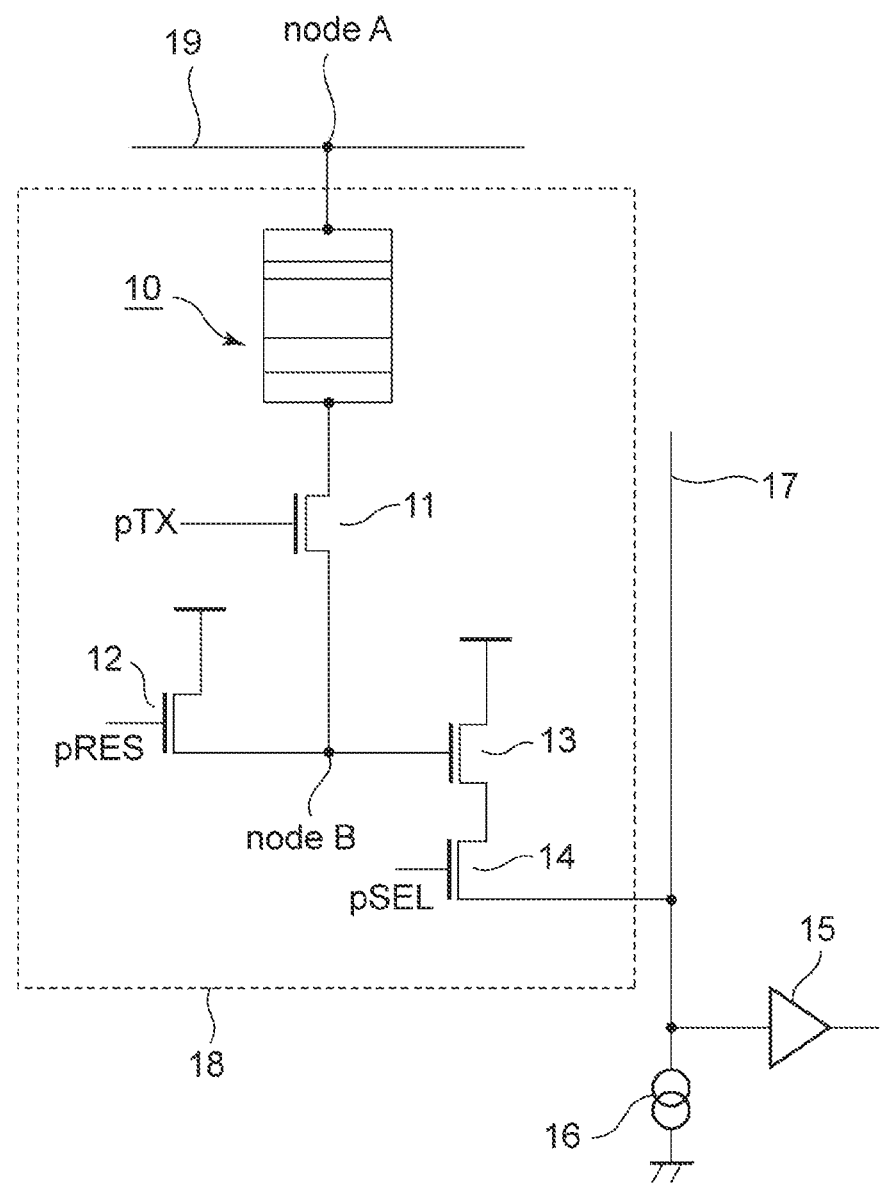
FIG. 3 is a schematic diagram illustrating an example of a drive circuit diagram of a pixel including a photoelectric conversion element containing an organic compound according to the present invention.

FIG. 3 is a circuit diagram of a pixel including the photoelectric conversion device according to the present invention. A photoelectric conversion device 10 is connected to a common line 19 at node A. The common line may be connected to the ground.

A pixel 18 may include the photoelectric conversion element 10 and a readout circuit to read a signal generated in the photoelectric conversion portion. The readout circuit may include, for example, a transfer transistor 11 electrically connected to the photoelectric conversion element, an amplification transistor 13 including a gate electrode electrically connected to the photoelectric conversion element 10, a selection transistor 14 to select a pixel to read information, and a reset transistor 12 to supply a reset voltage to the photoelectric conversion element.

The transfer by the transfer transistor 11 may be controlled by pTX. The supply of voltage to the reset transistor may be controlled by pRES. The selection transistor is in a selected or unselected state in response to pSEL.

The transfer transistor 11, the reset transistor 12, and the amplification transistor 13 are connected together at node B. The transfer transistor need not be included, depending on the configuration.

The reset transistor is a transistor that supplies a voltage to reset the potential of node B. The application of pRES to the gate of the reset transistor controls the supply of the voltage. The reset transistor need not be included, depending on the configuration.

The amplification transistor is a transistor to apply a current corresponding to a potential at node B. The amplification transistor is connected to the selection transistor 14 to select a pixel that outputs a signal. The selection transistor is connected to a current source 16 and a column output unit 15. The column output unit 15 may be connected to a signal processing unit.

The selection transistor 14 is connected to a vertical output signal line 17. The vertical output signal line 17 is connected to the current source 16 and the column output unit 15.

Figure 4:
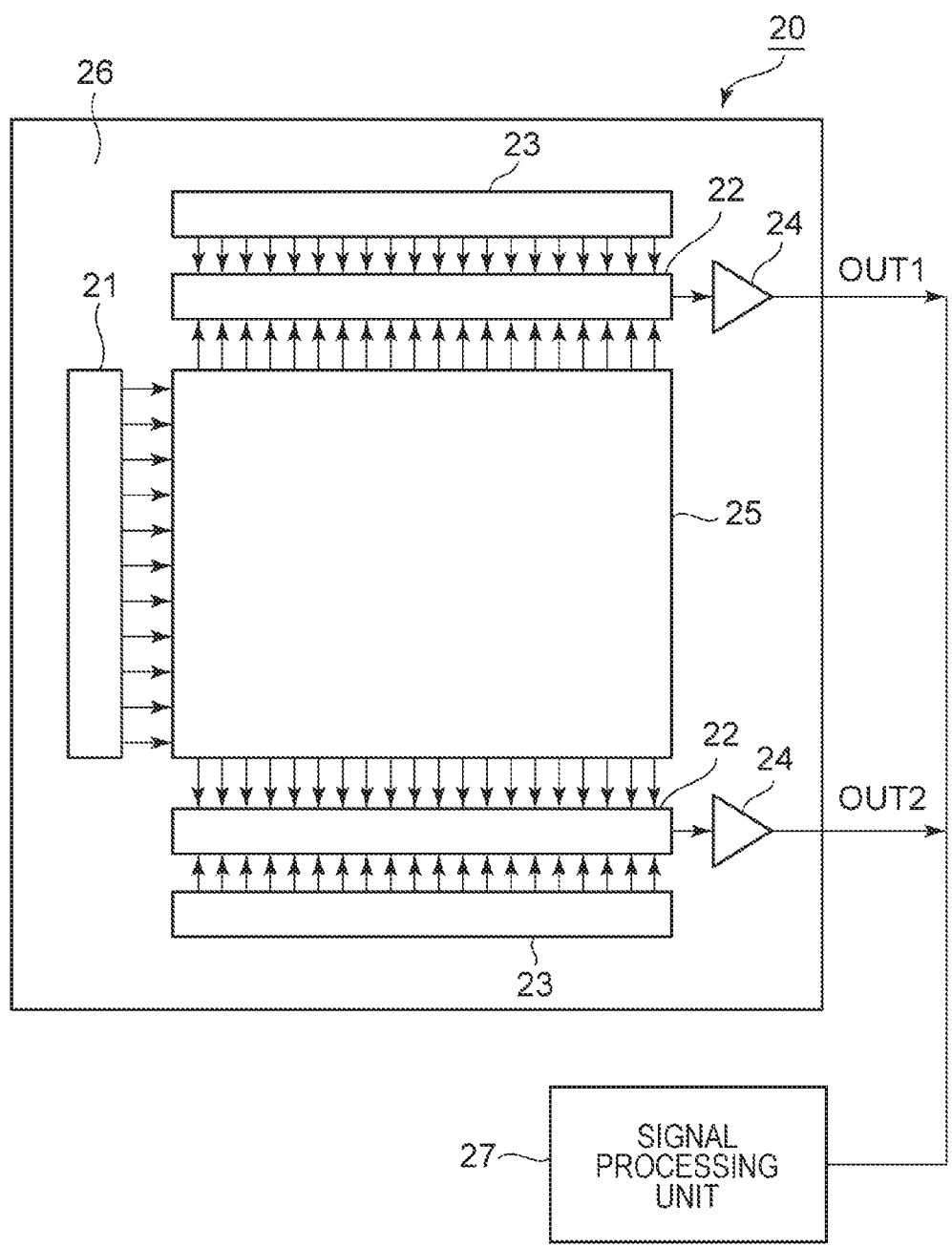
FIG. 4 is a schematic diagram illustrating an example of a peripheral circuit diagram including a photoelectric conversion element containing an organic compound according to the present invention.

FIG. 4 illustrates an image pickup element according to the present invention. An image pickup element 20 includes an image pickup region 25 including two-dimensionally arranged pixels and a peripheral region 26. A region except the image pickup region is the peripheral region. The peripheral region includes a vertical scanning circuit 21, readout circuits 22, horizontal scanning circuits 23, and output amplifiers 24. The output amplifiers are connected to a signal processing unit 27. The signal processing unit is a signal processing unit to perform signal processing on the basis of information read into the readout circuit. Examples thereof include CCD circuits and CMOS circuits.

Each of the readout circuits 22 includes, for example, a column amplifier, a CDS circuit, and an adding circuit and subjects a signal read from a pixel of a row selected by the vertical scanning circuit 21 via the vertical signal line to amplification, addition, and the like. The row amplifier, the CDS circuit, the adding circuit, and so forth are arranged for each row of pixels or every two or more rows of pixels. Each of the horizontal scanning circuits 23 generates a signal to sequentially read a signal from a corresponding one of the readout circuits 22. Each of the output amplifiers 24 amplifies a signal from a row selected by a corresponding one of the horizontal scanning circuits 23 and outputs the resulting signal.

The foregoing configuration is merely a configurational example of the photoelectric conversion device. This embodiment is not limited thereto. The readout circuits 22, the horizontal scanning circuits 23, and the output amplifiers 24 are arranged in respective regions on upper and lower sides of the image pickup region 25 in order to constitute two output paths. However, three or more output paths may be provided. Signals supplied from the output amplifiers are combined by the signal processing unit to generate image signals.

EXAMPLES

While the present invention will be described in detail by examples, the present invention is not limited thereto.

Example 1

Exemplified Compound A1

Exemplified compound A1 was synthesized according to a scheme illustrated below.

[Chem. 39]

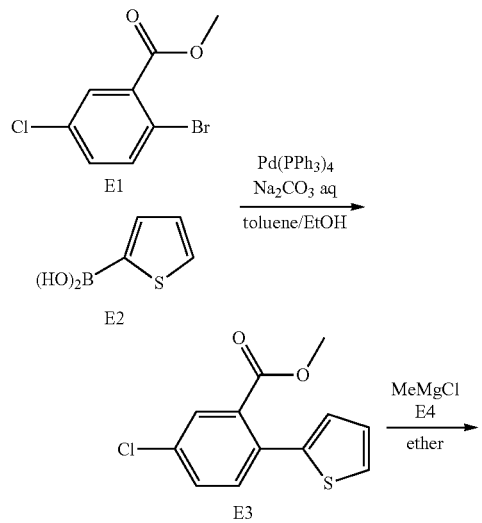

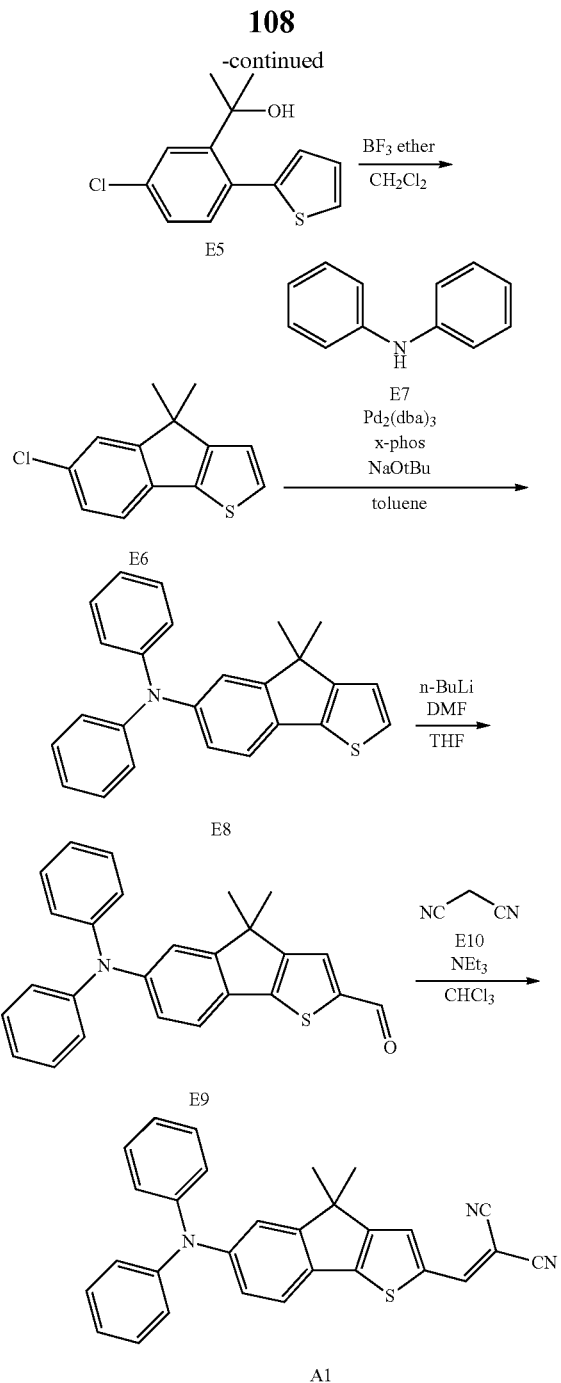

First, 20.0 g (80.2 mmol) of E1, 15.4 g (120.2 mmol) of E2 were added to 100 ml of toluene, 50 ml of ethanol, and 150 ml of a 20% by mass aqueous solution of sodium carbonate. Then 2.8 g (2.4 mmol) of tetrakis(triphenylphosphine)palladium(0) was added thereto. The mixture was heated to 90° C. with stirring for 8.5 hours. After cooling, the mixture was subjected to extraction with toluene. The extract was concentrated and purified by silica-gel column chromatography (mobile phase: heptane:toluene=3:1) to give 16.5 g of clear, colorless liquid E3 (yield: 81%).

To 400 ml of tetrahydrofuran, 16.5 g (65.3 mmol) of E3 was added. Then 42 ml (195.9 mmol) of E4 (3.0 M tetrahydrofuran solution) was added dropwise thereto at 30° C. The mixture was heated to reflux with stirring for 3 hours. After the reaction, the mixture was cooled to 0° C. Ethanol, water, and dilute hydrochloric acid were added thereto in this order. The mixture was subjected to extraction with ethyl acetate. After concentration, the residue was purified by silica-gel column chromatography (mobile phase: heptane:chloroform=2:1) to give 7.6 g of pale yellow liquid E5 (yield: 72%).

To 570 ml of dichloromethane, 7.6 g (30.0 mmol) of E5 was added. Then 3.8 ml (30.0 mmol) of boron trifluoride diethyl etherate was added dropwise thereto at 0° C. The mixture was stirred for 15 minutes. After the reaction, an aqueous solution of sodium hydrogen carbonate was added thereto. The mixture was subjected to extraction with dichloromethane. After concentration, the residue was purified by silica-gel column chromatography (mobile phase: heptane) to give 6.3 g of white solid E6 (yield: 89%).

To 5 ml of toluene, 183 mg (0.2 mmol) of tris(dibenzylideneacetone)dipalladium(0) and 286 mg (0.6 mmol) of x-phos were added. The mixture was stirred for 15 minutes at room temperature. The resulting solution was added to 15 ml of a separately prepared toluene solution containing 940 mg (4.0 mmol) of E6 and 745 mg (4.4 mmol) of E7 dissolved therein. Then 770 mg (8.0 mmol) of sodium tert-butoxide was added thereto. The mixture was stirred at 120° C. for 4 hours. After cooling, the mixture was filtered with Celite. The extract was concentrated. The residue was purified by silica-gel column chromatography (mobile phase: heptane:toluene=10:1) to give 1.4 g of white solid E8 (yield: 96%).

To 40 ml of tetrahydrofuran, 1.4 g (3.9 mmol) of E8 was added. The mixture was cooled to −40° C. Then 2.9 ml (4.6 mmol) of n-butyllithium (1.6 M n-hexane solution) was added dropwise thereto at −40° C. The mixture was stirred for 2 hours at the temperature. Then 1.2 ml (15.4 mmol) of DMF was added dropwise thereto at −40° C. The mixture was stirred for 3 hours while being slowly brought to room temperature. After the reaction, an aqueous solution of ammonium chloride was added thereto. The mixture was subjected to extraction with ethyl acetate. After concentration, the residue was purified by silica-gel column chromatography (mobile phase: heptane:dichloromethane=1:1) to give 1.0 g of yellow solid E9 (yield: 66%).

To 20 ml chloroform, 500 mg (1.3 mmol) of E9 was added. Then 250 mg (3.8 mmol) of E10 and six drops of triethylamine were added thereto. The mixture was stirred for 2 hours. After the reaction, the mixture was subjected to extraction with chloroform. After concentration, the residue was purified by silica-gel column chromatography (mobile phase: chloroform) to give 496 mg of dark red solid A1 (yield: 88%). Mass spectrometry of the product revealed a molecular ion peak at m/z 444, corresponding to M+ of exemplified compound A1.

The measurement of the absorption spectrum of exemplified compound A1 in a dilute chloroform solution revealed that the maximum absorption wavelength in the visible light region was 535 nm. The molar extinction coefficient in the dilute chloroform solution was measured and found to be 57,600 $M^{-1}cm^{-1}$ at a wavelength of 535 nm. As an instrument, a V-560 UV-visible spectrophotometer available from JASCO Corporation was used.

TG-DTA measurement of exemplified compound A1 was performed in a nitrogen atmosphere at a rate of temperature increase of 10° C./min and revealed a decomposition temperature (temperature at which the mass is decreased by 1%) of 307° C. As an instrument, TG-DTA 2000SA available from BRUKER was used.

DSC measurement of exemplified compound A1 was performed in a nitrogen atmosphere at a rate of temperature increase of 10° C./min and revealed a melting point of 215° C. As an instrument, DSC 204 F1 available from NETZSCH was used.

The sublimation purification of exemplified compound A1 revealed a sublimation temperature of 196° C. at a rate of 10 mg/h (i.e., 10 mg of the compound sublimed in 1 hour).

The difference between the melting point and the sublimation temperature measured as described above was calculated and defined as Δtemperature represented by expression [10] described below. Table 7 presents Δtemperature. The case where the value of Δtemperature is 25° C. or higher is rated as ⊙. The case where the value of Δtemperature is 10° C. or higher and lower than 25° C. is rated as ○. The case where the value of Δtemperature is 0° C. or higher and lower than 10° C. is rated as Δ. The case where the value of Δtemperature is lower than 0° C. is rated as ×. Exemplified compound A1 is rated as B because Δtemperature is 19° C.

ΔTemperature=melting point−sublimation temperature (10 mg/h)=215−196=19(° C.) [10]

Example 2

Exemplified Compound A2

Exemplified compound A2 was synthesized as in Example 1, except that compound E11 illustrated below was used in place of E7.

[Chem. 40]

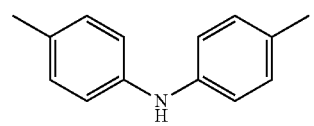

E11

Mass spectrometry of the product revealed a molecular ion peak at m/z 472, corresponding to M+ of exemplified compound A2.

As with Example 1, Δtemperature was calculated from the melting point and the sublimation temperature and is presented in Table 7.

Example 3

Exemplified Compound A4

Exemplified compound A4 was synthesized in the same way as in Example 1, except that compound E12 illustrated below was used in place of E7.

[Chem. 41]

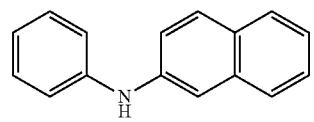

E12

Mass spectrometry of the product revealed a molecular ion peak at m/z 494, corresponding to M+ of exemplified compound A4.

As with Example 1, Δtemperature was calculated from the melting point and the sublimation temperature and is presented in Table 7.

Example 4

Exemplified Compound A10

Exemplified compound A10 was synthesized in the same way as in Example 1, except that compound E13 illustrated below was used in place of E7.

[Chem. 42]

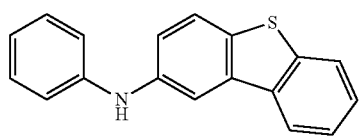

E13

Mass spectrometry of the product revealed a molecular ion peak at m/z 550, corresponding to M+ of exemplified compound A10.

As with Example 1, Δtemperature was calculated from the melting point and the sublimation temperature and is presented in Table 7.

Example 5

Exemplified Compound B1

The same synthesis procedure as in Example 1 was performed up to the production of compound E9.

[Chem. 43]

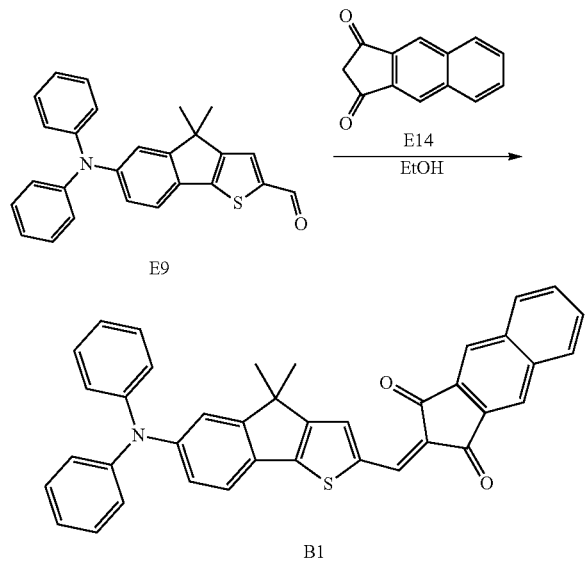

To 100 ml of ethanol, 500 mg (1.3 mmol) of E9 was added. Then 265 mg (1.3 mmol) of E14 was added thereto. The mixture was heated to 90° C. with stirring for 3 hours. After the reaction, the mixture was filtered. The residue was purified by silica-gel column chromatography (mobile phase: chloroform) to give 485 mg of dark golden-green solid B1 (yield: 65%).

Mass spectrometry of the product revealed a molecular ion peak at m/z 574, corresponding to M+ of exemplified compound A1.

As with Example 1, Δtemperature was calculated from the melting point and the sublimation temperature and is presented in Table 7.

Example 6

Exemplified Compound B2

Exemplified compound B2 was synthesized as in Examples 1 and 5, except that compound E15 illustrated below was used in place of E7.

[Chem. 44]

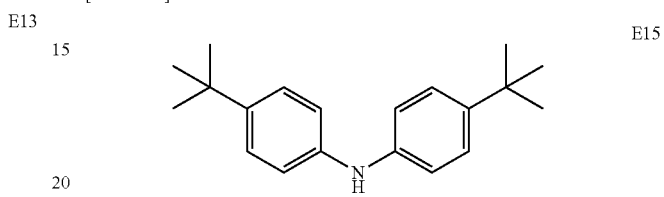

E15

Mass spectrometry of the product revealed a molecular ion peak at m/z 686, corresponding to M+ of exemplified compound B2.

As with Example 1, Δtemperature was calculated from the melting point and the sublimation temperature and is presented in Table 7.

Example 7

Exemplified Compound B10

The same synthesis procedure as in Example 1 was performed up to the production of compound E9.

[Chem. 45]

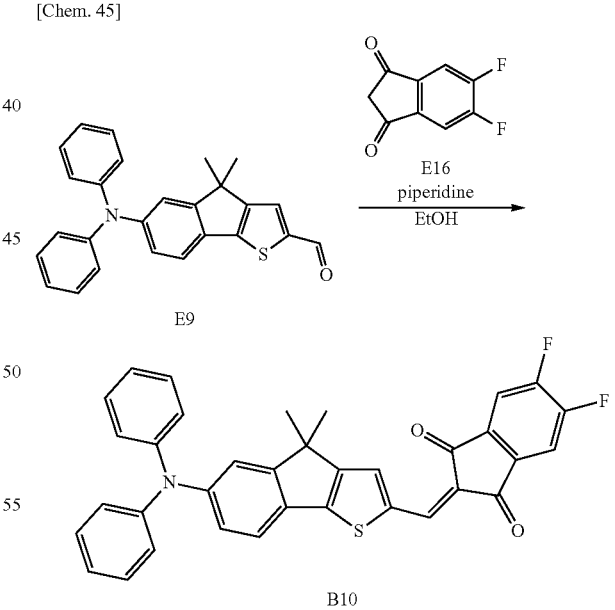

To 140 ml of ethanol, 500 mg (1.3 mmol) of E9 was added. Then 237 mg (1.3 mmol) of E16 and 0.1 ml of piperidine were added thereto. The mixture was heated to 90° C. with stirring for 5 hours. After the reaction, the mixture was filtered. The residue was purified by silica-gel column chromatography (mobile phase: chloroform) to give 515 mg of dark purple solid B10 (yield: 71%).

Mass spectrometry of the product revealed a molecular ion peak at m/z 560, corresponding to M+ of exemplified compound B10.

As with Example 1, Δtemperature was calculated from the melting point and the sublimation temperature and is presented in Table 7.

Example 8

Exemplified Compound B11

Exemplified compound B11 was synthesized as in Examples 1 and 7, except that compound E17 illustrated below was used in place of E7.

[Chem. 46]

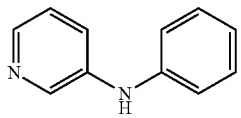

E17

Mass spectrometry of the product revealed a molecular ion peak at m/z 561, corresponding to M+ of exemplified compound B11.

As with Example 1, Δtemperature was calculated from the melting point and the sublimation temperature and is presented in Table 7.

Example 9

Exemplified Compound B16

Exemplified compound B16 was synthesized as in Examples 1 and 7, except that compound E18 illustrated below was used in place of E16.

[Chem. 47]

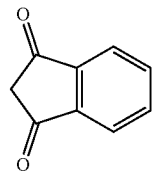

E18

Mass spectrometry of the product revealed a molecular ion peak at m/z 524, corresponding to M+ of exemplified compound B16.

As with Example 1, the measurement of the absorption spectrum of exemplified compound B16 in a dilute chloroform solution revealed that the maximum absorption wavelength in the visible light region was 569 nm. The molar extinction coefficient in the dilute chloroform solution was measured and found to be 65,670 $M^{-1}cm^{-1}$ at a wavelength of 569 nm.

DSC measurement of exemplified compound B16 revealed a melting point of 308° C.

As with Example 1, Δtemperature was calculated from the melting point and the sublimation temperature and is presented in Table 7.

Example 10

Exemplified Compound B17

Exemplified compound B17 was synthesized as in Examples 1 and 7, except that compound E19 illustrated below was used in placed of E7 and that compound E18 illustrated below was used in place of E16.

[Chem. 48]

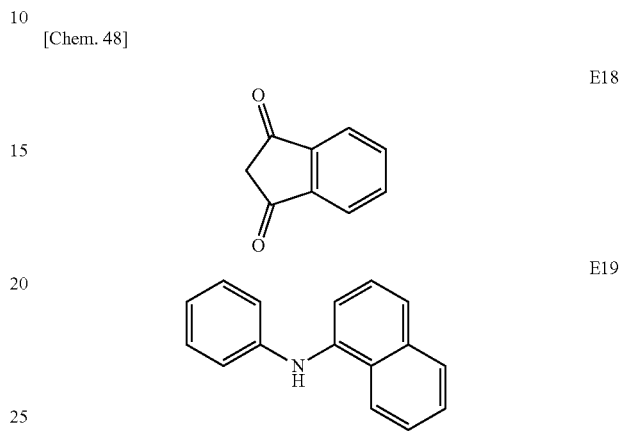

Mass spectrometry of the product revealed a molecular ion peak at m/z 574, corresponding to M+ of exemplified compound B17.

As with Example 1, Δtemperature was calculated from the melting point and the sublimation temperature and is presented in Table 7.

Example 11

Exemplified Compound B20

Exemplified compound B20 was synthesized as in Examples 1 and 7, except that compound E17 illustrated below was used in place of E7 and that compound E18 was used in placed of E16.

[Chem. 49]

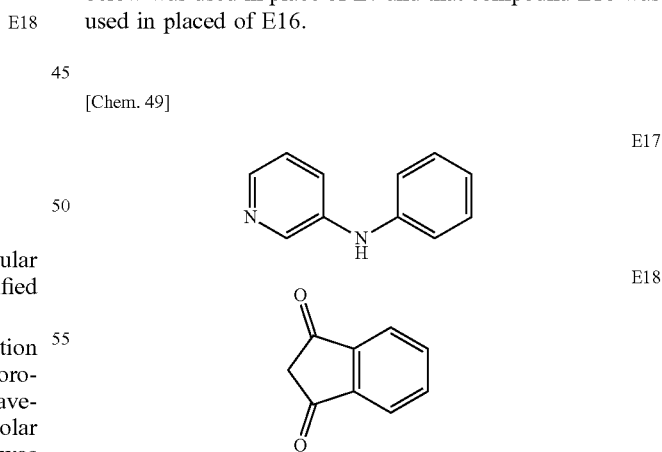

Mass spectrometry of the product revealed a molecular ion peak at m/z 525, corresponding to M+ of exemplified compound B20.

As with Example 1, Δtemperature was calculated from the melting point and the sublimation temperature and is presented in Table 7.

Example 12

Exemplified Compound B25

Exemplified compound B25 was synthesized as in Examples 1 and 7, except that compound E20 illustrated below was used in place of E7 and that compound E18 was used in place of E16.

[Chem. 50]

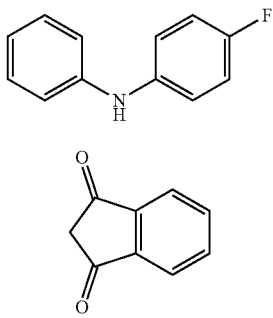

E20

E18

Mass spectrometry of the product revealed a molecular ion peak at m/z 542, corresponding to M+ of exemplified compound B25.

As with Example 1, Δtemperature was calculated from the melting point and the sublimation temperature and is presented in Table 7.

Example 13

Exemplified Compound B32

Exemplified compound B32 was synthesized as in Examples 1 and 7, except that compound E21 illustrated below was used in place of E16.

[Chem. 51]

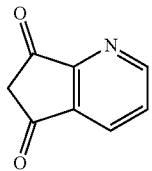

E21

Mass spectrometry of the product revealed a molecular ion peak at m/z 525, corresponding to M+ of exemplified compound B32.

As with Example 1, Δtemperature was calculated from the melting point and the sublimation temperature and is presented in Table 7.

Example 14

Exemplified Compound B41

Exemplified compound B41 was synthesized as in Examples 1 and 7, except that compound E22 illustrated below was used in place of E16.

[Chem. 52]

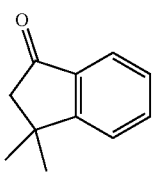

E22

Mass spectrometry of the product revealed a molecular ion peak at m/z 538, corresponding to M+ of exemplified compound B41.

As with Example 1, Δtemperature was calculated from the melting point and the sublimation temperature and is presented in Table 7.

Example 15

Exemplified Compound C5

Exemplified compound C5 was synthesized as in Examples 1 and 7, except that compound E23 illustrated below was used in place of E2.

[Chem. 53]

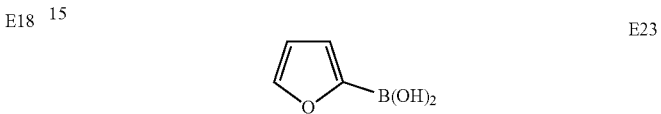

E23

Mass spectrometry of the product revealed a molecular ion peak at m/z 544, corresponding to M+ of exemplified compound C5.

As with Example 1, Δtemperature was calculated from the melting point and the sublimation temperature and is presented in Table 7.

Example 16

Exemplified Compound C10

Exemplified compound C5 was synthesized as in Examples 1 and 15, except that compound E18 illustrated below was used in place of E16.

[Chem. 54]

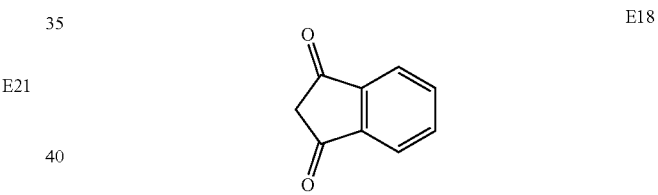

E18

Mass spectrometry of the product revealed a molecular ion peak at m/z 508, corresponding to M+ of exemplified compound C10.

As with Example 1, Δtemperature was calculated from the melting point and the sublimation temperature and is presented in Table 7.

Example 17

Exemplified Compound AA1

[Chem. 55]

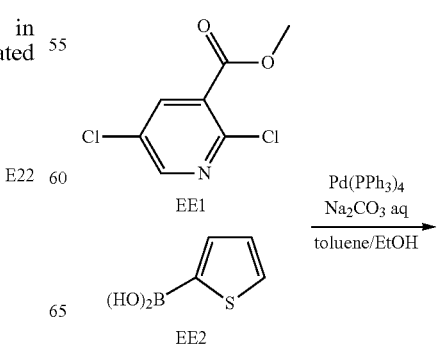

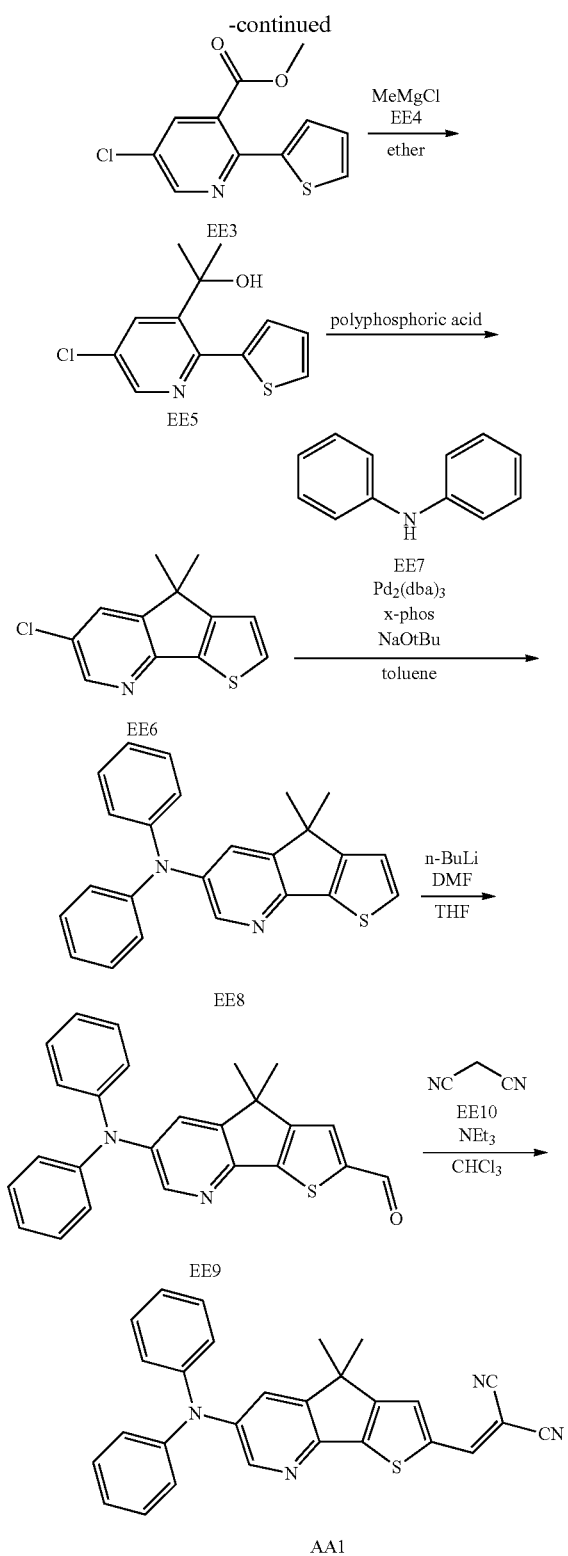

extract was concentrated and purified by silica-gel column chromatography (mobile phase: toluene) to give 5.3 g of pale yellow solid EE3 (yield: 86%).

To 100 ml of tetrahydrofuran, 5.3 g (20.9 mmol) of EE3 was added. Then 20.9 ml (62.7 mmol) of EE4 (3.0 M tetrahydrofuran solution) was added dropwise thereto at 30° C. The mixture was heated to reflux with stirring for 3 hours. After the reaction, the mixture was cooled to 0° C. Ethanol, water, and dilute hydrochloric acid were added thereto in this order. The mixture was subjected to extraction with ethyl acetate. After concentration, the residue was purified by silica-gel column chromatography (mobile phase: toluene:ethyl acetate=20:1) to give 3.3 g of pale yellow solid EE5 (yield: 62%).

To 30 ml of polyphosphoric acid, 2.5 g (9.9 mmol) of EE5 was added. The mixture was stirred at 100° C. for 3 hours. After the reaction, water was added thereto. The mixture was subjected to extraction with chloroform. After concentration, the residue was purified by silica-gel column chromatography (mobile phase: heptane:ethyl acetate=10:1) to give 960 mg of pale yellow solid EE6 (yield: 42%).

To 5 ml of toluene, 160 mg (0.2 mmol) of tris(dibenzylideneacetone)dipalladium(0) and 250 mg (0.5 mmol) of x-phos were added. The mixture was stirred for 15 minutes at room temperature. The resulting solution was added to 12 ml of a separately prepared toluene solution containing 820 mg (3.5 mmol) of EE6 and 650 mg (3.8 mmol) of EE7 dissolved therein. Then 670 mg (7.0 mmol) of sodium tert-butoxide was added thereto. The mixture was stirred at 120° C. for 3 hours. After cooling, the mixture was filtered with Celite. The extract was concentrated. The residue was purified by silica-gel column chromatography (mobile phase: toluene:ethyl acetate=20:1) to give 760 mg of white solid EE8 (yield: 59%).

To 20 ml of tetrahydrofuran, 750 mg (2.0 mmol) of EE8 was added. The mixture was cooled to −40° C. Then 2.8 ml (4.5 mmol) of n-butyllithium (1.6 M n-hexane solution) was added dropwise thereto at −40° C. The mixture was stirred for 2 hours at the temperature. Then 0.5 ml (6.1 mmol) of DMF was added dropwise at −40° C. The mixture was stirred for 3 hours while being slowly brought to room temperature. After the reaction, an aqueous solution of ammonium chloride was added thereto. The mixture was subjected to extraction with ethyl acetate. After concentration, the residue was purified by silica-gel column chromatography (mobile phase: toluene:ethyl acetate=15:1) to give 240 mg of yellow solid EE9 (yield: 30%).

To 10 ml of chloroform, 200 mg (0.5 mmol) of E9 was added. Then 100 mg (1.5 mmol) of EE10 and six drops of triethylamine were added thereto. The mixture was stirred for 2 hours. After the reaction, the mixture was subjected to extraction with chloroform. After concentration, the residue was purified by silica-gel column chromatography (mobile phase: chloroform:ethyl acetate=20:1) to give 170 mg of dark red solid AA1 (yield: 77%). Mass spectrometry of the product revealed a molecular ion peak at m/z 445, corresponding to M+ of exemplified compound AA1.

As with Example 1, Δtemperature was calculated from the melting point and the sublimation temperature and is presented in Table 7.

First, 5.0 g (24.3 mmol) of EE1 and 4.7 g (36.4 mmol) of EE2 were added to 30 ml of toluene, 15 ml of ethanol, and 45 ml of 20% by mass aqueous solution of sodium carbonate. Then 840 mg (0.7 mmol) of tetrakis(triphenylphosphine)palladium(0) was added thereto. The mixture was heated to 90° C. and stirred for 6 hours. After cooling, the mixture was subjected to extraction with toluene. The Example 18

Exemplified Compound AA2

Exemplified compound AA2 was synthesized as in Example 17, except that compound EE11 illustrated below was used in place of EE7.

[Chem. 56]

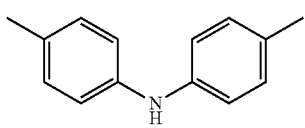

EE11

Mass spectrometry of the product revealed a molecular ion peak at m/z 473, corresponding to M+ of exemplified compound AA2.

As with Example 1, Δtemperature was calculated from the melting point and the sublimation temperature and is presented in Table 7.

Example 19

Exemplified Compound BB1
The same synthesis procedure as in Example 17 was performed up to the production of compound EE9.

[Chem. 57]

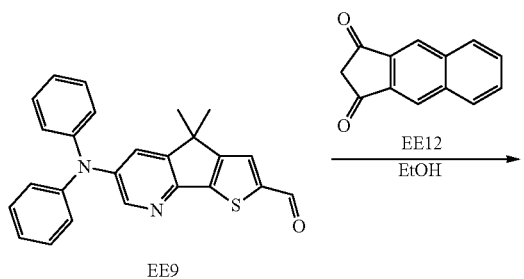

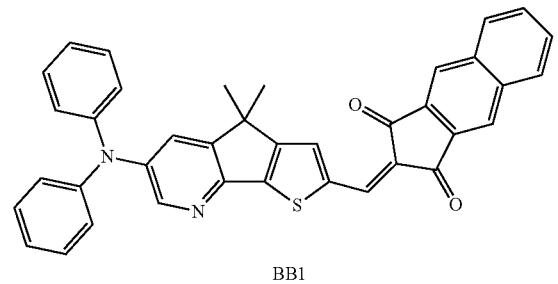

BB1

To 40 ml of ethanol, 200 mg (0.5 mmol) of EE9 was added. Then 110 mg (0.6 mmol) of EE12 was added thereto. The mixture was heated to 90° C. with stirring for 3 hours. After the reaction, the mixture was filtered. The residue was purified by silica-gel column chromatography (mobile phase: chloroform) to give 200 mg of black solid BB1 (yield: 68%).

Mass spectrometry of the product revealed a molecular ion peak at m/z 575, corresponding to M+ of exemplified compound BB1.

As with Example 1, Δtemperature was calculated from the melting point and the sublimation temperature and is presented in Table 7.

Example 20

Exemplified Compound BB13
The same synthesis procedure as in Example 17 was performed up to the production of compound EE9.

[Chem. 58]

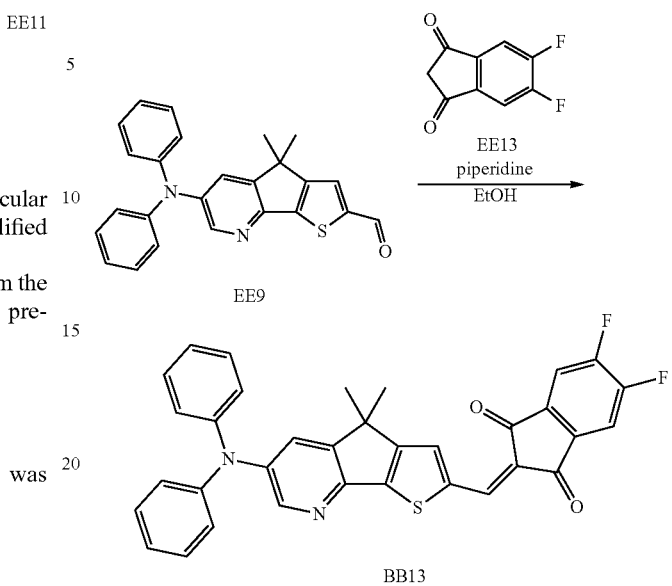

BB13

To 40 ml of ethanol, 200 mg (0.5 mmol) of EE9 was added. Then 100 mg (0.6 mmol) of EE13 and 0.1 ml of piperidine were added thereto. The mixture was heated to 90° C. with stirring for 5 hours. After the reaction, the mixture was filtered. The residue was purified by silica-gel column chromatography (mobile phase: chloroform) to give 190 mg of black solid BB13 (yield: 68%).

Mass spectrometry of the product revealed a molecular ion peak at m/z 561, corresponding to M+ of exemplified compound BB13.

As with Example 1, Δtemperature was calculated from the melting point and the sublimation temperature and is presented in Table 7.

Example 21

Exemplified Compound BB22
Exemplified compound BB22 was synthesized as in Examples 17 and 20, except that compound EE14 illustrated below was used in place of EE13.

[Chem. 59]

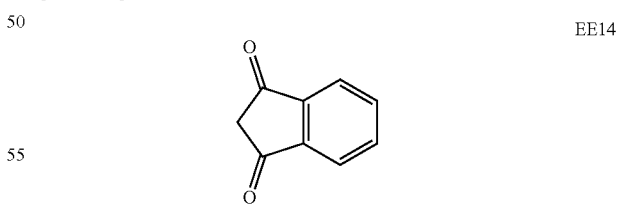

Mass spectrometry of the product revealed a molecular ion peak at m/z 525, corresponding to M+ of exemplified compound BB22.

As with Example 1, the measurement of the absorption spectrum of exemplified compound BB22 in a dilute chloroform solution revealed that the maximum absorption wavelength in the visible light region was 549 nm. DSC measurement of exemplified compound BB22 was performed in a nitrogen atmosphere at a rate of temperature increase of 10° C./min and revealed a melting point of 295° C. As an instrument, DSC 204 F1 available from NETZSCH was used.

As with Example 1, Δtemperature was calculated from the melting point and the sublimation temperature and is presented in Table 7.

Example 22

Exemplified Compound BB25

Exemplified compound BB25 was synthesized as in Examples 17 and 20, except that compound EE11 illustrated below was used in place of EE7 and that compound E14 illustrated below was used in place of EE13.

[Chem. 60]

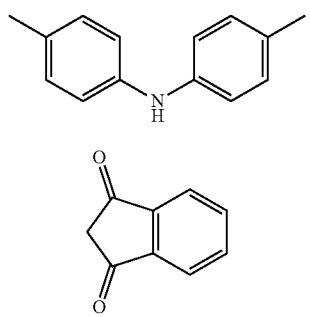

EE11

EE14

Mass spectrometry of the product revealed a molecular ion peak at m/z 553, corresponding to M+ of exemplified compound BB25.

As with Example 1, Δtemperature was calculated from the melting point and the sublimation temperature and is presented in Table 7.

Example 23

Exemplified Compound BB29

Exemplified compound BB29 was synthesized as in Examples 17 and 20, except that compound EE15 illustrated below was used in place of EE1 and that compound EE16 was used in placed of EE7.

[Chem. 61]

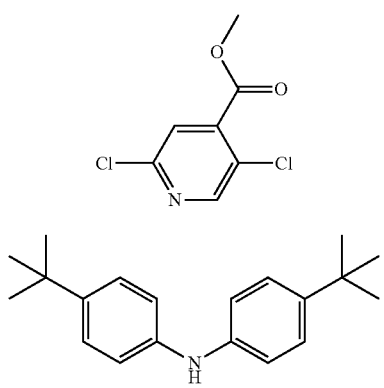

EE15

EE16

Mass spectrometry of the product revealed a molecular ion peak at m/z 637, corresponding to M+ of exemplified compound BB29.

As with Example 1, Δtemperature was calculated from the melting point and the sublimation temperature and is presented in Table 7.

Example 24

Exemplified Compound BB30

Exemplified compound BB30 was synthesized as in Examples 17 and 20, except that compound EE17 illustrated below was used in place of EE1 and that compound EE16 was used in place of EE7.

[Chem. 62]

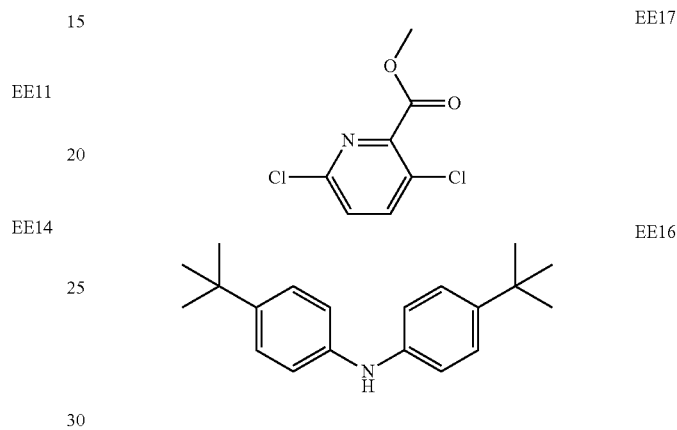

EE17

EE16

Mass spectrometry of the product revealed a molecular ion peak at m/z 637, corresponding to M+ of exemplified compound BB30.

As with Example 1, Δtemperature was calculated from the melting point and the sublimation temperature and is presented in Table 7.

Example 25

Exemplified Compound BB41

Exemplified compound BB41 was synthesized as in Examples 17 and 20, except that compound EE18 was used in place of EE13.

[Chem. 63]

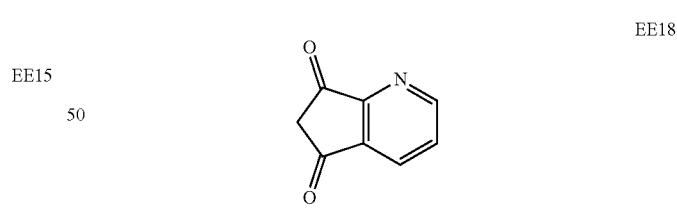

EE18

Mass spectrometry of the product revealed a molecular ion peak at m/z 526, corresponding to M+ of exemplified compound BB41.

As with Example 1, Δtemperature was calculated from the melting point and the sublimation temperature and is presented in Table 7.

Example 26

Exemplified Compound CC6

Exemplified compound CC6 was synthesized as in Examples 17 and 20, except that compound EE19 illustrated below was used in place of EE2.

[Chem. 64]

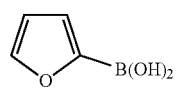

EE19

Mass spectrometry of the product revealed a molecular ion peak at m/z 545, corresponding to M+ of exemplified compound C5.

As with Example 1, Δtemperature was calculated from the melting point and the sublimation temperature and is presented in Table 7.

Example 27

Exemplified Compound CC9

Exemplified compound C5 was synthesized as in Examples 17 and 20, except that compound EE19 illustrated below was used in place of EE2 and that compound E14 was used in place of EE13.

[Chem. 65]

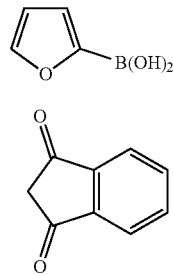

EE19

E14

Mass spectrometry of the product revealed a molecular ion peak at m/z 509, corresponding to M+ of exemplified compound C10.

As with Example 1, Δtemperature was calculated from the melting point and the sublimation temperature and is presented in Table 7.

Example 28

Exemplified Compound A6

Exemplified compound A6 was synthesized as in Example 1, except that compound E12 illustrated below was used in place of E7.

[Chem. 66]

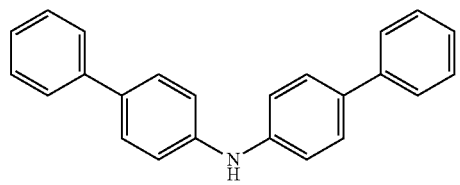

E27

Mass spectrometry of the product revealed a molecular ion peak at m/z 596, corresponding to M+ of exemplified compound A6.

As with Example 1, Δtemperature was calculated from the melting point and the sublimation temperature and is presented in Table 7.

Example 29

Exemplified Compound A23

Exemplified compound A23 was synthesized as in Example 1, except that compound E28 illustrated below was used in place of E7.

[Chem. 67]

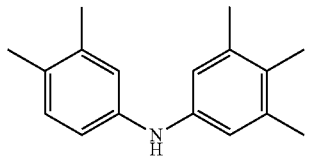

E28

Mass spectrometry of the product revealed a molecular ion peak at m/z 514, corresponding to M+ of exemplified compound A23.

As with Example 1, Δtemperature was calculated from the melting point and the sublimation temperature and is presented in Table 7.

Example 30

Exemplified Compound A25

Exemplified compound A25 was synthesized as in Example 1, except that compound E29 illustrated below was used in place of E7.

[Chem. 68]

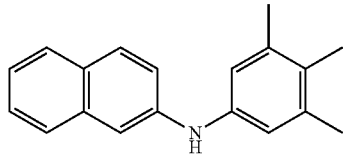

E29

Mass spectrometry of the product revealed a molecular ion peak at m/z 536, corresponding to M+ of exemplified compound A25.

As with Example 1, Δtemperature was calculated from the melting point and the sublimation temperature and is presented in Table 7.

Example 31

Exemplified Compound A29

Exemplified compound A29 was synthesized as in Example 1, except that compound E30 illustrated below was used in place of E7.

[Chem. 69]

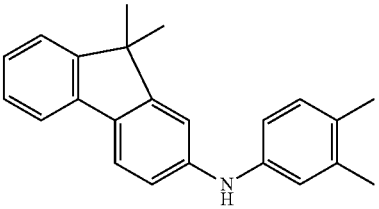

E30

Mass spectrometry of the product revealed a molecular ion peak at m/z 588, corresponding to M+ of exemplified compound A29.

As with Example 1, Δtemperature was calculated from the melting point and the sublimation temperature and is presented in Table 7.

Example 32

Exemplified Compound A32
Exemplified compound A32 was synthesized as in Example 1, except that compound E31 illustrated below was used in place of E7.

[Chem. 70]

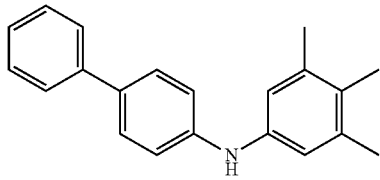

E31

Mass spectrometry of the product revealed a molecular ion peak at m/z 562, corresponding to M+ of exemplified compound A32.

As with Example 1, Δtemperature was calculated from the melting point and the sublimation temperature and is presented in Table 7.

Example 33

Exemplified Compound A32
Exemplified compound A32 was synthesized as in Example 1, except that compound E31 illustrated below was used in place of E7.

[Chem. 71]

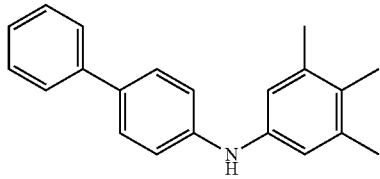

E31

Mass spectrometry of the product revealed a molecular ion peak at m/z 562, corresponding to M+ of exemplified compound A32.

As with Example 1, Δtemperature was calculated from the melting point and the sublimation temperature and is presented in Table 7.

Example 34

Exemplified Compound A34
An intermediate E32 was synthesized according to a scheme illustrated below.

[Chem. 72]

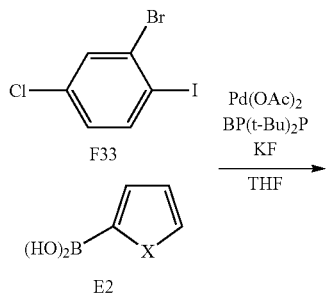

-continued

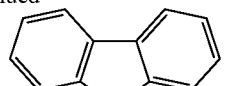

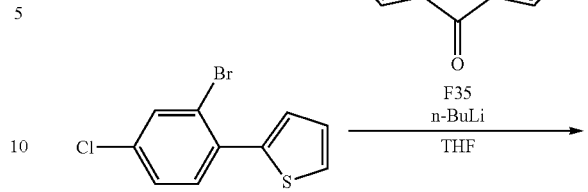

To 50 ml of tetrahydrofuran, 5.0 g (15.8 mmol) of F33 and 2.4 g (19.0 mmol) of E2 were added. Then 70 mg (0.3 mmol) of palladium(II) acetate and 190 mg (0.6 mmol) of (2-biphenyl)di-tert-butylphosphine, and 2.8 g of (47.3 mmol) of potassium fluoride were added thereto. The mixture was stirred at room temperature for 7 hours. After cooling, the mixture was subjected to ethyl acetate. The extract was concentrated and purified by silica-gel column chromatography (mobile phase: heptane) to give 1.9 g of clear, colorless liquid F34 (yield: 44%).

To 80 ml of tetrahydrofuran, 1.9 g (6.9 mmol) of F34 was added. The mixture was cooled to −78° C. Then 4.8 ml (7.6 mmol) of n-butyllithium (1.6 M hexane solution) was added dropwise at −78° C. The mixture was stirred for 30 minutes. Next, 1.4 g (7.6 mmol) of F35 dissolved in 10 ml of a tetrahydrofuran solution was added dropwise at −78° C. The reaction was performed for 1 hour. The mixture was brought to room temperature over a period of 1 hour. After the reaction, water was added thereto. The mixture was subjected to extraction with ethyl acetate. The extract was concentrated and purified by silica-gel column chromatography (mobile phase: heptane:ethyl acetate=10:1) to give 1.2 g of clear, colorless liquid F36 (yield: 48%).

To 60 ml of acetic acid, 1.2 g (3.3 mmol) of F36 was added. Then 1.2 ml of 10% hydrochloric acid was added dropwise at 0° C. The mixture was stirred for 60 minutes at the temperature. After the reaction, an aqueous solution of sodium hydrogen carbonate was added thereto. The mixture was subjected to extraction with dichloromethane. After concentration, the residue was purified by silica-gel column chromatography (mobile phase: heptane) to give 0.4 g of white solid F32 (yield: 35%). Exemplified compound A34 was synthesized as in Example 1, except that compound F32 described above was used in place of E6 and that E11 was used in place of E7.

Mass spectrometry of the product revealed a molecular ion peak at m/z 594, corresponding to M+ of exemplified compound A34.

As with Example 1, Δtemperature was calculated from the melting point and the sublimation temperature and is presented in Table 7.

Example 35

Exemplified Compound B58

Exemplified compound B58 was synthesized as in Examples 1, 7, and 34, except that F32 was used in place of E6 and that E18 was used in place of E16.

Mass spectrometry of the product revealed a molecular ion peak at m/z 646, corresponding to M+ of exemplified compound B58.

As with Example 1, Δtemperature was calculated from the melting point and the sublimation temperature and is presented in Table 7.

Example 36

Exemplified Compound B68

Exemplified compound 68 was synthesized as in Examples 1 and 7, except that compound F37 illustrated below was used in place of E16.

[Chem. 73]

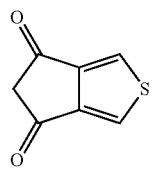

F37

Mass spectrometry of the product revealed a molecular ion peak at m/z 530, corresponding to M+ of exemplified compound B68.

As with Example 1, Δtemperature was calculated from the melting point and the sublimation temperature and is presented in Table 7.

Comparative Example 1

Comparative Compound a-1

The same synthesis procedure as in Example 1 was performed up to the production of compound E9.

[Chem. 74]

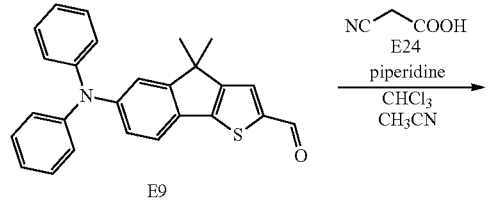

E9

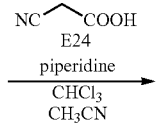

E24
piperidine
CHCl₃
CH₃CN

-continued

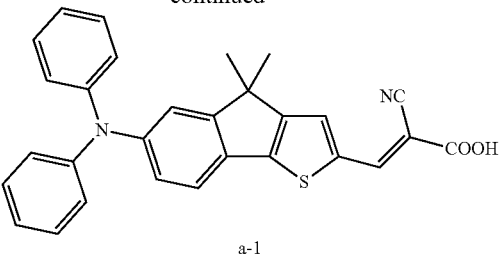

a-1

To a solvent mixture of 30 ml of chloroform and 90 ml of acetonitrile, 500 mg (1.3 mmol) of E9 was added. Then 332 mg (3.9 mmol) of E24 and 0.1 ml of piperidine were added thereto. The mixture was heated to 90° C. with stirring for 6 hours. After the reaction, the mixture was filtered. The residue was purified by silica-gel column chromatography (mobile phase: chloroform:ethyl acetate=20:1) to give 450 mg of red-orange solid a-1 (yield: 75%).

Mass spectrometry of the product revealed a molecular ion peak at m/z 463, corresponding to M+ of comparative compound a-1.

As with Example 1, the measurement of the absorption spectrum of comparative compound a-1 in a dilute chloroform solution revealed that the maximum absorption wavelength in the visible light region was 481 nm. The results indicate that the comparative compound has a maximum absorption wavelength of 500 nm or less and thus low panchromatic performance as described above.

TG-DTA measurement of comparative compound a-1 revealed a decomposition temperature (temperature at which the mass is decreased by 1%) of 189° C.

Although an attempt was made to subject comparative compound a-1 to sublimation purification, the comparative compound did not sublime because of thermal decomposition.

Comparative Example 2

Comparative Compound a-2

Comparative compound a-2 was synthesized as in Example 1, except that compound E25 illustrated below was used in place of E9.

[Chem. 75]

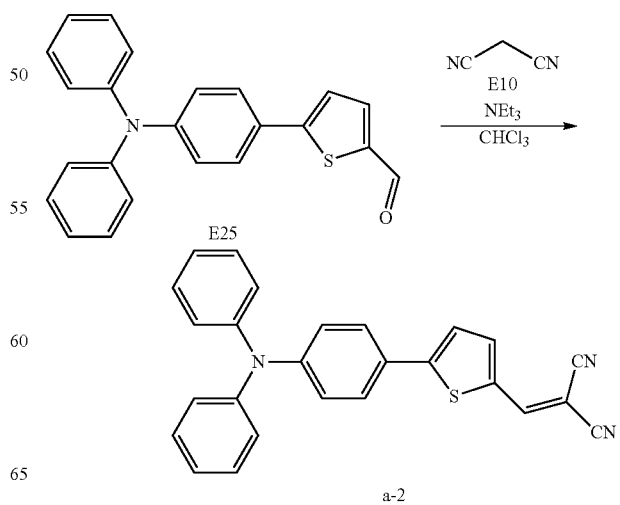

a-2

Mass spectrometry of the product revealed a molecular ion peak at m/z 404, corresponding to M+ of comparative compound a-2.

As with Example 1, the measurement of the absorption spectrum of comparative compound a-2 in a dilute chloroform solution revealed that the maximum absorption wavelength in the visible light region was 507 nm. The molar extinction coefficient in the dilute chloroform solution was measured and found to be 37,600 $M^{-1}cm^{-1}$ at a wavelength of 507 nm.

DSC measurement of comparative compound a-2 revealed a melting point of 180° C.

As with Example 1, Δtemperature was calculated from the melting point and the sublimation temperature and is presented in Table 5.

Comparative Example 3

Comparative Compound b-1

Comparative compound b-1 was synthesized as in Examples 1 and 7, except that compound E26 illustrated below was used in place of E9 and that E18 was used in place of E16.

[Chem. 76]

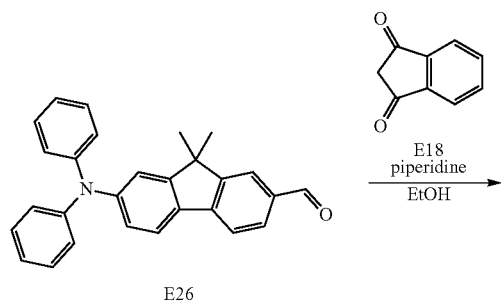

[Chem. 77]

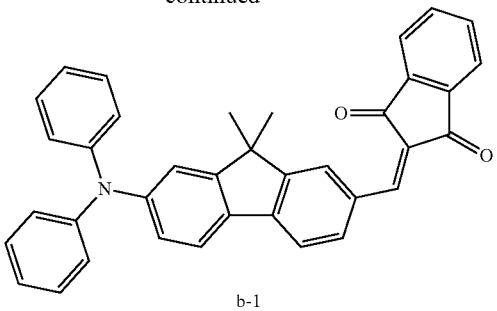

b-1

Mass spectrometry of the product revealed a molecular ion peak at m/z 517, corresponding to M+ of comparative compound a-2.

As with Example 1, the measurement of the absorption spectrum of comparative compound a-2 in a dilute chloroform solution revealed that the maximum absorption wavelength in the visible light region was 510 nm. DSC measurement of comparative compound a-2 revealed a melting point of 262° C.

As with Example 1, Δtemperature was calculated from the melting point and the sublimation temperature and is presented in Table 5.

Examples 38 to 98 and Comparative Examples 4 to 6

In each of the examples, a photoelectric conversion element was produced in which a hole-collecting electrode, an electron-blocking layer, a photoelectric conversion layer, a hole-blocking layer, and an electron-collecting electrode were stacked on a substrate.

First, an IZO film was formed on a Si substrate and subjected to desired patterning to form an IZO electrode (hole-collecting electrode). The IZO electrode had a thickness of 100 nm. The resulting substrate including the TiN electrode formed in this way was used as an IZO substrate in subsequent steps.

An organic compound layer and an electrode layer presented in Table 2 were sequentially formed on the IZO substrate. In this case, an opposite electrode (electron-collecting electrode) had an electrode area of 3 $mm^2$. One of compounds Y1 to Y4 illustrated below was used for the electron-blocking layer Z1.

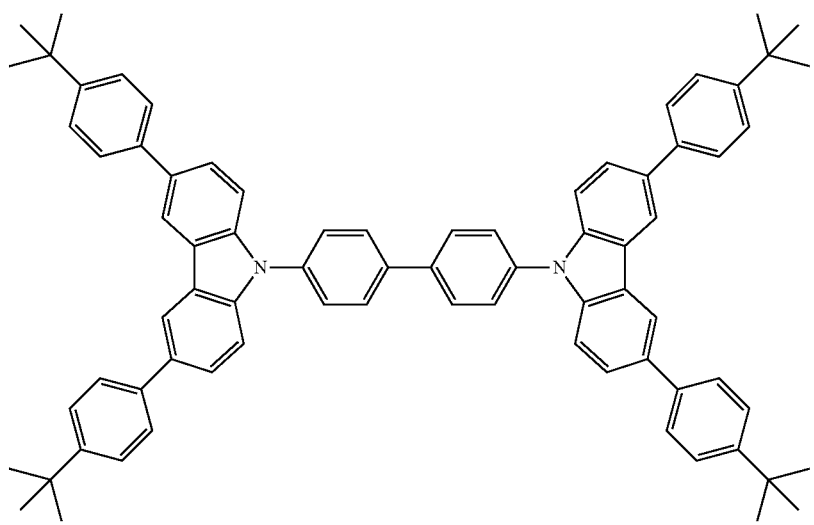

-continued

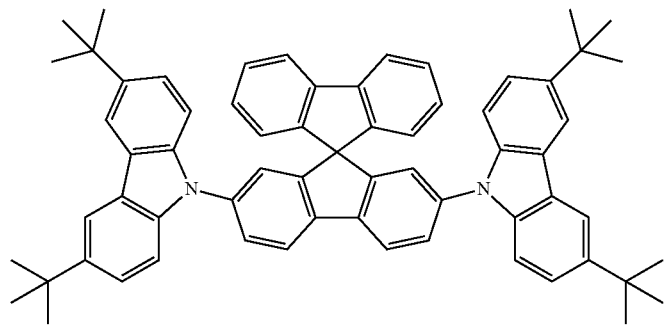

Y2

Y3

As a photoelectric conversion-inducing material Z3, fullerene C60 (C60), fullerene C70 (C70), or DCV3T was used.

[Chem. 78]

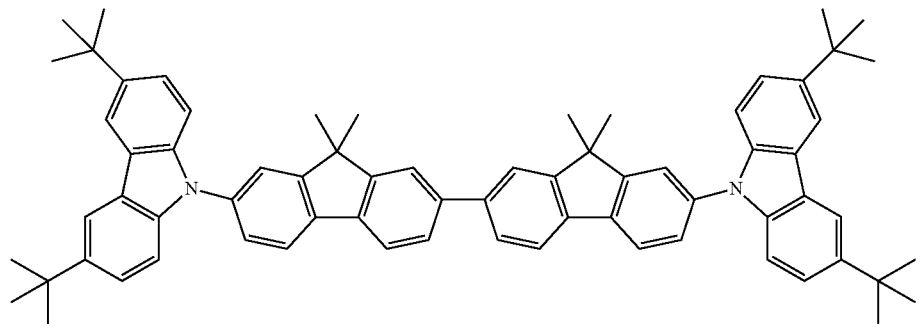

DCV3T

TABLE 6

| | Material | Thickness (nm) |
|---|---|---|
| Electron-blocking layer | Z1 | 50 |
| Photoelectric conversion layer | Z2 (light-absorbing material)<br>Z3 (photoelectric conversion-inducing material)<br>(Z2:Z3 = 30:70 (ratio by weight)) | 200 |
| Hole-blocking layer | fullerene C60 | 10 |
| Electron-collecting electrode layer | IZO | 30 |

The characteristics of the resulting photoelectric conversion elements were measured and evaluated. A current was measured when a voltage of 5 V was applied to each of the elements. In any of these elements, (current in light place)/(current in dark place)=100 or more, which indicated that the photoelectric conversion element functioned.

The external quantum efficiency of each photoelectric conversion element produced as described above was measured while a voltage of 5 V was applied between the hole-collecting electrode and the electron-collecting electrode. The external quantum efficiency was calculated by measuring photocurrent density when each element was irradiated with monochromatic light having a wavelength of 450 nm (blue light), 550 nm (green light), or 625 nm (red light) and having an intensity of 50 $\mu W/cm^2$. The photocurrent density was determined by subtracting the dark current density in the dark from the current density at the time of light irradiation. The monochromatic light used for the measurement was obtained by monochromatizing white light emitted from a xenon lamp (Model XB-50101AA-A, available from Ushio, Inc.) with a monochromator (Model MC-10N, available from Ritu Oyo Kougaku Co., Ltd).

The application of voltage to the elements and the measurement of current were performed with a source meter (Model R6243, available from Advantest Corporation). In the measurement of the external quantum efficiency, light is perpendicularly incident on the elements from the upper electrode side. Table 7 presents the results. In Table 7, the external quantum efficiency was evaluated as described below in order to compare panchromatic performance.

⊙: External quantum efficiency during irradiation with blue or red light/external quantum efficiency during irradiation with green light ≥0.7

○: External quantum efficiency during irradiation with blue or red light/external quantum efficiency during irradiation with green light ≥0.5

×: External quantum efficiency during irradiation with blue or red light/external quantum efficiency during irradiation with green light <0.5

TABLE 7

| | Δ | | | | External quantum efficiency | |
|---|---|---|---|---|---|---|
| | Temperature | Z1 | Z2 | Z3 | Blue/green | Red/green |
| Example 38 | ○ | Y1 | Exemplified compound A1 | C60 | ⊙ | ○ |
| Example 39 | ○ | Y2 | Exemplified compound A1 | C60 | ⊙ | ○ |
| Example 40 | ○ | Y3 | Exemplified compound A1 | C60 | ⊙ | ○ |
| Example 41 | ○ | Y2 | Exemplified compound A1 | C70 | ⊙ | ○ |
| Example 42 | ○ | Y2 | Exemplified compound A2 | C60 | ⊙ | ⊙ |
| Example 43 | ○ | Y2 | Exemplified compound A4 | C60 | ⊙ | ○ |
| Example 44 | ○ | Y2 | Exemplified compound A10 | C60 | ⊙ | ○ |
| Example 45 | ○ | Y2 | Exemplified compound B1 | C60 | ⊙ | ⊙ |
| Example 46 | ○ | Y3 | Exemplified compound B1 | C70 | ⊙ | ⊙ |
| Example 47 | ○ | Y2 | Exemplified compound B2 | C70 | ⊙ | ⊙ |
| Example 48 | ⊙ | Y1 | Exemplified compound B10 | C60 | ⊙ | ⊙ |
| Example 49 | ⊙ | Y2 | Exemplified compound B10 | C60 | ⊙ | ⊙ |
| Example 50 | ⊙ | Y3 | Exemplified compound B10 | C60 | ⊙ | ⊙ |
| Example 51 | ⊙ | Y3 | Exemplified compound B10 | C70 | ⊙ | ⊙ |
| Example 52 | ○ | Y2 | Exemplified compound B11 | C60 | ⊙ | ⊙ |
| Example 53 | ⊙ | Y2 | Exemplified compound B16 | C60 | ⊙ | ⊙ |
| Example 54 | ⊙ | Y3 | Exemplified compound B16 | C60 | ⊙ | ⊙ |
| Example 55 | ⊙ | Y2 | Exemplified compound B17 | C60 | ⊙ | ⊙ |
| Example 56 | ⊙ | Y3 | Exemplified compound B17 | C60 | ⊙ | ⊙ |
| Example 57 | ○ | Y2 | Exemplified compound B20 | C60 | ⊙ | ○ |
| Example 58 | ⊙ | Y2 | Exemplified compound B25 | C60 | ⊙ | ⊙ |
| Example 59 | ⊙ | Y3 | Exemplified compound B25 | C60 | ⊙ | ⊙ |
| Example 60 | ⊙ | Y2 | Exemplified compound B32 | C60 | ⊙ | ⊙ |
| Example 61 | ⊙ | Y3 | Exemplified compound B32 | C70 | ⊙ | ⊙ |
| Example 62 | ⊙ | Y2 | Exemplified compound B41 | C60 | ⊙ | ○ |
| Example 63 | ⊙ | Y3 | Exemplified compound C5 | C60 | ⊙ | ⊙ |
| Example 64 | ⊙ | Y3 | Exemplified compound C10 | C70 | ⊙ | ⊙ |
| Example 65 | ⊙ | Y3 | Exemplified compound B10 | DCV3T | ⊙ | ⊙ |
| Example 66 | ⊙ | Y3 | Exemplified compound B16 | DCV3T | ⊙ | ⊙ |
| Example 67 | ○ | Y3 | Exemplified compound AA1 | C60 | ⊙ | ○ |
| Example 68 | ○ | Y2 | Exemplified compound AA2 | C60 | ⊙ | ○ |
| Example 69 | ○ | Y2 | Exemplified compound BB1 | C60 | ⊙ | ⊙ |
| Example 70 | ○ | Y3 | Exemplified compound BB1 | C70 | ⊙ | ⊙ |
| Example 71 | ⊙ | Y3 | Exemplified compound BB13 | C60 | ⊙ | ⊙ |
| Example 72 | ⊙ | Y3 | Exemplified compound BB13 | C70 | ⊙ | ⊙ |
| Example 73 | ⊙ | Y2 | Exemplified compound BB22 | C60 | ⊙ | ⊙ |
| Example 74 | ⊙ | Y3 | Exemplified compound BB22 | C60 | ⊙ | ⊙ |
| Example 75 | ⊙ | Y3 | Exemplified compound BB22 | C70 | ⊙ | ⊙ |
| Example 76 | ○ | Y2 | Exemplified compound BB25 | C60 | ⊙ | ⊙ |
| Example 77 | ○ | Y3 | Exemplified compound BB25 | C60 | ⊙ | ⊙ |
| Example 78 | ⊙ | Y2 | Exemplified compound BB29 | C60 | ⊙ | ⊙ |

From the results described above, the compounds according to the present invention have high vapor deposition stability and high photoelectric conversion efficiency. Specifically, good external quantum efficiency is provided in all of the blue region (wavelength: about 450 nm), the green region (wavelength: about 550 nm), and the red region (wavelength: about 625 nm). This is attributed to the fact that the light-absorbing materials contained in the photoelectric conversion elements of the present invention have high thermal stability and high vapor deposition stability and, in addition, have absorption sensitivity in the entire visible light region and strong absorption even in the red region.

In contrast, the compounds used in the comparative examples have low vapor deposition stability and low conversion efficiency in the red region.

As described above with reference to these examples, the use of the photoelectric conversion layer containing the organic compound according to the present invention results in efficient photoelectric conversion in the entire visible light region. Furthermore, the photoelectric conversion element can be produced by a stable vapor deposition process.

The present invention is not limited to the foregoing embodiments. Various changes and modifications may be made without departing from the spirit and scope of the invention. Therefore, the following claims are attached in order to make the scope of the present invention public.

According to the present invention, the organic compound having broad absorption in the visible light region and good thermal stability can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An organic compound represented by general formula [1]:

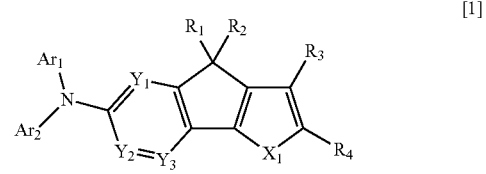

where in general formula [1], $Ar_1$ and $Ar_2$ are each independently selected from the group consisting of an aryl group and a heteroaryl group, Ar$_1$ and Ar$_2$ each optionally have a halogen atom, a cyano group, an alkyl group, an alkoxy group, an aryl group, or a heteroaryl group as a substituent, the substituent optionally further has a halogen atom, a cyano group, an alkyl group, or an alkoxy group as a substituent, Ar$_1$ and Ar$_2$ are optionally combined with each other to form a ring, wherein in general formula [1], R$_1$ and R$_2$ are each independently selected from the group consisting of a hydrogen atom, a halogen atom, a cyano group, an alkyl group, an aryl group, and a hetero aryl group, the alkyl group optionally has a halogen atom as a substituent, each of the aryl group and the heteroaryl group each denoted by R$_1$ or R$_2$ optionally further has a halogen atom, a cyano group, an alkyl group, or an alkoxy group as a substituent, R$_1$ and R$_2$ are optionally combined with each other to form a ring, wherein in general formula [1], R$_3$ is selected from the group consisting of a hydrogen atom, a halogen atom, a cyano group, and an alkyl group, the alkyl group optionally has a halogen atom as a substituent, wherein in general formula [1], X$_1$ is oxygen or sulfur, wherein in general formula [1], each of Y$_1$ to Y$_3$ is a carbon atom or a nitrogen atom, and Y$_1$ to Y$_3$ optionally is the same or different, wherein when at least one of Y$_1$ to Y$_3$ is a carbon atom, the carbon atom optionally has a hydrogen atom, a halogen atom, a cyano group, or an alkyl group as a substituent, the alkyl group optionally has a halogen atom as a substituent, wherein in general formula [1], R$_4$ is represented by general formula [1-1] or general formula [1-2], each * indicates a bonding position,

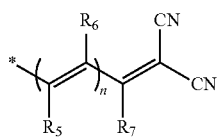

[1-1]

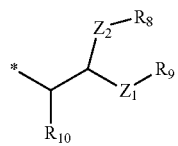

[1-2]

where in general formulae [1-1] and [1-2], R$_5$ to R$_{10}$ are each independently selected from the group consisting of a hydrogen atom, a cyano group, an amino group, an amide group, an alkyl group, an alkenyl group, an alkynyl group, an aryl group and a hetero aryl group, R$_5$ and R$_7$ are optionally combined with each other to form a ring, R$_8$ and R$_9$ are optionally combined with each other to form a ring, n is an integer of 0 to 2, and wherein in general formula [1-2], Z$_1$ and Z$_2$ are each independently selected from the group consisting of structures illustrated below, and each * indicates a bonding position,

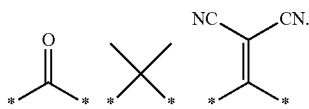

2. The organic compound according to claim 1, wherein R$_3$ is a hydrogen atom.

3. The organic compound according to claim 1, wherein the organic compound is represented by general formula [4]:

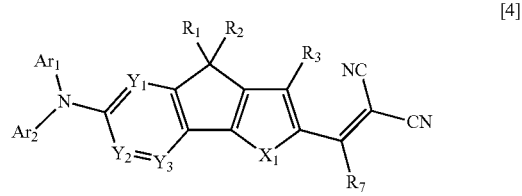

[4]

where in general formula [4], X$_1$ is oxygen or sulfur, wherein in general formula [4], each of Y$_1$ to Y$_3$ is a carbon atom or a nitrogen atom and is optionally the same or different, and wherein when one of Y$_1$ to Y$_3$ is a carbon atom, the carbon atom optionally has a substituent selected from the group consisting of a hydrogen atom, a halogen atom, a cyano group, and an alkyl group, and the alkyl group optionally has a halogen atom as a substituent.

4. The organic compound according to claim 1, wherein in general formula [1], Y$_1$ to Y$_3$ are each a carbon atom.

5. The organic compound according to claim 1, wherein in general formula [1], the at least one of Y$_1$ to Y$_3$ is a nitrogen atom.

6. The organic compound according to claim 5, wherein Z$_1$ in formula [1-2] is a carbonyl group.

7. An organic electronic element comprising a pair of electrodes and an organic compound layer disposed between the pair of electrodes, wherein the organic compound layer contains the organic compound according to claim 1.

8. A photoelectric conversion element comprising an electron-collecting electrode, a hole-collecting electrode, an organic compound layer disposed between the electron-collecting electrode and the hole-collecting electrode, wherein the organic compound layer contains the organic compound according to claim 1.

9. The photoelectric conversion element according to claim 8, wherein the organic compound layer includes a photoelectric conversion layer, and wherein the photoelectric conversion layer contains an organic n-type compound.

10. The photoelectric conversion element according to claim 9, further comprising a second organic compound layer disposed between the hole-collecting electrode and the photoelectric conversion layer.

11. An image pickup element comprising a photoelectric conversion element according to claim 8, a readout circuit connected to the photoelectric conversion element, and a signal processing circuit connected to the readout circuit.

12. The image pickup element according to claim 11, wherein the photoelectric conversion element includes a second photoelectric conversion layer, and wherein the second photoelectric conversion layer photoelectrically converts light having a different wavelength from that of light photoelectrically converted by the photoelectric conversion layer.

13. An imaging device comprising: an imaging optical system and an imaging element that receives light passing through the image pickup optical system, wherein the imaging element is the imaging element according to claim 11.

14. The imaging device according to claim 13, further comprising a receiving unit that receives a signal from the outside, wherein the signal is a signal to control at least one of the imaging range, the start of an imaging operation, and the end of the imaging operation of the imaging device.

15. The imaging device according to claim 13, further comprising a transmitting unit that transmits an acquired image to the outside.

16. An imaging device comprising the imaging element according to claim 11 and a housing that accommodates the imaging element, wherein the housing includes a connection portion that is connectable to an imaging optical system.

17. An organic compound represented by general formula [2]:

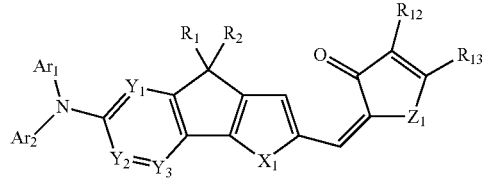

[2]

where in general formula [2], $Ar_1$ and $Ar_2$ are each independently selected from the group consisting of an aryl group and a heteroaryl group, $Ar_1$ and $Ar_2$ each optionally have a halogen atom, a cyano group, an alkyl group, an alkoxy group, an aryl group, or a heteroaryl group as a substituent, the substituent optionally further has a halogen atom, a cyano group, an alkyl group, or an alkoxy group as a substituent, $Ar_1$ and $Ar_2$ are optionally combined with each other to form a ring, wherein in general formula [2], $R_1$ and $R_2$ are each independently selected from the group consisting of a hydrogen atom, a halogen atom, a cyano group, an alkyl group, an aryl group, and a hetero aryl group, the alkyl group optionally has a halogen atom as a substituent, each of the aryl group and the heteroaryl group each denoted by $R_1$ or $R_2$ optionally further has a halogen atom, a cyano group, an alkyl group, or an alkoxy group as a substituent, $R_1$ and $R_2$ are optionally combined with each other to form a ring, where in general formula [2], $X_1$ is oxygen or sulfur, wherein in general formula [2], $R_{12}$ and $R_{13}$ are each independently selected from the group consisting of a hydrogen atom, a halogen atom, a cyano group, an alkyl group, an alkenyl group, an alkynyl group, an aryl group, and a heteroaryl group, $R_{12}$ and $R_{13}$ each optionally have a halogen atom, a cyano group, an alkyl group, an alkoxy group, an aryl group, or a hetero aryl group as a substituent, $R_{12}$ and $R_{13}$ are optionally combined with each other to form a ring, wherein in general formula [2], $Y_1$ to $Y_3$ are a carbon atom or a nitrogen atom and are the same or different, wherein when at least one of $Y_1$ to $Y_3$ is a carbon atom, the carbon atom optionally has a substituent selected from the group consisting of a hydrogen atom, a halogen atom, a cyano group, and an alkyl group, the alkyl group optionally has a halogen atom as a substituent, and wherein in general formula [2], $Z_1$ is one selected from the group consisting of structures illustrated below, and each * indicates a bonding position,

18. The organic compound according to claim 17, wherein the ring formed by combining $R_{12}$ and $R_{13}$ is a benzene ring, a naphthalene ring, a pyridine ring, a pyrimidine ring, a pyrazine ring, a pyridazine ring, a quinoline ring, an isoquinoline ring, a quinoxaline ring, a thiophene ring, a benzothiophene ring, a furan ring, or a benzofuran ring.

19. The organic compound according to claim 17, wherein $Z_1$ is a carbonyl group.

20. An organic compound represented by general formula [3]:

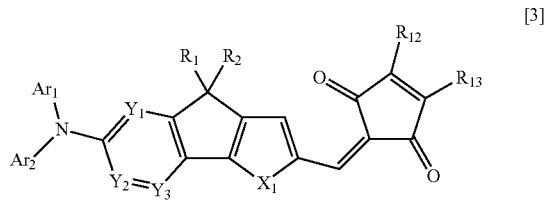

[3]

where in general formula [3], $Ar_1$ and $Ar_2$ are each independently selected from the group consisting of an aryl group and a heteroaryl group, $Ar_1$ and $Ar_2$ each optionally have a halogen atom, a cyano group, an alkyl group, an alkoxy group, an aryl group, or a heteroaryl group as a substituent, the substituent optionally further has a halogen atom, a cyano group, an alkyl group, or an alkoxy group as a substituent, $Ar_1$ and $Ar_2$ are optionally combined with each other to form a ring, wherein in general formula [3], $R_1$ and $R_2$ are each independently selected from the group consisting of a hydrogen atom, a halogen atom, a cyano group, an alkyl group, an aryl group, and a hetero aryl group, the alkyl group optionally has a halogen atom as a substituent, each of the aryl group and the heteroaryl group each denoted by $R_1$ or $R_2$ optionally further has a halogen atom, a cyano group, an alkyl group, or an alkoxy group as a substituent, $R_1$ and $R_2$ are optionally combined with each other to form a ring, where in general formula [3], $X_1$ is oxygen or sulfur, wherein in general formula [3], $R_{12}$ and $R_{13}$ are each independently selected from the group consisting of a hydrogen atom, a halogen atom, a cyano group, an alkyl group, an alkenyl group, an alkynyl group, an aryl group, and a heteroaryl group, $R_{12}$ and $R_{13}$ each optionally have a halogen atom, a cyano group, an alkyl group, an alkoxy group, an aryl group, or a hetero aryl group as a substituent, $R_{12}$ and $R_{13}$ are optionally combined with each other to form a ring, wherein in general formula [3], $Y_1$ to $Y_3$ are a carbon atom or a nitrogen atom and are the same or different, wherein when at least one of $Y_1$ to $Y_3$ is a carbon atom, the carbon atom optionally has a substituent selected from the group consisting of a hydrogen atom, a halogen atom, a cyano group, and an alkyl group, the alkyl group optionally has a halogen atom as a substituent.

* * * * *